(12) United States Patent
Shanler et al.

(10) Patent No.: US 9,980,983 B2
(45) Date of Patent: *May 29, 2018

(54) PEROXIDE FORMULATIONS AND METHODS AND APPLICATORS FOR USING THE SAME

(71) Applicant: ACLARIS THERAPEUTICS, INC., Malvern, PA (US)

(72) Inventors: Stuart D. Shanler, Malvern, PA (US); Christopher Powala, Radnor, PA (US); Christopher Phillips, Doylestown, PA (US); Brian Beger, Newtown, PA (US); Charles Rodney Greenaway Evans, Surrey (GB); Sian Tiong Lim, Surrey (GB); Marc Barry Brown, Watford Hertfordshire (GB); Michael A. Botta, Ridge, NY (US); Thomas Nagler, Greenlawn, NY (US)

(73) Assignee: ACLARIS THERAPEUTICS, INC., Malvern, PA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/591,894

(22) Filed: May 10, 2017

(65) Prior Publication Data
US 2018/0000863 A1     Jan. 4, 2018

Related U.S. Application Data

(63) Continuation of application No. 14/692,665, filed on Apr. 21, 2015, now Pat. No. 9,675,639.

(60) Provisional application No. 61/982,217, filed on Apr. 21, 2014, provisional application No. 62/085,466, filed on Nov. 28, 2014.

(51) Int. Cl.
| | |
|---|---|
| *A61K 8/00* | (2006.01) |
| *A61K 33/40* | (2006.01) |
| *A61K 31/045* | (2006.01) |
| *A61K 9/00* | (2006.01) |
| *A61K 8/34* | (2006.01) |
| *A61Q 19/00* | (2006.01) |
| *A61Q 19/08* | (2006.01) |
| *A61K 47/10* | (2017.01) |
| *A61K 8/22* | (2006.01) |
| *A61M 35/00* | (2006.01) |
| *A61K 9/08* | (2006.01) |

(52) U.S. Cl.
CPC ............ *A61K 33/40* (2013.01); *A61K 8/22* (2013.01); *A61K 8/34* (2013.01); *A61K 9/0014* (2013.01); *A61K 9/08* (2013.01); *A61K 47/10* (2013.01); *A61M 35/003* (2013.01); *A61Q 19/00* (2013.01); *A61Q 19/08* (2013.01); *A61K 2800/872* (2013.01); *A61M 2205/7545* (2013.01)

(58) Field of Classification Search
None
See application file for complete search history.

(56) References Cited

U.S. PATENT DOCUMENTS

| | | |
|---|---|---|
| 825,883 A | 7/1906 | Heinrich |
| 1,139,774 A | 5/1915 | Knox |
| 3,949,072 A | 4/1976 | Tenta |
| 3,954,974 A | 5/1976 | Herzog et al. |
| 4,018,802 A | 4/1977 | Cragoe, Jr. et al. |
| 4,112,121 A | 9/1978 | Tenta |
| 4,128,564 A | 12/1978 | Cragoe, Jr. et al. |
| 4,363,815 A | 12/1982 | Yu et al. |
| 4,428,933 A | 1/1984 | King |
| 4,438,102 A | 3/1984 | Ganci |
| 4,485,091 A | 11/1984 | Fitton |
| 4,518,583 A | 5/1985 | Gallina |
| 4,588,590 A | 5/1986 | Bernstein |
| 4,826,681 A | 5/1989 | Jacquet et al. |
| 5,330,745 A | 7/1994 | McDow |
| 5,348,556 A | 9/1994 | Minns et al. |
| 5,362,915 A | 11/1994 | Maschler et al. |
| 5,380,764 A | 1/1995 | Herzog |
| 5,472,715 A | 12/1995 | Uehara |
| 5,594,015 A | 1/1997 | Kurtz et al. |
| 5,736,582 A | 4/1998 | Devillez |
| 5,824,694 A | 10/1998 | Kurtz et al. |
| 5,916,568 A | 6/1999 | Smyth et al. |
| 5,958,984 A | 9/1999 | Devillez |
| 6,028,104 A | 2/2000 | Schmidt et al. |

(Continued)

FOREIGN PATENT DOCUMENTS

| | | |
|---|---|---|
| CA | 2437823 A1 | 8/2008 |
| EP | 1393629 A1 | 3/2004 |

(Continued)

OTHER PUBLICATIONS

Supplementary European Search Report for EP 15783903.6 dated Nov. 23, 2017.
Singapore Search Report and Written Opinion for SG 11201608775X dated Dec. 22, 2017.
"FDA Warns Consumers Against Drinking High-Strength Hydrogen Peroxide for Medicinal Use," <https://wayback.archive-it.org/7993/20161024051233/http://www.fda.gov/NewsEvents/Newsroom/PressAnnouncements/2006/ucm108701.htm>, Dated Jul. 27, 2006.
"High-Strength Hydrogen Peroxide," https://wayback.archive-it.org/7993/20170112170534/http:/www.fda.gov/Safety/MedWatch/SafetyInformation/SafetyAlertsforHumanMedicalProducts/ucm150592.htm>, Dated Jul. 27, 2006.
"Hydrogen peroxide (H2O2) safe storage and handling," <https://www.fpl.fs.fed.us/documnts/pdf2010/fpl_2010_anderson001.pdf>, Dated 2010.

(Continued)

*Primary Examiner* — Jeffrey T. Palenik
(74) *Attorney, Agent, or Firm* — Pepper Hamilton LLP

(57) ABSTRACT

Embodiments are directed to a stable composition comprising stabilized hydrogen peroxide and 2-propanol and applicators configured to store, dispense, and apply such stable compositions. Such compositions may be used to treat skin conditions such as warts, condyloma accuminatum, molluscum contagiosum, acrochordons, seborrheic keratosis, or a combination thereof. Some embodiments also describe take home compositions, in office compositions, over-the-counter compositions, and kits for the use of such compositions.

25 Claims, 20 Drawing Sheets

(56) References Cited

U.S. PATENT DOCUMENTS

| | | | |
|---|---|---|---|
| 6,071,541 | A | 6/2000 | Murad |
| 6,146,640 | A | 11/2000 | Dyke |
| 6,231,848 | B1 | 5/2001 | Breitenbach et al. |
| 6,245,957 | B1 | 6/2001 | Wagner et al. |
| 7,138,146 | B2 | 11/2006 | Miller et al. |
| 7,381,427 | B2 | 6/2008 | Ancira et al. |
| 8,273,385 | B1 | 9/2012 | Shine |
| 2003/0008018 | A1 | 1/2003 | Miller et al. |
| 2003/0060517 | A1 | 3/2003 | Tucker et al. |
| 2003/0077386 | A1 | 4/2003 | Azevedo |
| 2004/0101571 | A1 | 5/2004 | Reed et al. |
| 2004/0137077 | A1 | 7/2004 | Ancira et al. |
| 2005/0244344 | A1 | 11/2005 | Giles |
| 2005/0255172 | A1 | 11/2005 | Omidbakhsh |
| 2005/0266081 | A1 | 12/2005 | Rogozinski |
| 2006/0110348 | A1 | 5/2006 | Ohlhausen et al. |
| 2006/0198798 | A1 | 9/2006 | Tichy et al. |
| 2007/0003494 | A1 | 1/2007 | Mori et al. |
| 2007/0053850 | A1 | 3/2007 | Tichy et al. |
| 2007/0111954 | A1 | 5/2007 | Crutchfield, III et al. |
| 2008/0167681 | A1 | 7/2008 | Stenton |
| 2008/0206161 | A1 | 8/2008 | Tamarkin et al. |
| 2011/0092562 | A1 | 4/2011 | Dow |
| 2012/0283328 | A1 | 11/2012 | Modi |
| 2012/0308623 | A1 | 12/2012 | Taxt-Lamolle et al. |
| 2011/3000423 | | 1/2013 | Kirk, III et al. |
| 2014/0030314 | A1 | 1/2014 | Larson et al. |
| 2015/0328259 | A1 | 11/2015 | Shanler et al. |

FOREIGN PATENT DOCUMENTS

| | | | |
|---|---|---|---|
| GB | 2285218 | A | 7/1995 |
| JP | H03506024 | A | 12/1991 |
| JP | H04159229 | A | 6/1992 |
| JP | 0601891 | A1 | 6/1994 |
| JP | H06206825 | A | 7/1994 |
| JP | H07165553 | A | 6/1995 |
| JP | 2004518715 | A | 6/2004 |
| MX | PA03007151 | A | 10/2004 |
| WO | 1998033490 | A2 | 8/1998 |
| WO | 1999013888 | A1 | 3/1999 |
| WO | 1999037295 | A1 | 7/1999 |
| WO | 2002064151 | A1 | 8/2002 |
| WO | 2008024422 | A2 | 2/2008 |
| WO | 2010086660 | A1 | 8/2010 |

OTHER PUBLICATIONS

"Hydrogen Peroxide," (https://toxnet.nlm.nih.gov/cgi-bin/sis/search2/r?dbs+hsdb:@term+@rn+7722-84-1>, Dated Jun. 24, 2005.
Brickner "Fibroma Molluscum Gravidarum: A New Clinical Entity" 1906, Am. J. of Obstet. Gyne. 53:191-199.
Doyle, ACRS (Aclaris Therapeutics): Caustic & Corrosive Stock—You Will Get Burned (PT: $5); available online at https://www.scribd.com/document/346246062/ACRS-Aclaris-Therapeutics-Caustic-Corrosive-Stock-You-WILL-Get-Burned-PT-5; published online Apr. 25, 2017.
Doyle (ArtDoyle2017). $ACRS Short / $CNCE Long next week. "$ACRS did studies on hydrogen peroxide, you know. 6% of the time, it works eve . . . https://t.co/eSXs31GabZ". Apr. 21, 2017, 17:31 UTC. Tweet.
Doyle (ArtDoyle2017). "Coming next week: $ACRS Short / $CNCE Long. An FDA approval won't matter. This off the shelf chemical company ($ACR . . . https://t.co/6prHtxrsii". Apr. 21, 2017, 16:09 UTC. Tweet.
Doyle (ArtDoyle2017). "$ACRS Short/$CNCE Long Report 1: $ACRS Aclaris Therapeutics; Caustic & Corrosive—You Will Get Burned (PT $5): https://t.co/1fZsaxjqvL". Apr. 25, 2017, 16:00 UTC. Tweet.

Epstein et al., Skin Surgery, 6th Ed. (1987) W. B. Saunders, Philadelphia, Pa., pp. 180-182.
Gusakov et al. "Opyt lechenia borodavok pergidrolem [perhydrol treatment experience with warts]" Oct. 1988, Vestinik dermatologii I venerologii 10:56-57.
International Search Report and Written Opinion for PCT/US2015/026948 dated Jul. 14, 2015.
International Search Report for PCT/US1002/003530 dated Jul. 22, 2002.
Klein-Szanto et al. "Effects of Peroxides on Rodent Skin: Epidermal Hyperplasia and Tumor Promotion" 1982, The Journal of Investigative Dermatology 79: 30-34.
Lee et al. "TCA chemical peeling. Procedures, complication and self-evaluation of therapeutic effect in 242 patients" 1993, Korean Journal of Dermatology 31:1-8 (abstract).
Macleod "Practical Handbook of the Pathology of the Skin" 1903, H.K. Lewis 91:132.
Nanney et al. "Altered distribution of phospholipase C-.gamma.1 in Benign hyperproliferative epidermal diseases" 1992, Cell Growth & Differentiation 3:233-239.
Nanney et al. "Epidermal growth factor receptors in idiopathic and virally induced skin diseases" Am. J. Pathology 140(4):915.
Nardin et al. "Alfa-Hidroxiacidos: Aplicacoes Cosmeticas E Dermatologicas" (1999) Cademo de Farmacia 15(1):7-14.
Oliver et al. "Influenzal Pneumonia: the intavenous injection of hydrogen peroxide" 1920, The Lancet 432-433.
O'Toole et al. "Hydrogen Peroxide Inhibits Human Keratinocyte Migration" 1996, Dermatologic Surgery 22:525-529.
Rathbun "A Method for Removing the Acrochordon (Skin Tag)" 1990, Kansas Medicine 91(1):11-12.
Schumb et al. "Technical Report No. 42—Hydrogen Peroxide" (Sep. 15, 1953) MIT Dept. of Chemistry and Chemical Engineering, Division of Industrial Cooperation Project 6552, Cambridge, Massachusetts.
Shetty, "Hydrogen peroxide burn of the oral mucosa," Ann Pharmacother. (Feb. 2006), 40(2) pp. 351. Epub (Jan. 31, 2006).
Sowden et al. "The Management of Seborrhoeic Keratoses by General Practitioners, Surgeons, and Dermatologists" 1998, British Journal of Dermatology 139:348-349.
Strother "Acrochordonectomy made easy" 1998, Clinician Reviews, 8(3):154-155.
Supplemental European Search Report for EP02720927 dated Oct. 26, 2004.
Sutton et al. "Handbook of Diseases of the Skin" 1949, C. V. Moseby Company p. 589.
Taylor "On the Mode of Development and Course of Molluscum Fibrosum and on the Question of its Relationship to Acrochordon and Other Cutaneous Outshoots", Journal of Cutaneous and Genito-Urinary Disease 5:41-51, Dated Feb. 1887.
Tredwin et al., "Hydrogen peroxide tooth-whitening (bleaching) products: Review of adverse effects and safety issues," British Dental Journal (2006), (200) pp. 371-376.
Tur et al. "Topical hydrogen peroxide treatment of ischemic ulcers in the guinea pig: blood recruitment in multiple skin sites" 1995, Journal of the American Academy of Dermatology 33:217-221.
Walsh, "Safety issues relating to the use of hydrogen peroxide in dentistry," Australian Dental Journal (2000), (45) pp. 257-269.
Database WPI "Electrolyte for micro-arc oxidation of aluminium and its alloys, contains potassium hydroxide, sodium silicate, isopropyl alcohol, hydrogen peroxide and water" Aug. 20, 2011, Thomson Scientific, London, GB.
Database WPI "Pearl tumour curing agent—contains hydrogen peroxide and pref. alcohol and surfactant" Jun. 2, 1992, Thomson Scientific, London, GB.
International Search Report and Written Opinion for PCT/US2017/047350 dated Oct. 30, 2017.
Supplementary Partial European Search Report for EP15783903 dated Aug. 18, 2017.

| Wart Severity Assessment | | Wart Improvement Assessment | |
|---|---|---|---|
| Grade | Descriptor | Grade | Descriptor |
| 0 | Clear: no clinically diagnosable wart (residual erythema and/or fine scaling may be present) | 0 | Total improvement: wart is completely improved (100%); wart is cleared compared to Visit 1. |
| 1 | Mild: Barely evident clinically diagnosable wart, minimally verrucoid, papular lesion with no to minimal hyperkeratosis | 1 | Marked improvement: wart is very much improved (75%) compared with Visit 1 |
| 2 | Moderate: Obvious wart, verrucoid papule with moderate hyperkeratosis | 2 | Moderate improvement: wart is meaningfully improved (50%) compared to Visit 1 |
| 3 | Severe: Conspicuous wart, obvious verrucoid papule with severe hyperkeratosis | 3 | Mild improvement: Wart is slightly improved (25%) compared to Visit 1 |
| | | 4 | No Change: no improvement compared to Visit 1 |
| | | 5 | Worse: wart has worsened compared to Visit 1 |

FIGURE 7

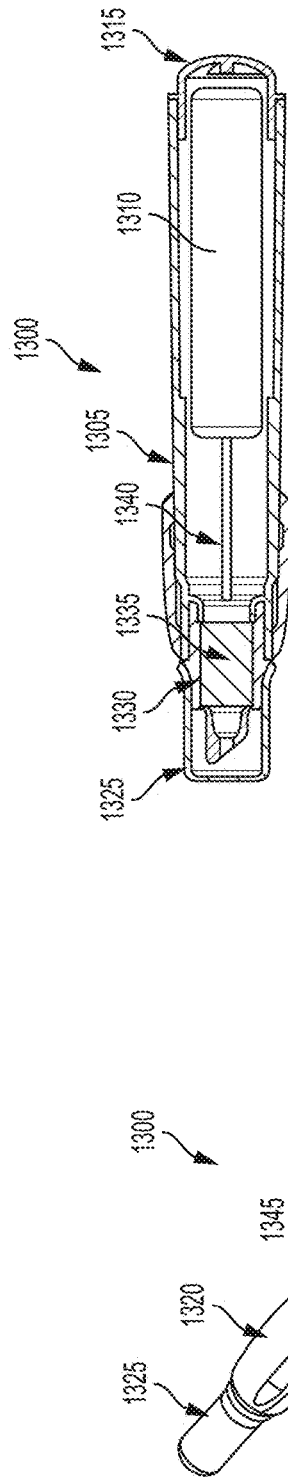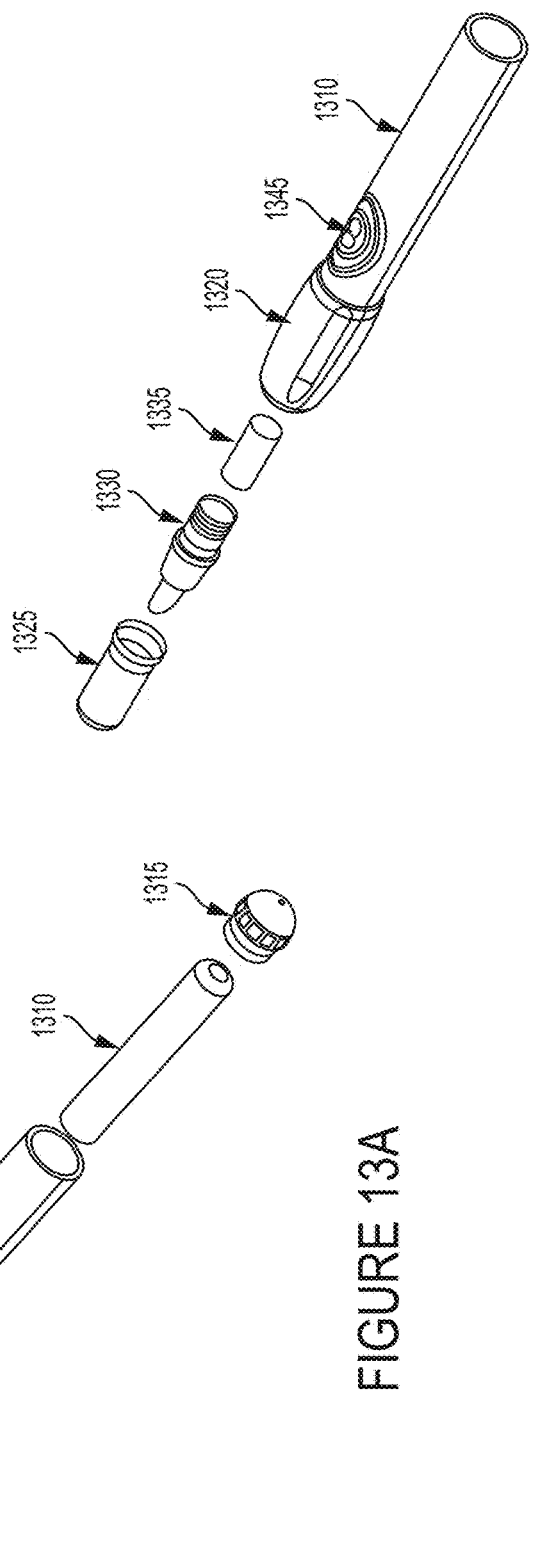
FIGURE 13C
FIGURE 13B
FIGURE 13A

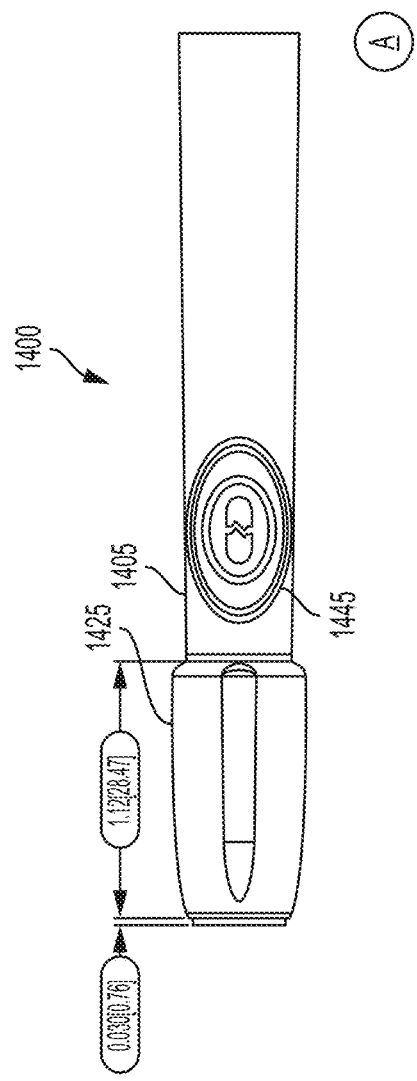
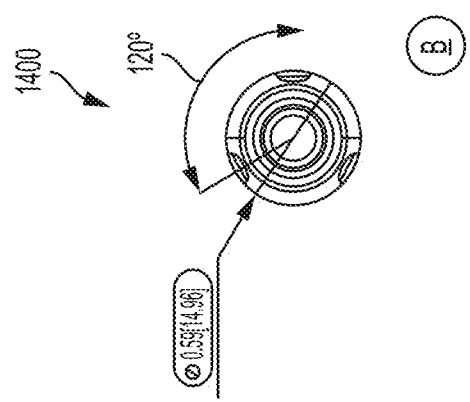
FIGURE 14B

PEROXIDE FORMULATIONS AND METHODS AND APPLICATORS FOR USING THE SAME

BRIEF SUMMARY

Embodiments in this disclosure are directed to a composition comprising hydrogen peroxide and an alcohol. In some embodiments, the hydrogen peroxide is stabilized hydrogen peroxide. In some embodiments, the hydrogen peroxide may be a standard grade, food grade, chemical synthesis grade, semiconductor grade, high-test hydrogen peroxide grade, antimicrobial grade, drinking water grade, pharmaceutical grade or cosmetic grade hydrogen peroxide. In some embodiments, the alcohol may be selected from a primary alcohol, a secondary alcohol, a tertiary alcohol, or a combination thereof. In some embodiments, the alcohol may be selected from 2-propanol, methanol, butanol, 1-propanol, pentanol, hexanol, octanol, nonanol, decanol, 2-pentanol, 2-butanol, benzyl alcohol, ethanol, an isomer thereof, or a combination thereof. In some embodiments, the hydrogen peroxide is in an amount up to about 50% of the composition. In some embodiments the alcohol is in a quantity sufficient to decrease the surface tension of the composition. In some embodiments, the alcohol is in an amount up to about 5% of the composition. In some embodiments, the composition is a solution. In some embodiments, the composition is a gel formulation. In some embodiments, the composition comprises two or more separate components that may be admixed before, at, or near the time of use.

Some embodiments are directed to a topical composition comprising up to about 50% hydrogen peroxide and up to 5% 2-propanol. In some embodiments, the hydrogen peroxide is a stabilized hydrogen peroxide. In some embodiments, the topical composition further includes a stabilizer. The stabilizer may be selected from stannate, sodium pyrophosphate, organophosphonate, nitrate, phosphoric acid, colloidal silicate, any stabilizer known in the art, or a combination thereof. In some embodiments, the 2-propanol is in an amount sufficient to decrease the surface tension while minimizing spread of the composition onto non-targeted skin when applied to a targeted lesion. The composition may be stable for at least two years at 5° C., at least one year at 30° C., at least 6 months at 40° C., or a combination thereof.

In some embodiments, the topical composition comprises about 45% stabilized cosmetic-grade hydrogen peroxide and about 5% 2-propanol, and wherein the topical composition has a surface tension of about 42 mN·m−1 to about 55 mN·m−1 at 37° C. In some embodiments, the topical composition comprises about 40% stabilized cosmetic-grade hydrogen peroxide and about 5% 2-propanol, and wherein the topical composition has a surface tension of about 42 mN·m−1 to about 55 mN·m−1 at 37° C. In some embodiments, the topical composition comprises about 32.5% stabilized cosmetic-grade hydrogen peroxide and about 5% 2-propanol, and wherein the topical composition has a surface tension of about 42 mN·m−1 to about 55 mN·m−1 at 37° C. In some embodiments, the topical composition comprises about 25% stabilized cosmetic-grade hydrogen peroxide and about 5% 2-propanol, and wherein the topical composition has a surface tension of about 42 mN·m−1 to about 55 mN·m−1 at 37° C.

Some embodiments are directed to a composition comprising hydrogen peroxide and a surface tension modifying agent. In some embodiments, the surface tension modifying agent is an agent stable in compositions comprising concentrations of hydrogen peroxide disclosed in embodiments herein. In some embodiments, the surface tension modifying agent is in a quantity sufficient to enhance the therapeutic efficacy of the composition. In some embodiments, the surface tension modifying agent is in a quantity sufficient to modify the surface tension while maintaining stability of the composition sufficient for use as a commercially viable formulation. In some embodiments, the surface tension modifying agent is an alcohol. In some embodiments, the surface tension modifying agent is 2-propanol.

Embodiments herein also describe a method of treating a skin condition comprising administering a composition having up to about 50% hydrogen peroxide and an alcohol to a subject in need thereof. The skin condition may be a virally induced or non-virally induced cutaneous growth or proliferation. The skin condition may be a benign neoplasm, premalignancy or malignancy. The skin condition may be an inflammatory condition. The skin condition may be a hyperproliferative condition. The skin condition may be aging including intrinsic (e.g., chronological) and extrinsic changes (e.g., photoaging, ultraviolet light induced changes), pigmentary changes, fine lines and rhytides. In some embodiments, the skin condition may be selected from Human Papilloma Virus induced lesions e.g., warts, common warts, palmoplantar warts, flat warts, recurrent warts, recalcitrant warts, treatment naïve warts, epidermodysplasia verruciformis related warts, anogenital warts, condyloma accuminatum, cervical dysplasias or neoplasias, e.g., cervical intraepithelial neoplasia (CIN); Herpesvirus related lesions including those induced by HHV-1 (HSV-1), HHV-2 (HSV-2), HHV-3 (varicella-zoster virus) e.g., chicken pox, Herpes zoster, shingles; Poxvirus induced lesions e.g., molluscum contagiosum, orf, callus, cutaneous horns, corns, acrochordons, fibroepithelial polyps, prurigo nodularis, actinic keratoses, squamous cell carcinoma, squamous cell carcinoma in situ, keratoacanthoma, basal cell carcinoma, cutaneous lymphomas and benign lymphocytic infiltrates & hyperplasias of the skin, clear cell acanthoma, large cell acanthoma, epidermolytic acanthoma, porokeratosis, hyperkeratosis, keratosis pilaris lichenoid keratosis, acanthosis, acanthosis nigricans, confluent and reticulated papillomatosis, nevi, including e.g., dermal nevi, epidermal nevi, compound nevi, ILVEN (inflammatory linear verrucous epidermal nevi), nevus sebaceous, nevus comedonicus, and the like; acne, e.g., comedonal acne, inflammatory acne, papular acne, pustular acne, cystic acne; cysts, e.g., epidermoid cysts, milia, trichilemmal cysts, follicular cysts, proliferating cysts, dermoid cysts, pilonidal cysts, apocrine cysts, eccrine cysts, sebaceous cysts, mucous cysts, myxoid cysts, ganglion cysts, synovial cysts, vellus hair cysts, steatocystoma, hidrocystoma; adnexal neoplasms e.g., trichofolliculoma, fibrofolliculoma, perifollicular fibroma, trichodiscoma, nevus sebaceous, chondroid syringoma, trichoepithelioma, trichoblastoma, desmoplastic trichoepithelioma, pilomatricoma, pilomatrical carcinoma, tricholemmoma, trichelemmal carcinoma, tumor of the follicular infundibulum, tricoadenoma, proliferating pilar tumor, sebaceous hyperplasia, sebaceous adenoma, sebaceous epithelioma, sebaceous carcinoma, syringoma, poroma, hidradenoma, apocrine hidradenoma, spiradenoma, cylindroma, eccrine nevus (eccrine hamartoma), papillary adenoma, papillary adenocarcinoma; benign melanocytic proliferations or neoplasms e.g., ephilides, café-au-lait macules, Becker's melanosis, lentigines, solar lentigines, lentigo simplex, mucosal melanocytic lesions, Mongolian spots, Nevus of Ota, blue nevus, common acquired melanocytic nevi (nevocellular nevus, "moles"), congenital nevi, nevus spilus, recurrent nevi; vascular and perivascular neoplasms and reactive hyperplasias e.g., hemangiomas, cherry angiomas, hobnail hemangiomas (targeted hemosiderotic hemangiomas), tufted angiomas, hemangioendotheliomas, angiolymphoid hyperplasia with eosinophilia (ALHE), Glomus tumors (glomangiomas), hemangiopericytomas; cutaneous neural and neuroendocrine neoplasms e.g., neuromas, Schwannomas, neurofibromas, nerve sheath tumor, nerve sheath myxoma, neurothekeoma, granular cell tumor; fibrotic and fibrohistiocytic proliferations e.g., acrochordons, fibroepithelial polyps, fibromas, fibrous papules, angiofibromas, pearly penile papules, periungual fibromas, dermatofibromas, fibrokeratomas, sclerotic or pleomorphic fibromas, connective tissue nevi; cutaneous scars, hyperplasias, keloids, rosacea, cutaneous fungal, dermatophyte & mold infections, onychomycosis, hyperpigmentation, rhytides, psoriasis, malignant melanoma, seborrheic keratosis, seborrheic keratosis variants including e.g., dermatosis papulosis nigra, inverted follicular keratosis/keratoma warty dyskeratosis/warty dyskeratoma, acrokeratosis verruciformis, stucco keratosis; or a combination thereof.

Some embodiments describe a method of treating warts comprising administering a composition having up to about 50% hydrogen peroxide and an alcohol to a subject in need thereof.

Some embodiments describe a method of treating seborrheic keratosis comprising administering a composition having up to about 50% hydrogen peroxide and an alcohol to a subject in need thereof. In some embodiments, the alcohol is in an amount capable of decreasing the surface tension of the composition. In some embodiments, the alcohol is in an amount capable of increasing the wettability of the surface of the skin or skin lesion. In some embodiments, the alcohol is in an amount capable of increasing the permeability of the composition into the subject's skin and/or the skin lesion. In some embodiments, the alcohol is in an amount capable of enhancing the clinical efficacy of the composition. In some embodiments, the alcohol is in an amount capable of enhancing the clinical efficacy of the composition while maintaining stability sufficient for a commercially viable composition.

Some embodiments herein are directed to a topical solution formulation comprising up to about 50% hydrogen peroxide and an alcohol. In some embodiments, the solution is comprised of two or more parts to be mixed at or immediately before the time of application.

Some embodiments herein are directed to a gel composition comprising up to about 50% hydrogen peroxide, an alcohol, and a gelling agent. In some embodiments, the gel composition is comprised of two or more parts that may be mixed at or immediately before the time of application.

Some embodiments herein describe a composition consisting essentially of up to about 50% hydrogen peroxide and an alcohol. Some embodiments herein describe a composition consisting of up to about 50% hydrogen peroxide and an alcohol. In some embodiments, the alcohol is a primary alcohol, a secondary alcohol, a tertiary alcohol, or a combination thereof. In some embodiments, the alcohol is not 1-propanol, ethanol, butanol, pentanol, hexanol, octanol, nonanol, decanol, 2-butanol, 2-pentanol, or benzyl alcohol. In some embodiments, the alcohol is 2-propanol.

Some embodiments herein are directed toward devices for administering the compositions of embodiments herein. In some embodiments, the devices may include an applicator configured to safely and effectively deliver the compositions of embodiments herein to the targeted skin of a patient. Some embodiments herein include an applicator configured to store and dispense a topical composition comprising an agent selected from a caustic agent, an unstable agent or a combination thereof, the applicator comprising a frangible ampoule having the agent disposed therein, an applicator body having the frangible ampoule arranged therein; an applicator hub in fluid communication with the applicator body; a tip arranged at a proximal end of the applicator hub; and a filter arranged between the frangible ampoule and the tip. In some embodiments, the topical composition comprises from about 25% to about 50% hydrogen peroxide and up to 5% 2-propanol. In some embodiments, the agent comprises from about 25% hydrogen peroxide to about 50% hydrogen peroxide. In some embodiments, the frangible ampoule further includes up to 5% 2-propanol. In some embodiments, the applicator body further comprises an additional ingredient of the topical composition disposed therein, whereby the agent is released from the frangible ampoule responsive to the frangible ampoule being ruptured and is mixed with the additional ingredient in the applicator body prior to administration of the topical composition. In some embodiments, the topical composition is released from the frangible ampoule responsive to the frangible ampoule being ruptured and flows through the applicator body, the filter, and out of the applicator through the tip. In some embodiments, the applicator further includes a pressure area arranged on an outer surface of the applicator body to indicate a portion of the applicator body to apply pressure to rupture the frangible ampoule.

Some embodiments are directed to an applicator configured to store and dispense a topical composition comprising from about 25% to about 50% hydrogen peroxide and up to 5% 2-propanol, the applicator comprising a frangible ampoule having the topical composition disposed therein, an applicator body having the frangible ampoule arranged therein, an applicator hub in fluid communication with the applicator body, a tip arranged at a proximal end of the applicator body; and a filter arranged between the frangible ampoule and the tip. In some embodiments, the frangible ampoule is formed from at least one of glass, plastic, borosilicate glass, Type 1 borosilicate glass, and tinted glass. In some embodiments, the applicator body is formed from polypropylene, high-density polyethylene, low-density polyethylene, polyvinyl chloride, polyethylene, or a combination thereof. In some embodiments, the filter is configured to prevent shards of a ruptured frangible ampoule from passing through and to allow the topical composition to flow through. In some embodiments, the filter is formed from at least one of polypropylene, high-density polyethylene, low-density polyethylene, polyethylene, polystyrene, a ceramic material, a foam material, sand, diatomaceous earth, and paper fibers.

Some embodiments are directed to a method of treating a skin condition, the method comprising administering a topical composition comprising up to 50% hydrogen peroxide and up to 5% 2-propanol using an applicator comprising a frangible ampoule having the topical composition disposed therein, an applicator body having the frangible ampoule arranged therein, an applicator hub in fluid communication with the applicator body, a tip arranged at a proximal end of the applicator hub, and a filter arranged between the frangible ampoule and the tip. In some embodiments, administering the topical composition comprises applying a squeezing force to the exterior surface of the applicator body to dispense the composition. In some embodiments, administering the topical composition comprises contacting the tip with a targeted lesion of the skin condition whereby the topical composition dispenses through the tip onto the targeted lesion. In some embodiments, administering the topical composition further comprises applying pressure to a pressure area arranged on an outer surface of the applicator body causing the frangible ampoule to rupture. In some embodiments, administering the topical composition comprises causing the frangible ampoule to rupture and release the topical composition through the tip; and contacting the tip to a targeted lesion of the skin condition.

In some embodiments, the applicator may include a frangible ampoule configured to store the compositions of embodiments herein arranged within an applicator body. In some embodiments, the ampoule may be formed from glass or other similar frangible materials, such as borosilicate glass. In some embodiments, the applicator body may be formed from various flexible materials, including, without limitation high-density polyethylene (HDPE), low-density polyethylene (LDPE) or various combinations or blends thereof. In some embodiments, the compositions of embodiments herein may be released from the ampoule by applying manual pressure (for instance, "squeezing") on the applicator body in a direction toward the ampoule sufficient to cause the ampoule to break apart. In some embodiments, the compositions of embodiments herein released from the ampoule may flow through a filter configured to filter glass shards from the broken ampoule while allowing the compositions of embodiments herein to flow therethrough. In some embodiments, at least one portion of the applicator may include a hydrophobic material, such as the filter and/or the tip. In some embodiments the hydrophobic material is composed of polyester or co-polyester polymers, acrylic, modified acrylic (e.g., modacrylic), polypropylene, polyethylene or combinations or mixtures thereof. Non-limiting examples of hydrophobic materials may also include materials including, coated with, and/or modified by silanes, alkylsilanes, fluoroalkylsilanes, silicone, combinations thereof, and derivatives thereof. In some embodiments, the hydrophobic portions of the applicator may operate to impede, reduce, restrict, prevent, and/or substantially prevent the compositions of embodiments herein that have been released from the ampoule from flowing through portions of the applicator and/or out of the tip of the applicator. In some embodiments, the compositions of embodiments herein may flow through the filter and out of the applicator via an applicator tip for application on the skin of a patient. In some embodiments, the tip may include a flocked portion formed from filaments of various chemically compatible and non-reactive materials, such as nylon.

DESCRIPTION OF THE FIGURES

FIG. 7 illustrates the grades and descriptors for the Wart Improvement Assessment score and the Wart Severity Assessment score.

FIGS. 13A-13C depicts an illustrative applicator according to a second embodiment.

FIGS. 14A and 14B depict multiple views of an illustrative applicator body according to some embodiments.

DETAILED DESCRIPTION

Figure 1:
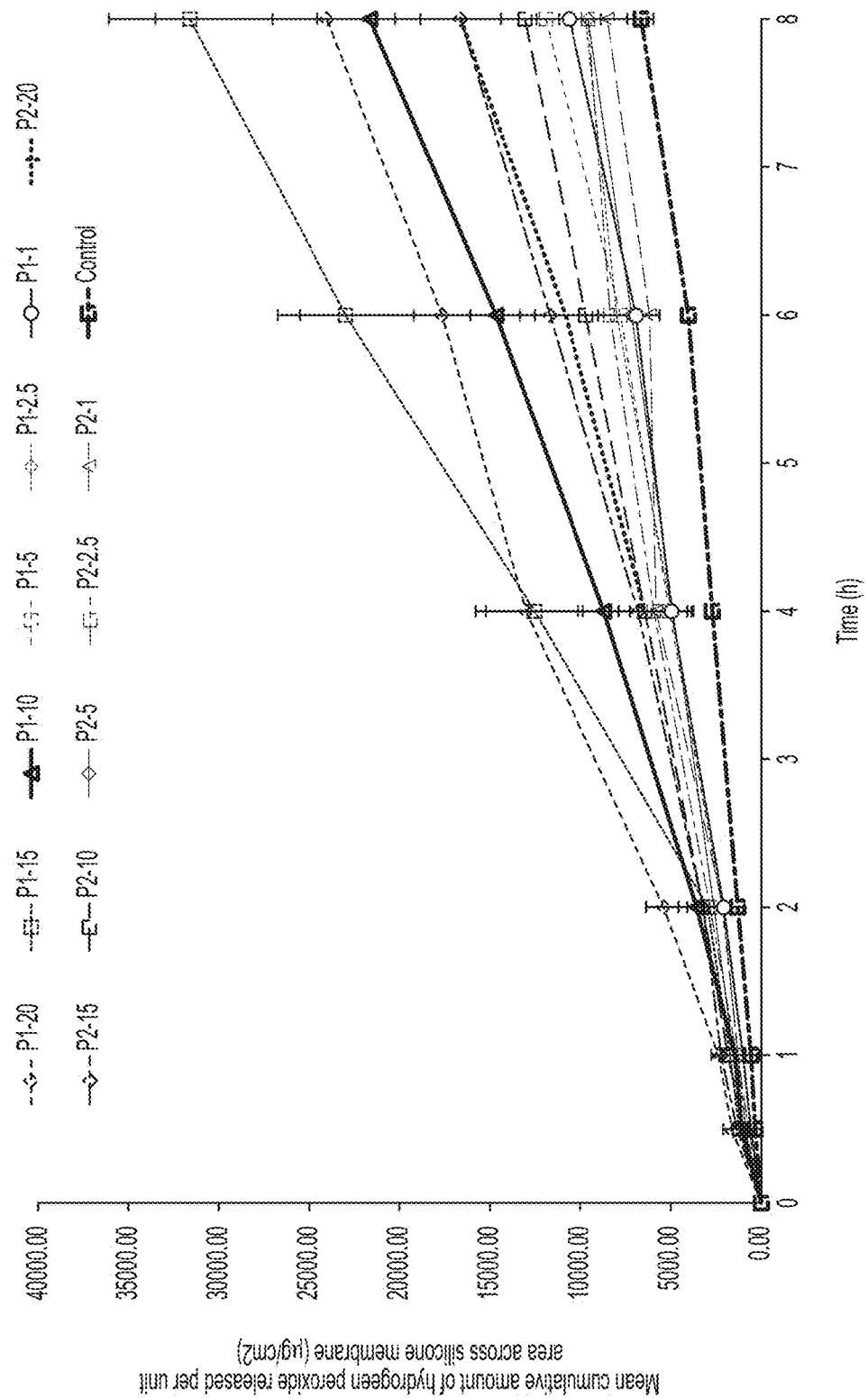
FIG. 1 illustrates the mean cumulative amount of hydrogen peroxide released per unit area across silicone membrane ($\mu g/cm^2$) following application of all 40% w/w hydrogen peroxide formulations. Each time point represents the mean±SD (n=5-6).

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "skin lesion" is a reference to one or more skin lesions and equivalents thereof known to those skilled in the art, and so forth.

As used herein, the term "about" means plus or minus 10% of the numerical value of the number with which it is being used. Therefore, about 50% means in the range of 45%-55%.

"Administering", when used in conjunction with a therapeutic, means to administer a therapeutic directly into or onto a target tissue or to administer a therapeutic to a subject, whereby the therapeutic positively impacts the tissue to which it is targeted. Thus, as used herein, the term "administering", when used in conjunction with a therapeutic, can include, but is not limited to, providing a therapeutic to a subject systemically by, for example, intravenous injection, whereby the therapeutic reaches the target tissue. Administering a composition or therapeutic may be accomplished by, for example, injection, oral administration, topical administration, or by these methods in combination with other known techniques. Such combination techniques may include heating, radiation, ultrasound and the use of delivery agents. Preferably, administering is a self-administration, wherein the therapeutic or composition is administered by the subject themselves. Alternatively, administering may be administration to the subject by a health care provider.

"Providing", when used in conjunction with a therapeutic, means to administer a therapeutic directly into or onto a target tissue, or to administer a therapeutic to a subject whereby the therapeutic positively impacts the tissue to which it is targeted.

The term "animal" as used herein includes, but is not limited to, humans and non-human vertebrates such as wild, domestic and farm animals.

The term "patient" or "subject" as used herein is an animal, particularly a human, suffering from an unwanted disease or condition that may be treated by the therapeutic and/or compositions described herein.

The term "improves" is used to convey that the embodiments provided herein change either the characteristics and/or the physical attributes of the tissue to which the therapeutic composition is being provided, applied or administered. The term "improves" may also be used in conjunction with a diseased state such that when a diseased state is "improved" the symptoms or physical characteristics associated with the diseased state are diminished, reduced or eliminated.

The term "inhibiting" generally refers to prevention of the onset of the symptoms, alleviating the symptoms, or eliminating the disease, condition or disorder.

"Optional" or "optionally" means that the subsequently described event or circumstance may or may not occur, and that the description includes instances where the event occurs and instances where it does not.

As used herein, "room temperature" means an indoor temperature of from about 20° C. to about 25° C. (68 to 77° F.).

Throughout the specification of the application, various terms are used such as "primary," "secondary," "first," "second," and the like. These terms are words of convenience in order to distinguish between different elements, and such terms are not intended to be limiting as to how the different elements may be utilized.

By "pharmaceutically acceptable," "physiologically tolerable," and grammatical variations thereof, as they refer to compositions, carriers, diluents, and reagents or other ingredients of the formulation, can be used interchangeably and represent that the materials are capable of being administered without the production of undesirable physiological effects such as rash, burning, irritation or other deleterious effects to such a degree as to be intolerable to the recipient thereof.

As used herein, the term "cosmetically acceptable" and grammatical variations thereof, as they refer to compositions, carriers, diluents, and reagents or other ingredients of the formulation, represent that the materials used and final composition are not irritating or otherwise harmful to the patient in general and to the skin, in particular, and preferably are pleasant and well tolerated with respect to general appearance, pH, color, smell and texture (feel), that they are not, for example, unacceptably sticky (tacky), oily or drying, and that they do spread easily, absorb into the skin at an acceptable rate of absorption, and are generally moisturizing.

As used herein, the term "therapeutic" means an agent utilized to treat, combat, ameliorate, prevent or improve an unwanted condition or disease of a subject. In part, embodiments described herein may be directed to the treatment of various skin diseases, conditions or disorders or symptoms thereof, including, but not limited to, benign proliferations, neoplasms, premalignancies or malignancies of the skin. The skin condition may be a virally induced or non-virally induced cutaneous growth or proliferation. The skin condition may be an inflammatory condition. The skin condition may be a hyperproliferative condition. The skin condition may be ageing including intrinsic and extrinsic changes (e.g., photoaging (ultraviolet light induced changes)), pigmentary changes, fine lines and rhytides. In some embodiments, the skin condition may be selected from Human Papilloma Virus induced lesions e.g., warts, common warts, palmoplantar warts, flat warts, recurrent warts, recalcitrant warts, treatment naïve warts, epidermodysplasia verruciformis related warts, anogenital warts, condyloma accuminatum, cervical dysplasias or neoplasias, e.g., cervical intraepithelial neoplasia (CIN); Herpesvirus related lesions including those induced by HHV-1 (HSV-1), HHV-2 (HSV-2), HHV-3 (varicella-zoster virus) e.g., chicken pox, Herpes zoster, shingles; Poxvirus induced lesions e.g., molluscum contagiosum, orf; callus, cutaneous horns, corns, acrochordons, fibroepithelial polyps, prurigo nodularis, actinic keratoses, squamous cell carcinoma, squamous cell carcinoma in situ, keratoacanthoma, basal cell carcinoma, cutaneous lymphomas and benign lymphocytic infiltrates & hyperplasias of the skin, clear cell acanthoma, large cell acanthoma, epidermolytic acanthoma, porokeratosis, hyperkeratosis, keratosis pilaris, lichenoid keratosis, acanthosis, acanthosis nigricans, confluent and reticulated papillomatosis, nevi, including e.g., dermal nevi, epidermal nevi, compound nevi, ILVEN (inflammatory linear verrucous epidermal nevi), nevus sebaceous, nevus comedonicus, and the like; acne, e.g., comedonal acne, inflammatory acne, papular acne, pustular acne, cystic acne; cysts, e.g., epidermoid cysts, milia, trichilemmal cysts, follicular cysts, proliferating cysts, dermoid cysts, pilonidal cysts, apocrine cysts, eccrine cysts, sebaceous cysts, mucous cysts, myxoid cysts, ganglion cysts, synovial cysts, vellus hair cysts, steatocystoma, hidrocystoma; adnexal neoplasms e.g., trichofolliculoma, fibrofolliculoma, perifollicular fibroma, trichodiscoma, nevus sebaceous, chondroid syringoma, trichoepithelioma, trichoblastoma, desmoplastic trichoepithelioma, pilomatricoma, pilomatrical carcinoma, trichelemmoma, trichelemmal carcinoma, tumor of the follicular infundibulum, tricoadenoma, proliferating pilar tumor, sebaceous hyperplasia, sebaceous adenoma, sebaceous epithelioma, sebaceous carcinoma, syringoma, poroma, hidradenoma, apocrine hidradenoma, spiradenoma, cylindroma, eccrine nevus (eccrine hamartoma), papillary adenoma, papillary adenocarcinoma; benign melanocytic proliferations or neoplasms e.g., ephilides, café-au-lait macules, Becker's melanosis, lentigines, solar lentigines, lentigo simplex, mucosal melanocytic lesions, Mongolian spots, Nevus of Ota, blue nevus, common acquired melanocytic nevi (nevocellular nevus, "moles"), congenital nevi, nevus spilus, recurrent nevi; vascular and perivascular neoplasms and reactive hyperplasias e.g., hemangiomas, cherry angiomas, hobnail hemangiomas (targeted hemosiderotic hemangiomas), tufted angiomas, hemangioendotheliomas, angiolymphoid hyperplasia with eosinophilia (ALHE), Glomus tumors (glomangiomas), hemangiopericytomas; cutaneous neural and neuroendocrine neoplasms e.g., neuromas, Schwannomas, neurofibromas, nerve sheath tumor, nerve sheath myxoma, neurothekeoma, granular cell tumor; fibrotic and fibrohistiocytic proliferations e.g., acrochordons, fibroepithelial polyps, fibromas, fibrous papules, angiofibromas, pearly penile papules, periungual fibromas, dermatofibromas, fibrokeratomas, sclerotic or pleomorphic fibromas, connective tissue nevi; cutaneous scars, hyperplasias, keloids, rosacea, cutaneous fungal, dermatophyte & mold infections, onychomycosis, hyperpigmentation, rhytides, psoriasis, malignant melanoma, seborrheic keratosis, seborrheic keratosis variants including e.g., dermatosis papulosis nigra, inverted follicular keratosis/keratoma warty dyskeratosis/warty dyskeratoma, acrokeratosis verruciformis, stucco keratosis; or a combination thereof.

As used herein, the term "stabilized hydrogen peroxide" refers to a hydrogen peroxide comprising a stabilizer or a blend of stabilizers useful for dilution of the hydrogen peroxide into a concentration that can be incorporated into a stable commercial formulation for topical application to skin lesions for the treatment of skin conditions described herein. In some embodiments, the hydrogen peroxide may be obtained from a commercial source. The amount and type of stabilizer(s) used in the hydrogen peroxide formulation may be proprietary to and/or a trade secret of the commercial source. In some embodiments, the stabilized hydrogen peroxide is a hydrogen peroxide of high concentration. Though pure hydrogen peroxides of high concentration are typically stable, stabilizers may be used in hydrogen peroxide formulations, usually when obtained through commercial sources, in order to stabilize diluted versions of the "high concentration" hydrogen peroxide formulation. Some hydrogen peroxide formulations have stabilizers in concentrations (in total and/or individually) sufficient to provide stabilization of diluted hydrogen peroxide for particular uses or in particular industries. In some embodiments, the stabilized hydrogen peroxide has been approved by the Food and Drug Administration (FDA) for topical administration to humans. In some embodiments, the stabilized hydrogen peroxide has a drug master file at the FDA and been approved by the FDA for topical administration to humans.

As used herein, the term "clinical efficacy" refers to the ability of an ingredient or composition to produce a desired effect. For example, in some embodiments, the desired effect may include, without limitation, decreasing the surface tension of the composition, increasing the wettability of the surface of the skin or skin lesion, increasing the permeability of the composition into the subject's skin, skin lesion, or surface imperfections, including crevices, invaginations and irregularities of the skin or skin lesion, decreasing the size of the target lesion, improving the shape and/or appearance of the target lesion, improving the target lesion or treated area and/or removing the target lesion, or a combination thereof.

The terms "therapeutically effective" or "effective", as used herein, may be used interchangeably and refer to an amount of a therapeutic composition of embodiments described herein. For example, a therapeutically effective amount of a composition is an amount of the composition, and particularly the active ingredient, such as hydrogen peroxide, that generally achieves the desired effect.

A "therapeutically effective amount" or "effective amount" of a composition is an amount necessary or sufficient to achieve the desired result. The activity contemplated by the embodiments herein includes medically therapeutic, cosmetically therapeutic and/or prophylactic treatment, as appropriate. The specific dose of a compound administered according to embodiments of the present invention to obtain therapeutic and/or prophylactic effects will, of course, be determined by the particular circumstances surrounding the case, including, for example, the compound administered, the route of administration, and the condition being treated. However, the effective amount administered can be determined by the practitioner or manufacturer or patient in light of the relevant circumstances including the condition to be treated, the choice of compound to be administered, and the chosen route of administration, and therefore, the above dosage ranges are not intended to limit the scope of the invention in any way. A therapeutically effective amount of the compound of embodiments herein is typically an amount such that when it is administered in a physiologically tolerable excipient composition, it is sufficient to achieve an effective systemic concentration or local concentration in or on the tissue to achieve the desired therapeutic or clinical outcome.

The terms "treat," "treated," or "treating" as used herein refers to therapeutic treatment, cosmetic treatment and/or prophylactic or preventative measures, wherein the object is to prevent or slow down (lessen) an undesired physiological condition, disorder or disease, or to obtain beneficial or desired clinical results. For the purposes of this disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects.

As used herein, the term "consists of" or "consisting of" means that the formulation or method includes only the elements, steps, or ingredients specifically recited in the particular claimed embodiment or claim.

As used herein, the term "consisting essentially of" or "consists essentially of" means that the formulation or method includes only the specified materials or steps and those that do not materially affect the basic and novel characteristics of the claimed invention.

Generally speaking, the term "tissue" refers to any aggregation of similarly specialized cells which are united in the performance of a particular function.

Seborrheic keratosis (SK) is one of the most common skin tumors in man. These benign epithelial skin tumors are most commonly seen in older individuals, increasing in prevalence with increasing age, and affect men and women roughly equally. The growths may be solitary or occur in large numbers and typically present as well demarcated, elevated or "stuck-on" appearing papules or plaques that may vary in color e.g., from flesh-colored, to shades of yellow, gray, brown, or black. Though benign, they are often cosmetically worrisome to patients, must sometimes be distinguished from other benign or malignant skin tumors, and may become symptomatic. They may be pruritic, irritated, bleed, and may be painful when traumatized particularly when located in areas prone to friction and trauma such as belt-lines and brassiere-strap lines.

Patients may seek treatment of SK for cosmetic reasons, especially if they are large, pigmented, and/or if multiple lesions are present, or simply because the lesions are commonly associated with advancing age. Removal may be medically indicated, however, for lesions that become irritated, pruritic, inflamed, or painful, or for lesions that the clinician feels require histologic confirmation of the diagnosis.

Numerous surgical treatment options for SK exist, and include a plethora of destructive/ablative modalities such as, e.g., liquid nitrogen cryotherapy, electrodesiccation, lasers of various wavelengths (ablative and non-ablative), radiofrequency ablation, dermabrasion, and surgical removal by curettage or surgical excision. There is, however, a notable lack of well-controlled clinical trials comparing the efficacy, complications and complication rates of these treatments. There is great variability among practitioners in the methods employed using each of these techniques (e.g., variability in contact time and method of freezing the lesions with liquid nitrogen) with great variability of the results. None of these treatments is, in fact, approved by the Food and Drug Administration (FDA) for the treatment of seborrheic keratosis. While these methods can achieve cure rates, many require specialized training and the use of expensive equipment, they are painful and may require anesthesia and/or analgesia, and they are often complicated by significant adverse cosmetic outcomes. Both hypopigmentation and hyperpigmentation, which may be transient, but often permanent, are common, as is scarring at the treatment site, and the typical post-surgical risks of bleeding and infection increase the risk that the result of the treatment of these lesions may be worse than the disease itself.

Numerous topical medical treatments for SK have been attempted, however no topical therapy has been found to be consistently effective. For example, ammonium lactate has been found to be ineffective. Other examples include calcipotriene ointment, tazarotene cream, imiquimod cream, and Vanicream® applied once daily for 16 weeks, all of which have been found to be ineffective. A single report of the off-label use of tazarotene 0.1% applied twice daily, reported efficacy in only 7/15 (47%) of subjects, and therapy was complicated by "burning, pruritus and redness". A report of the use of a topical vitamin $D_3$ ointment used once or twice daily for an average of 7.3 months (range 3-12 months) resulted in an 80% or more improvement in lesions in only 30% of patients. Thus there exists in the art a need for a safe and efficacious topical treatment for seborrheic keratosis.

Verrucae (Warts) are virally induced lesions caused by subtypes of the Cutaneous Human Papilloma Virus (HPV) family. HPV types are a subset of the large group of the DNA papillomavirus family that are capable of infecting humans and causing cutaneous lesions. HPV's are ubiquitous in the environment and infection occurs most commonly as a result of direct contact with individuals who harbor the virus either clinically (evidence lesions) or subclinically, indirectly through exposure to contaminated surfaces, or by autoinoculation of virus from individual lesions to adjacent uninfected skin. Cutaneous manifestations of HPV infection include common warts (verruca vulgaris), palmar and plantar warts, mosaic warts, flat warts, butcher's warts, and others. Subtypes of the HPV family are also etiologic of oropharyngeal, anogenital, laryngeal warts, papillomas, dysplasias (e.g., CIN (cervical intraepithelial neoplasia) carcinoma in situ, carcinomas, and in the skin lesions seen in epidermodysplasia verruciformis. Common warts are typically hyperkeratotic, exophytic dome-shaped papules or nodules (typically associated with HPV types 1, 2 or 4) and are most commonly located on the fingers (including periungual and subungual regions), dorsal surfaces of the hands, sites prone to trauma (e.g., knees, elbows), but may occur at virtually any other anatomical location. In some embodiments, the skin condition may be a benign neoplasm, premalignancy or malignancy. The skin condition may be an inflammatory condition. The skin condition may be a hyperproliferative condition. The skin condition may be ageing including intrinsic and extrinsic changes (e.g., photoaging (ultraviolet light induced changes)), pigmentary changes, fine lines and rhytides.

Condyloma acuminata, more commonly known as genital warts, are typically related to HPV types 6 and 11, 16, 18, and numerous other subtypes (e.g., 33, 35, 39, 40, 43, 45, 51-56, 58 and others), and multiple subtypes may exist in a single lesion. Condyloma acuminata typically present as solitary to multiple fleshy, soft, verrucoid papules that may be dome-shaped, filiform, fungating, "cauliflower-like", or form confluent plaques. They are typically located in the anogenital region (e.g., penis, vulva, vagina, cervix, perineum, and perianal regions), and may appear in the oropharynx, larynx and even tracheal mucosa, and rarely other cutaneous locations (e.g., trunk, extremities). The lesions are typically benign, but certain HPV subtypes are associated with a risk of malignant potential (e.g., HPV subtypes 16, 18) and may lead to cutaneous carcinomas or carcinomas-in-situ such as bowenoid papulosis or Buschke-Lowenstein tumor, and cervical dysplasias or neoplasia, e.g., cervical intraepithelial neoplasia (CIN).

In immunocompetent individuals, many common cutaneous lesions associated with HPV infection (e.g., warts and condylomata) spontaneously resolve in less than two years. However, warts can be large and/or cosmetically unsightly (e.g., face, hands), spread to distant anatomical regions by autoinoculation, painful (e.g., traumatized or on soles of feet), and untreated warts provide a significant reservoir of HPV infection in the community.

There are currently no specific antiviral therapies available to treat cutaneous HPV infection. Existing therapies are thus directed towards either the direct physical destruction of the lesions with locally destructive modalities such as cryotherapy, electrosurgery, curettage, laser therapy, application of acids (e.g., salicylic acid, trichloroacetic acid); locally cytotoxic therapies, such as topical podophyllin, cantharidin, or topical or intralesional 5-fluorouracil, or bleomycin; topical immunomodulatory therapy (e.g., topical imiquimod, intralesional candida antigen, topical squaric acid dibutyl ester, oral cimetidine) or surgical lesion removal. Various of these therapies are also available as over-the-counter (OTC) wart therapies in lower concentrations (e.g., topical salicylic acid preparations; home "freezing" kits). While these methods can achieve cure rates in some cases, many require multiple visits to a physician's office, specialized training and the use of expensive equipment; they are painful and may require anesthesia and/or analgesia, and they can be complicated by adverse cosmetic outcomes including scarring at the treatment site, and the typical post-surgical risks of bleeding and infection. No one therapy is consistently effective in all cases and in fact, there is great variability among practitioners in the methods employed using each of these techniques with great variability of the results. Recurrences are common and the use of multiple treatment modalities in combination is often necessary to achieve significant improvement. Thus, there exists a great unmet need in the art for a safe and efficacious topical treatment for the cutaneous lesions associated with HPV infection e.g., warts and condyloma.

Mollusca are virally induced lesions caused by subtypes of the DNA poxvirus family of molluscum contagiosum viruses (MCV). There are four subtypes of MCV, (MCV-1 to 4), with MCV-1 being the most prevalent and MCV-2 being most common in adults. Like HPV's, MCV's are ubiquitous in the environment and infection occurs most commonly as a result of direct contact with individuals who harbor the virus either clinically (evidence lesions) or subclinically, indirectly through exposure to contaminated surfaces, or by autoinoculation of virus from individual lesions to adjacent uninfected skin. The infection is most common in the pediatric population, sexually active adults, and the immunocompromised. Molluscum contagiosum lesions are typically flesh-colored, dome-shaped umbilicated ("dimpled") papules that may occur singly or in clusters and are typically located on the trunk groin or extremities, though may occur on any area of the skin. Individual lesions may spontaneously resolve in several weeks to several months, however, the natural history of the infection from appearance of the first lesions to resolution of the last lesion may last from six months to five years or more.

There are currently no U.S. Food and Drug Administration approved treatments for molluscum contagiosum. There are currently no specific antiviral therapies available to treat cutaneous MCV infection. Existing therapies are thus directed towards either the direct physical destruction of the lesions with locally destructive modalities such as cryotherapy, electrosurgery, curettage, laser therapy, unroofing the lesion with e.g., a needle ("needle-pricking"), application of acids or caustics (e.g., salicylic acid, potassium hydroxide); locally cytotoxic therapies, such as topical podophyllin, cantharidin; topical immunomodulatory therapy (e.g., topical imiquimod, intralesional candida antigen, nitric acid, oral cimetidine) or surgical lesion removal. While these methods can achieve cure rates in some cases, many require multiple visits to a physician's office, specialized training and the use of expensive equipment; they may be painful and may require anesthesia and/or analgesia, and may be anxiety producing and psychologically traumatic, particularly in the pediatric age group. These treatments may be complicated by adverse cosmetic outcomes including pigmentary changes (both hyperpigmentation and hypopigmentation), scarring at the treatment site, bleeding and infection. No one therapy is consistently effective in all cases and in fact, there is great variability among practitioners in the methods employed using each of these techniques with great variability of the results. The use of multiple treatment modalities including the treatment of underlying topical conditions such as atopic dermatitis, which tends to predispose to molluscum and the spread of the lesions, in combination is often necessary to achieve significant improvement. Thus, there exists a great unmet need in the art for a safe and efficacious (topical) treatment for the cutaneous lesions associated with MCV infection.

Hydrogen peroxide ($H_2O_2$) is a compound that is ubiquitous in the environment. It is the simplest peroxide and a potent oxidizing agent commonly used in innumerable household goods including chlorine-free bleaches, general-purpose cleaning products, and disinfectants, has been employed as the oxidizing component in hair dyes, and has been used in oral hygiene products and tooth-whitening systems for many years. In industry, it is employed in the treatment of wastewater and, in high concentrations, it is used in bleaching paper, pulp, and textiles. Clinically, in addition to its use as an oral topical agent noted above, hydrogen peroxide is widely employed at low concentrations (e.g., 3%-6%) as a wound irrigant and topical antiseptic/disinfectant, and has been in use medicinally since its introduction into clinical practice by Richardson in 1858.

Hydrogen peroxide is an important oxidizing agent in biological systems. The local deleterious effects of reactive oxygen species on the skin are mitigated by the presence of a complex antioxidant defense system that includes, enzymes such as catalase, glutathione peroxidase, superoxide dismutase, thioredoxin reductase, lipoamine, lipid peroxidase and others, as well as non-enzymatic components including ascorbic acid, urates and uric acid, tocopherol, glutathione, ubiquinones, ubiquinol and other water soluble groups. The local application of supra-physiologic concentrations of hydrogen peroxide may overwhelm the antioxidant defense systems in the skin, allowing hydrogen peroxide to act not only through its direct oxidation of organic tissues, generation of reactive oxygen species, and local lipid peroxidation, but also by the generation of local concentrations of oxygen that are toxic to the abnormal lesional (e.g., seborrheic keratosis, wart, condyloma acuminatum, molluscum contagiosum) cells.

It has been unexpectedly observed that both seborrheic keratosis lesions and common wart (verruca vulgaris) lesions evidenced a clinical response after the application of the compositions of embodiments herein. In certain cases, clearance of the cutaneous lesion was observed after one single treatment. In other cases, e.g., with thicker lesions or larger lesions, two or more treatments may be required for a clinical response. As exemplary benefits of this treatment method, the clinical response was brought about without the need for analgesia, without inducing pain, and without inducing the significant adverse events and adverse cosmetic outcomes commonly resulting from other therapies such as, e.g., pigmentary changes (such as hypopigmentation or hyperpigmentation), scarring at the treatment site, bleeding or infection.

Embodiments herein generally are directed to compositions comprising hydrogen peroxide and a surface tension modifying agent. In some embodiments, the surface tension modifying agent is an agent stable in compositions comprising concentrations of hydrogen peroxide disclosed in embodiments herein. In some embodiments, the surface tension modifying agent is in a quantity sufficient to enhance the therapeutic efficacy of the composition. In some embodiments, the surface tension modifying agent is in a quantity sufficient to enhance the therapeutic efficacy of the composition while maintaining stability of the composition. In some embodiments, the surface tension modifying agent is in a quantity sufficient to enhance the therapeutic efficacy of the composition while maintaining stability of the composition sufficient for use as a commercially viable formulation. In some embodiments, the surface tension modifying agent is an alcohol. Embodiments herein are directed to compositions comprising hydrogen peroxide and an alcohol. In some embodiments, the hydrogen peroxide may be a standard grade, food grade, chemical synthesis grade, semiconductor grade, high-test hydrogen peroxide grade, antimicrobial grade, drinking water grade, pharmaceutical grade or cosmetic grade hydrogen peroxide. In some embodiments, the alcohol may be selected from a primary alcohol, a secondary alcohol, a tertiary alcohol, or a combination thereof. In some embodiments, the alcohol may be selected from, but is not limited to, a low molecular weight alcohol, such as methanol, ethanol, butanol, 1-propanol, pentanol, hexanol, octanol, nonanol, decanol, 2-butanol, 2-propanol, 2-pentanol, benzyl alcohol, an isomer thereof, or a combination thereof. In some embodiments, the alcohol is not 1-propanol, ethanol, propanol, butanol, pentanol, hexanol, octanol, nonanol, decanol, 2-butanol, 2-pentanol, or benzyl alcohol. In some embodiments, the alcohol is 2-propanol (also referred to as isopropyl alcohol). In some embodiments, other volatiles such as, for example, acetates such as ethyl and butyl acetate (volatiles used in nail lacquers), cyclomethicone (a volatile silicone which may be included in an emulsifier system) may be used in combination with or in place of an alcohol. Embodiments herein also include a composition consisting essentially of hydrogen peroxide and an alcohol. Some embodiments are directed to a composition consisting of hydrogen peroxide and an alcohol. Some embodiments are directed to a composition comprising hydrogen peroxide and 2-propanol. Some embodiments are directed to a composition consisting essentially of hydrogen peroxide and 2-propanol. Some embodiments are directed to a composition consisting of hydrogen peroxide and 2-propanol.

In some embodiments, the hydrogen peroxide is in an amount of up to about 50% of the composition. In some embodiments, the composition comprises hydrogen peroxide in an amount of about 0.5% to about 99.9%, about 10% to about 99.9%, about 20% to about 99.9%, about 30% to about 99.9%, about 40% to about 99.9%, about 50% to about 99.9%, about 60% to about 99.9%, about 70% to about 99.9%, about 80% to about 99.9%, about 90% to about 99.9%, about 0.5% to about 70%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, about 50% to about 70%, about 55% to about 70%, about 60% to about 70%, about 65% to about 70%, up to about 50%, about 0.5% to about 50%, about 5% to about 50%, about 10% to about 50%, about 15% to about 50%, about 20% to about 50%, about 23.5% to about 50%, about 25% to about 50%, about 30% to about 50%, about 35% to about 50%, about 40% to about 50%, or about 45% to about 50%. In some embodiments, the hydrogen peroxide may be in an amount of about 0.5%, 5%, 10%, 15%, 20%, 23.5%, 25%, 30%, 32.5%, 35%, 40%, 45%, 50%, 55%, 60%, 65%, 70%, or a range between any two of these values.

In some embodiments, the hydrogen peroxide may be a stabilized hydrogen peroxide. In some embodiments, the hydrogen peroxide may be a standard grade, food grade, chemical synthesis grade, semiconductor grade, high-test hydrogen peroxide grade, antimicrobial grade, drinking water grade, pharmaceutical grade or cosmetic grade hydrogen peroxide. In some embodiments, the hydrogen peroxide may be a stabilized pharmaceutical grade hydrogen peroxide. In some embodiments, the hydrogen peroxide may be a stabilized cosmetic grade hydrogen peroxide. In some embodiments, the hydrogen peroxide is FMC/PeroxyChem "Super D" 50% cosmetic grade hydrogen peroxide. In some embodiments, the hydrogen peroxide is FMC/PeroxyChem's "High-Test Hydrogen Peroxide," which includes stabilized 50%, 70%, and 90% hydrogen peroxide. In some embodiments, the hydrogen peroxide is Arkema Peroxal 50 CG. In some embodiments, the starting hydrogen peroxide concentration is at a concentration sufficient to be diluted to a concentration of about 23% hydrogen peroxide or above in the compositions described herein. In some embodiments, the stabilized hydrogen peroxide has stabilizers in a concentration sufficient to prevent the breakdown/degradation of the hydrogen peroxide when it is diluted to a concentration of about 23% hydrogen peroxide or above in the compositions described herein. In some embodiments, the stabilized hydrogen peroxide has stabilizers in a concentration sufficient to prevent the breakdown/degradation of the surface-tension modifying agent (e.g., alcohol such as 2-propanol) when it is diluted to a concentration of about 23% hydrogen peroxide or above in the compositions described herein. In some embodiments, the stabilized hydrogen peroxide has stabilizers in a concentration sufficient to ensure the stability of the composition to be packaged in an appropriate packaging system, container, or applicator, and to be suitable for commercial use as contemplated in embodiments described herein. For example, in some embodiments, a method of making the composition may comprise a step or steps that the stabilized hydrogen peroxide be diluted down to, e.g., 45%, or 40% or 32.5%, or 25%, in the final composition. In this scenario, the starting hydrogen peroxide formulation should have a sufficiently high concentration to be able to be diluted to, e.g., 45%, or 40%, or 32.5%, or 25%, with the addition of water such as deionized water and an additional excipient or excipients such as a surface-tension modifying agent such as an alcohol (e.g., 2-propanol, or the like), as described in embodiments herein, such that it is sufficiently stabilized in order to guarantee a shelf-life suitable to produce a commercially viable formulation.

Hydrogen peroxide is a compound which is highly susceptible to decomposition by the presence of dissolved impurities, mostly transition metal cations and mixtures based on hydrogen peroxide may be unstable, with the hydrogen peroxide concentration diminishing over time due to catalytic decomposition. Impurities causing hydrogen peroxide decomposition are typically contained in water used to dilute the aqueous hydrogen peroxide stock formulation to a desired concentration or in the additional excipients added to the formulation (e.g., 2-propanol). A variety of factors may influence the stability of hydrogen peroxide in solutions, including, for example, the temperature, the concentration of hydrogen peroxide, the pH value, and the presence of impurities having a decomposing effect. To limit the influence of such decomposing factors on stability, it has been discovered that, in some embodiments, a stabilized composition having commercial value for the treatment of the multiple skin conditions described herein, e.g., seborrheic keratosis, warts, condyloma acuminatum, molluscum contagiosum, may be achieved by the careful selection of a concentration of 2-propanol and a stabilized (e.g., cosmetic grade) of high concentration (e.g., 50%) aqueous hydrogen peroxide solution. Accordingly, in some embodiments, the composition may comprise a stabilizer or combination of stabilizers. Hydrogen peroxide products from different sources may differ because of a proprietary blend of stabilizers unique to each company and to each product line within each company, and may importantly affect the stability and performance of the final product. Stabilizer levels for each individual stabilizer may vary from above 0 mg/ml to several thousand mg/l each depending on the grade of the hydrogen peroxide, the concentration of the peroxide, and the choice of stabilizers used. In some embodiments, the hydrogen peroxide is supplied by FMC Industrial Chemicals® (now PeroxyChem, LLC.), Sigma Corporation®, Arkema Incorporated®, or the like. In some embodiments, the hydrogen peroxide is supplied by PeroxyChem, LLC. In some embodiments, the hydrogen peroxide is FMC/PeroxyChem "Super D" 50% Cosmetic Grade hydrogen peroxide. Common stabilizers included in hydrogen peroxide formulations may include a stannate (e.g., colloidal stannate, sodium stannate), sodium pyrophosphate, organophosphonates, nitrate, phosphoric acid, colloidal silicate, any other stabilizer known in the art, or a combination thereof. In some embodiments, each stabilizer may be in a concentration of above 0 ppm to about 5000 ppm. In some embodiments, each stabilizer may be in a concentration of above 0 ppm to about 3000 ppm. In some embodiments, each stabilizer may be in a concentration of about 70 ppm to about 5000 ppm. In some embodiments, each stabilizer may be in a concentration of about 70 ppm to about 3000 ppm. In some embodiments, each stabilizer may be in a concentration of about 70 ppm to about 2700 ppm. In some embodiments, each stabilizer may be in a concentration of about 270 ppm to about 5000 ppm. In some embodiments, each stabilizer may be in a concentration of about 300 ppm to about 5000 ppm. In some embodiments, each stabilizer may be in a concentration of about 270 ppm to about 3000 ppm. In some embodiments, each stabilizer may be in a concentration of about 300 ppm to about 3000 ppm. In some embodiments, each stabilizer may be in a concentration of about 300 ppm to about 2700 ppm. In some embodiments, each stabilizer may be in a concentration of about 270 ppm to about 2700 ppm.

The hydrogen peroxide in compositions of embodiments herein may be replaced with or combined with other peroxides. Other peroxides may include, but are not limited to, sodium peroxide, potassium peroxide and potassium superoxide, lithium peroxide, barium peroxide, calcium peroxide, magnesium peroxide, zinc peroxide, tert-butyl hydroperoxide, peracetic acid, dibenzyl peroxide, benzoyl peroxide, lauroyl peroxide, or a combination thereof.

Water, organic solvents such as alcohols, surfactants, and other agents may alter the surface tension of compositions, formulations, and most particularly of solutions. However, little is known about the effects of low concentrations of alcohols or other volatiles on the wettability of normal skin when alcohol/water mixtures are applied, and there have been no reports on the effects of different concentrations of alcohols or other volatiles when incorporated into formulations comprising hydrogen peroxide on the wettability of normal skin or of the wettability of abnormal or lesional skin—such as skin that has been affected by seborrheic keratosis, warts, condyloma accuminatum, molluscum contagiosum, or other virally induced or non-virally induced cutaneous growths or lesions, including those skin conditions listed herein. Without being bound by theory, it is believed that the inclusion of alcohol in a stabilized peroxide solution may serve several important functions: The incorporation of a low concentration of the alcohol, e.g., less than 15% 2-propanol, may allow for the incorporation of a therapeutically effective concentration of hydrogen peroxide (e.g., 25% to 45% hydrogen peroxide), where the hydrogen peroxide may be in sufficient concentration to achieve the desired therapeutic effect on the cutaneous lesions, and the alcohol is in an amount sufficient to decrease the surface tension of the formulation and to increase the wettability of the surface of the skin lesion to allow spread of the formulation over the surface and into the surface irregularities of the lesion. However, secondary alcohols (e.g., isopropanol (IPA)) are expected to be inherently less stable in high concentrations of hydrogen peroxide than primary alcohols (see below), that is, 2-propanol is expected to be more readily oxidized in high concentrations of hydrogen peroxide than is 1-propanol, and the incorporation of low concentrations of a secondary alcohol (IPA) in a concentration sufficient to fulfill the above requirements (decrease surface tension/increase wettability of the skin lesion/maintain or enhance therapeutic efficacy) and allow the creation of a stable, commercially viable formulation was challenging.

It was surprisingly discovered that 2-propanol, in an amount that may be sufficient to decrease the surface tension of the formulation, may increase the wettability of the surface of the skin lesions, and may maintain or enhance the therapeutic effect of the formulation on the conditions that are the subject of this application, may be stably incorporated into a highly concentrated hydrogen peroxide solution. As noted above, isopropanol, a secondary alcohol, is expected to be more easily oxidized than 1-propanol, the primary alcohol in the presence of high concentrations of hydrogen peroxide. The mechanism of the oxidation of alcohols in high concentrations of hydrogen peroxide is first, the generation of hydroxyl radicals from the decomposition of the hydrogen peroxide. This process can be accelerated by the presence of catalytic metals or other catalysts such as those that might be introduced by the addition of excipients &/or impurities (mainly transition metal cations). The hydroxyl radical would then abstract a hydrogen atom from the carbon adjacent to the oxygen on the alcohol molecule, resulting in a carbon radical. In the case of isopropanol, this is a secondary radical which is stabilized by the electrons on the oxygen and both methyl groups next to the carbon. For 1-propanol, this is a primary radical with just one alkyl group next to it, which is less stable and more difficult to form. This intermediate would lose the hydrogen atom of the hydroxyl group to form ketone or aldehyde and the aldehyde, propanal from 1-propanol, can be further oxidized to propionic acid. In preparations of hydrogen peroxides that are of high purity and are highly stabilized or have high concentrations of stabilizers (and with lower concentrations of catalyst/impurities), the decomposition of peroxide may be slowed and thus the decomposition of the included alcohol may be slowed. Though without an obvious catalyst, the decomposition of peroxide is slow. The apparent reaction rate might be complex equation involving any trace catalyst (e.g., catalytic metal), peroxide and alcohol concentrations, but considering the alcohol alone, a secondary alcohol is more easily oxidized than the primary one. It was surprisingly discovered, however, that by employing a stabilized formulation of hydrogen peroxide (e.g., FMC/PeroxyChem "Super D"), the incorporation of low concentrations of the secondary alcohol 2-propanol (IPA) into a stable, commercially viable formulation, was indeed possible. Additionally and importantly, primary alcohols, such as 1-propanol are known to provoke cutaneous erythema (redness) and irritation of the skin and may produce a "flushing reaction" when applied to the skin due to the generation of aldehyde intermediates of primary alcohol breakdown. Alcohol dehydrogenase (ADH), which is present in the skin, acts on and breaks down primary alcohols, such as 1-propanol, but does not act on secondary alcohols, such as 2-propanol. Thus, only primary alcohols, which can be oxidized to the corresponding aldehydes by alcohol dehydrogenase (ADH) present in the skin, and not secondary (or tertiary) alcohols, elicit this cutaneous erythema reaction by this important mechanism. By incorporating a secondary alcohol such as 2-propanol (rather than a primary alcohol such as 1-propanol) into the composition, adverse cutaneous erythematous reactions resulting from or exacerbated by ADH catalyzed aldehyde intermediates may be avoided or mitigated.

It was thus surprisingly discovered that the addition of lower concentrations of alcohol, such as those described in embodiments herein, and particularly 2-propanol, to hydrogen peroxide increased the wettability of the skin lesion. Additionally, skin lesions, by nature, may have crevices and/or invaginations or surface irregularities that may make penetration of the hydrogen peroxide difficult. Accordingly, in some embodiments, a composition may comprise a hydrogen peroxide and a surface tension modifying agent. In some embodiments, the surface tension modifying agent may be an alcohol. The alcohol may be in an amount sufficient to decrease the surface tension of the composition to a level that effectively increases the penetration of the composition into such crevices and/or invaginations of the skin lesion, increase the surface area of reaction and increase the therapeutic efficacy and/or clinical response of the skin lesion to the therapeutic composition. In some embodiments, the composition further comprises another surface-tension modifying agent. In some embodiments, the surface tension modifying agent may be selected from, without limitation, a surfactant, e.g., an anionic or nonionic surfactant, a water-soluble surfactant such as a polysorbate, SLS (sodium lauryl sulfate), polypropylene glycol (PPG) stearate such as Arlamol, PEG (polyethylene glycol) stearate, steareth, ceteareth, polyoxyl stearate, or the like, or a combination thereof. The surface tension modifying agent may be in an amount sufficient to decrease the surface tension of the composition to a level that effectively increases the penetration of the composition into the crevices, invaginations and/or surface irregularities of the skin lesion, increases the surface area of reaction, and increases the therapeutic efficacy and/or clinical response of the skin lesion to the therapeutic composition, or a combination thereof.

In particular, it was surprisingly discovered that 2-propanol is a particularly effective alcohol for incorporation in the compositions described herein. In fact, it was unexpectedly discovered that 2-propoanol is a more suitable and effective alcohol in the compositions described herein than 1-propanol. 1-propanol does allow for release of hydrogen peroxide, may reduce the surface tension of the composition to increase penetration of the composition into the skin, and was expected to be more stable (i.e. less likely to be oxidized) in formulations comprising high concentrations of hydrogen peroxide. In fact, when compared to 2-propanol, 1-propanol does, in some concentrations, provide increased release or increased rate of release of hydrogen peroxide and may reduce surface tension more (on a weight to weight basis). However, it was surprisingly discovered that despite its seemingly potential desirable effects, 1-propanol is actually a less effective alcohol than 2-propoanol in compositions of embodiments disclosed herein. Without wishing to be bound by theory, it is believed that (i) though there is a trend towards 1-propanol containing compositions to release more hydrogen peroxide where 1-propanol is in higher concentrations, 2-propanol containing compositions effectively release hydrogen peroxide and exhibit a more constant rate of release across the desired concentrations in the embodiments described herein; (ii) though 1-propanol may reduce the surface tension of the hydrogen peroxide formulation more, on a weight for weight basis, than 2-propanol, the surface tension reduction induced in the compositions of the preferred embodiments by 1-propanol is excessive and suboptimal as it may induce such a great reduction that the composition would undesirably spread off the target lesion or area and onto surrounding non-lesional skin, leading to adverse effects such as irritation and erythema due at least in part to the generation of undesirable aldehyde intermediates as discussed above; and (iii) though theoretically, as discussed, the primary alcohol, 1-propanol, would be expected to exhibit greater stability in high concentration hydrogen peroxide formulations than the secondary alcohol (i.e. 2-propanol), 1-propanol appears to be oxidized to a greater degree by hydrogen peroxide in the high concentration hydrogen peroxide formulations of the preferred embodiments than is 2-propanol, and is, in fact, less stable. Thus, the incorporation of 2-propanol in compositions described herein provides for significant advantages over the incorporation of 1-propanol, including, but not limited to, providing for a therapeutically effective formulation which is more stable—leading to improved clinical efficacy of the composition, lower tendency to spread away from the intended site of application and, therefore, a more favorable safety profile The amount of alcohol in the composition may also be limited by the peroxide concentration in the formulation. For example, if a high concentration of peroxide is desired, the concentration of alcohol may necessarily be lowered in order to maintain the high concentration of peroxide in the formulation. In some embodiments, the alcohol may be in an amount sufficient to decrease the surface tension of the composition, to increase the penetration of the composition into the crevices and/or invaginations of the skin lesion, increase the surface area of reaction and increase the therapeutic efficacy and/or clinical response of the skin lesion to the therapeutic composition. In some embodiments, the formulation does not spread undesirably onto the surrounding non-lesional unaffected skin, which may occur with too large an amount of alcohol or too great a reduction in surface tension. In some embodiments the formulation does not irritate the surrounding, non-lesional, unaffected skin. In some embodiments, the formulation does not cause erythema to surrounding non-lesional unaffected skin. Erythema and irritation of the surrounding, non-lesional, unaffected skin may be caused by generation of irritating, erythema inducing intermediates, such as aldehydes, which may be due to the breakdown of suboptimal alcohols in the composition (e.g., primary alcohols, such as 1-propanol).

In some embodiments, the composition comprises a surface tension modifying agent. In some embodiments, the surface tension modifying agent is an alcohol. In some embodiments, the surface tension modifying agent is in an amount sufficient to decrease the surface tension of the hydrogen peroxide and water formulation. In some embodiments, the composition comprises an alcohol in an amount sufficient to decrease the surface tension of the hydrogen peroxide and water formulation. In some embodiments, the alcohol is a primary alcohol, a secondary alcohol, a tertiary alcohol, or a combination thereof. In some embodiments, the secondary alcohol is 2-propanol. Without alcohol, such as 2-propanol, to decrease the surface tension, the hydrogen peroxide-water formulation may sit on the surface of the lesion, without penetrating the lesion and/or the surface imperfections, irregularities, crevices of the lesion. In some embodiments, the surface tension modifying agent may be in an amount sufficient to decrease the surface tension of the composition to a level that effectively increases the penetration of the composition into such crevices and/or invaginations of the skin lesion, increase the surface area of reaction, increase the therapeutic efficacy and/or clinical response of the skin lesion to the therapeutic composition while minimizing irritation of the surrounding skin, or any combination thereof. Furthermore, alcohols that lower the surface tension of hydrogen peroxide composition excessively may run the risk of easily spreading off the application site and across non-lesional skin, causing less activity at the needed site and unwanted irritation and other adverse effects on the surrounding, unaffected skin.

In some embodiments, the alcohol in compositions of embodiments herein may be replaced with other volatile agents. Such volatile agents may include, but are not limited to, volatiles such as acetates, e.g., ethyl acetate and butyl acetate (volatiles used in nail lacquers), cyclomethicone (a volatile silicone which may be included in an emulsifier system), and various other volatiles in addition to those shown and described herein, which will become apparent to those skilled in the art from the foregoing description. Such additional volatile agents may be used in combination with or in place of an alcohol.

In some embodiments, the alcohol may be selected from a primary alcohol, a secondary alcohol, a tertiary alcohol, or a combination thereof. In some embodiments, the alcohol may include methanol, ethanol, butanol, 1-propanol, pentanol, hexanol, octanol, nonanol, decanol, 2-butanol, 2-propanol, 2-pentanol, benzyl alcohol, an isomer thereof or a combination thereof. In some embodiments, the alcohol is 2-propanol. Though embodiments herein may refer to 2-propanol in particular, one skilled in the art would understand that other alcohols and/or volatiles, such as, but not limited to, those described above may be used in place of 2-propanol in such embodiments.

2-propanol (also referred to as isopropyl alcohol) is a chemical compound with the molecular formula $C_3H_8O$ or $C_3H_7OH$. It is a colorless, flammable chemical compound with a strong odor. It is the simplest example of a secondary alcohol, where the alcohol carbon atom is attached to two other carbon atoms sometimes shown as $(CH_3)_2CHOH$. It is a structural isomer of propanol. 2-propanol is miscible in water, alcohol, ether and chloroform. It will dissolve ethyl cellulose, polyvinyl butyral, many oils, alkaloids, gums and natural resins. It is insoluble in salt solutions. Unlike ethanol or methanol, 2-propanol may be separated from aqueous solutions by adding a salt such as sodium chloride, sodium sulfate, or any of several other inorganic salts, since the alcohol is much less soluble in saline solutions than in salt-free water. 2-propanol has many medical and pharmaceutical uses and is typically used topically in concentrations of about 60% to about 70% in water as a topical disinfectant and in concentrations of about 60% to about 75% v/v solution in gels as a hand sanitizer. 2-propanol is also used as a water-drying aid for the treatment/prevention of otitis externa (swimmer's ear) in a concentration of up to 95%.

In some embodiments, the alcohol is in an amount of up to about 0.1%, up to about 0.25%, up to about 0.5%, up to about 1%, up to about 2%, up to about 2.5%, up to about 3%, up to about 4%, up to about 5%, up to about 8%, up to about 10%, up to about 14%, up to about 15%, up to about 20%, or up to about 25% of the composition. The use of low concentrations of alcohol, e.g., 2-propanol, as described in embodiments herein, allows for the use of stabilized hydrogen peroxides of therapeutically high concentrations (such as greater than 23%) of hydrogen peroxide, such that the stabilizers in the hydrogen peroxide are able to maintain the chemical stability of the formulation without being affected by the alcohol (and its impurities). In some embodiments, the alcohol may comprise up to about 25% of the composition. In some embodiments, the alcohol may be in an amount of about 0.05% to about 25%, about 0.5% to about 25%, about 1% to about 25%, about 2.5% to about 25%, about 5% to about 25%, about 10% to about 25%, about 15% to about 25%, or about 20% to about 25%, about 0.05% to about 15%, about 0.5% to about 25%, up to about 5%, about 0.01% to about 5%, about 0.1% to about 5%, about 0.5% to about 5%, about 1% to about 5%, about 1.5% to about 5%, about 2% to about 5%, about 2.5% to about 5%, about 3% to about 5%, about 3.5%, to about 5%, about 4% to about 5%, about 4.5% to about 5%, or the like. In some embodiments, the alcohol may be in an amount of about 0.01%, 0.1%, 0.25%, 0.5%, 0.75%, 1%, 2%, 2.5%, 3%, 4% 5%, 10%, 15%, 20%, 25%, or a range between any two of these values. In some embodiments, the composition comprises about 40% hydrogen peroxide and about 5% alcohol. In some embodiments, the composition comprises about 45% hydrogen peroxide and about 5% alcohol. In some embodiments, the composition comprises about 35% hydrogen peroxide and about 5% alcohol. In some embodiments, the composition comprises about 32.5% hydrogen peroxide and about 5% alcohol. In some embodiments, the composition comprises about 25% hydrogen peroxide and about 5% alcohol. In some embodiments, the composition comprises about 40% hydrogen peroxide and about 2.5% alcohol. In some embodiments, the composition comprises about 45% hydrogen peroxide and about 2.5% alcohol. In some embodiments, the composition comprises about 35% hydrogen peroxide and about 2.5% alcohol. In some embodiments, the composition comprises about 32.5% hydrogen peroxide and about 2.5% alcohol. In some embodiments, the composition comprises about 25% hydrogen peroxide and about 2.5% alcohol. In some embodiments, the composition comprises about 40% hydrogen peroxide and about 2% alcohol. In some embodiments, the composition comprises about 45% hydrogen peroxide and about 2% alcohol. In some embodiments, the composition comprises about 35% hydrogen peroxide and about 2% alcohol. In some embodiments, the composition comprises about 32.5% hydrogen peroxide and about 2% alcohol. In some embodiments, the composition comprises about 25% hydrogen peroxide and about 2% alcohol. In some embodiments, the alcohol is 2-propanol.

In some embodiments, the composition consists essentially of up to about 50% hydrogen peroxide and an alcohol. In some embodiments, the composition consists essentially of about 40% hydrogen peroxide and about 5% alcohol. In some embodiments, the composition consists essentially of about 45% hydrogen peroxide and about 5% alcohol. In some embodiments, the composition consists essentially of about 35% hydrogen peroxide and about 5% alcohol. In some embodiments, the composition consists essentially of about 32.5% hydrogen peroxide and about 5% alcohol. In some embodiments, the composition consists essentially of about 25% hydrogen peroxide and about 5% alcohol. In some embodiments, the composition consists of up to about 50% hydrogen peroxide and an alcohol. In some embodiments, the composition consists of about 40% hydrogen peroxide and about 5% alcohol. In some embodiments, the composition consists of about 45% hydrogen peroxide and about 5% alcohol. In some embodiments, the composition consists of about 35% hydrogen peroxide and about 5% alcohol. In some embodiments, the composition consists of about 32.5% hydrogen peroxide and about 5% alcohol. In some embodiments, the composition consists of about 25% hydrogen peroxide and about 5% alcohol. In some embodiments, the alcohol is 2-propanol.

In some embodiments, the alcohol decreases the surface tension of the composition. In some embodiments, the alcohol increases the penetration of the hydrogen peroxide into the skin imperfections of the subject, such as the irregularities, crevices and imperfections of the skin or skin lesion. In some embodiments, the alcohol defeats the subject's skin or skin lesion of the subject, thereby allowing better penetration of the hydrogen peroxide into the subject's skin or skin lesion. In some embodiments, the alcohol increases the wettability of the surface of the skin, including the wettability of the skin growth or lesion.

In some embodiments, the alcohol increases the effective concentration of the hydrogen peroxide when administered. Hydrogen peroxide is bactericidal, virucidal, sporocidal, and fungicidal, and may be a sterilant at varying concentrations and contact times. In some embodiments, the hydrogen peroxide is in a concentration sufficient to be virucidal. In some embodiments the hydrogen peroxide has sufficient contact time with the skin or skin lesion for it to exhibit its bactericidal, virucidal, sporocidal, fungicidal or sterilant effects. In some embodiments, the hydrogen peroxide has sufficient contact time with the skin or skin lesion sufficient for it to exhibit virucidal effects. Without being bound by theory, the alcohol may increase the effective concentration of the hydrogen peroxide when it evaporates after being administered, and may increase the oxidative and/or germicidal activity of the formulation. Additionally, the increased penetration of the formulation may increase the surface area or contact time of the solution with the skin or skin lesion and lead to enhanced effect as a germicide or sterilant.

In some embodiments, the composition may be administered topically. In some embodiments, the composition may be a solution. In some embodiments, the composition may be in a gel formulation. In some embodiments, the solution or gel formulation may be in two or more parts to be admixed at or immediately before the time of administration. In some embodiments, the composition may be in a cream, lotion, ointment, foam, transdermal patch, powder, solid, tape, paste or tincture. In some embodiments, the methods of treating described in embodiments herein require only one single application of the composition of embodiments herein. In some embodiments, the methods of treating described in embodiments herein require two or more applications of the composition of embodiments herein. In some embodiments, the methods of treating described in embodiments herein require multiple applications of the composition of embodiments herein.

In some embodiments, the composition may further include a pharmaceutically acceptable excipient. In some embodiments, the composition may further include an emollient, an emulsifier, a gelling agent, an additive, or a combination thereof. In some embodiments, the additive may be selected from preservatives, emulsion stabilizers, pH adjusters, chelating agents, viscosity modifiers, anti-oxidants, surfactants, detergents, emollients, opacifying agents, skin conditioners, buffers, or a combination thereof.

Some embodiments herein are directed to a gel formulation comprising hydrogen peroxide, and a gelling agent. In some embodiments, the gel formulation may further comprise an alcohol. In some embodiments, the gel formulation may further comprise a pharmaceutically acceptable excipient. In some embodiments, the gelling agent may be selected from Carbopol ETD 2020, Carbopol 980 NF, Carbopol 974P, Carbopol Ultrez 10, or the like. In some embodiments, the gelling agent may be high molecular weight, cross linked copolymers of acrylic acid and a hydrophobic comonomer or a copolymer (e.g., Pemulen TR-1); Polycarbophil AA-1; PVP (polyvinyl pyrrolidone); Eudragit; Poloxamer; Sepineo; Bentonite; Aerosil (silicates); Hyaluronic Acids; cross-linked Hyaluronic Acids; a combination thereof, or a compositional or chemical equivalent thereof possessive of the qualities required for the composition of embodiments described herein. In some embodiments, the gel composition is kept in two-parts and mixed at or immediately before the time of application. For example, the hydrogen peroxide and 2-propanol (first part) could be kept separate from the gelling agent (second part) until the time of administration or immediately before. As another example, the hydrogen peroxide, 2-propanol and gelling agent could each be separated into three parts and mixed at or immediately before the time of application. Additional parts may be possible for additional excipients or such excipients may be incorporated into existing parts. At or immediately before the time of administration, the multi-part gel formulation may be mixed and applied topically to the skin as a single gel formulation.

Some embodiments are directed to a gel formulation that may be delivered in an applicator that mixes two or more components of the gel formulation at or immediately before the time of application. In some embodiments, the gel formulation compartment applicator comprises at least one frangible compartment (e.g., gelling agent in the main compartment of the applicator, with the peroxide in a glass ampule within or alongside that compartment). Some exemplary applicators may include syringe-like applicators or "double-barrel" applicators that can freshly mix (e.g., "vortex mix") two or more components that need to be held in separate compartments for stability reasons, but which can be mixed at or immediately before the time of application.

In some embodiments, the composition further includes a buffer. In some embodiments, the buffer may be selected from triethanolamine, low pH buffers such as sodium acetate, citrate, phosphate, glycine, hydrogen chloride, citrate and phosphate, glycine and hydrogen chloride, the like, or a combination thereof. In some embodiments, the buffer may be present in an amount of about 0.001% to about 15%. In some embodiments, the buffer is present in an amount of about 0.001%, 0.01%, 0.05%, 0.1%, 0.5%, 1%, 5%, 10%, 15%, or a range between any two of these values. In some embodiments the buffer is present in any amount necessary to optimally adjust the pH of the composition.

In some embodiments, the composition has a surface tension of about 15 mN·m−1 to about 80 mN·m−1 at room temperature. In some embodiments, the composition has a surface tension of about 20 mN·m−1 to about 80 mN·m−1, about 30 mN·m−1 to about 80 mN·m−1, about 40 mN·m−1 to about 80 mN·m−1, about 50 mN·m−1 to about 80 mN·m−1, about 35 mN·m−1 to about 80 mN·m−1, about 35 mN·m−1 to about 70 mN·m−1, about 35 mN·m−1 to about 60 mN·m−1, about 35 mN·m−1 to about 50 mN·m−1 at 37° C., about 40 mN·m−1 to about 80 mN·m−1, about 40 mN·m−1 to about 70 mN·m−1, about 40 mN·m−1 to about 60 mN·m−1, about 40 mN·m−1 to about 50 mN·m−1, about 45 mN·m−1 to about 80 mN·m−1, about 45 mN·m−1 to about 70 mN·m−1, about 45 mN·m−1 to about 60 mN·m−1, or about 45 mN·m−1 to about 50 mN·m−1 at room temperature. In some embodiments, the composition has a surface tension of about 15 mN·m−1, about 20 mN·m−1, about 30 mN·m−1, about 36 mN·m−1, about 41 mN·m−1, about 48 mN·m−1, about 54 mN·m−1, about 75 mN·m−1, about 40 mN·m−1, about 50 mN·m−1, about 60 mN·m−1, about 70 mN·m−1, about 80 mN·m−1, or a range between any two of these values at room temperature. In some embodiments, the composition has a surface tension of about 42 mN·m−1 to about 55 mN·m−1 at room temperature. In some embodiments, the composition has a surface tension of about 42 mN·m−1 to about 50 mN·m−1 at room temperature.

In some embodiments, the composition has a surface tension of about 15 mN·m−1 to about 80 mN·m−1 at 37° C. In some embodiments, the composition has a surface tension of about 20 mN·m−1 to about 80 mN·m−1, about 30 mN·m−1 to about 80 mN·m−1, about 40 mN·m−1 to about 80 mN·m−1, about 50 mN·m−1 to about 80 mN·m−1, about 35 mN·m−1 to about 80 mN·m−1, about 35 mN·m−1 to about 70 mN·m−1, about 35 mN·m−1 to about 60 mN·m−1, about 35 mN·m−1 to about 50 mN·m−1 at 37° C., about 40 mN·m−1 to about 80 mN·m−1, about 40 mN·m−1 to about 70 mN·m−1, about 40 mN·m−1 to about 60 mN·m−1, about 40 mN·m−1 to about 50 mN·m−1, about 45 mN·m−1 to about 80 mN·m−1, about 45 mN·m−1 to about 70 mN·m−1, about 45 mN·m−1 to about 60 mN·m−1, or about 45 mN·m−1 to about 50 mN·m−1 at 37° C. In some embodiments, the composition has a surface tension of about 15 mN·m−1, about 20 mN·m−1, about 30 mN·m−1, about 36 mN·m−1, about 41 mN·m−1, about 48 mN·m−1, about 54 mN·m−1, about 75 mN·m−1, about 40 mN·m−1, about 50 mN·m−1, about 60 mN·m−1, about 70 mN·m−1, about 80 mN·m−1, or a range between any two of these values at 37° C. In some embodiments, the composition has a surface tension of about 42 mN·m−1 to about 55 mN·m−1 at 37° C. In some embodiments, the composition has a surface tension of about 42 mN·m−1 to about 50 mN·m−1 at 37° C.

In some embodiments, a composition comprising 40% hydrogen peroxide has a surface tension of from about 35 mN·m−1 to about 60.3 mN·m−1 at 37° C. In some embodiments, a composition comprising 40% hydrogen peroxide may have a surface tension of about 60.3 mN·m−1 at 37° C. A composition comprising 40% hydrogen peroxide and 2.5% 2-propanol may have a surface tension of about 54.1+/−0.8 mN·m−1 at 37° C. A composition comprising 40% hydrogen peroxide and 5% 2-propanol may have a surface tension of about 48.3+/−0.7 mN·m−1 at 37° C. A composition comprising 40% hydrogen peroxide and 10% 2-propanol may have a surface tension of about 41.1+/−0.6 mN·m−1 at 37° C. A composition comprising 40% hydrogen peroxide and 15% 2-propanol may have a surface tension of about 35.9+/−0.6 mN·m−1 at 37° C.

In some embodiments, the composition has a pH of about 1.5 to about 7.0. In some embodiments, the pH may be about 1.5 to about 3.5, about 1.5 to about 5.0, about 1.5 to about 4.0, about 1.7 to about 3.7, about 2.0 to about 5.0, about 2.0 to about 4.0, about 2.0 to about 2.8, about 2.5 to about 4.0, about 2.5 to about 4.5, about 2.5 to about 5.0, about 2.7 to about 3.83, about 2.7 to about 4.0, about 2.8 to about 4.0, about 2.83 to about 3.83, about 3.0 to about 7.0, about 4.0 to about 7.0, about 5.0 to about 7.0, or about 6.0 to about 7.0. In some embodiments, the pH may be about 1.5, 1.7, 2.0, 2.5, 2.7, 2.8, 2.83, 3.0, 3.3, 3.5, 3.7, 3.83, 4.0, 4.5, 5.0, 5.5, 6.0, 6.5, 7.0, or a range between any two of these values.

In some embodiments, the compositions of embodiments herein are stable for up to about four weeks at room temperature. In some embodiments, the compositions of embodiments herein are stable for up to about 15 minutes, about 30 minutes, about 1 hour, about 2 hours, about 3 hours, about 4 hours, about 5 hours, about 6 hours, up to about 12 hours, up to about 24 hours, up to about 1 week, up to about 2 weeks, up to about 3 weeks, up to about 1 month, up to about 6 weeks, up to about 2 months, up to about 3 months, up to about 4 months, up to about 6 months, up to about 8 months, up to about 10 months, up to about 12 months, up to about 18 months, up to about 2 years, up to about 2.5 years, or up to about 3 years at room temperature. In some embodiments, the compositions of embodiments herein are stable for up to about four weeks, up to about six weeks, up to about eight weeks, up to about three months, up to about 6 months, up to about 8 months, or up to about a year at 40° C. In some embodiments, the compositions of embodiments herein are stable for up to about four weeks, up to about 6 weeks, up to about 1 month, up to about 2 months, up to about 3 months, up to about 4 months, up to about 6 months, up to about 8 months, up to about 10 months, up to about 12 months, up to about 18 months, up to about 2 years, up to about 2.5 years, or up to about 3 years at 30° C. In some embodiments, the compositions of embodiments herein are stable for up to about four weeks, up to about 1 month, up to about 6 weeks, up to about 2 months, up to about 3 months, up to about 4 months, up to about 6 months, up to about 8 months, up to about 10 months, up to about 12 months, up to about 18 months, up to about 2 years, up to about 2.5 years, or up to about 3 years at 25° C. In some embodiments, the compositions of embodiments herein are stable for up to about four weeks, up to about 6 weeks, up to about 1 month, up to about 2 months, up to about 3 months, up to about 4 months, up to about 6 months, up to about 8 months, up to about 10 months, up to about 12 months, up to about 18 months, up to about 2 years, up to about 2.5 years, or up to about 3 years at 5° C.

In some embodiments, the compositions of embodiments herein satisfy the stability requirements put forth by the International Conference of Harmonisation of Technical Requirements for Registration of Pharmaceuticals for Human Use in the "ICH Harmonised Tripartite Guideline: Stability Testing of New Drug Substances and Products Q1A(R2)", current Step 4 version, dated 6 Feb. 2003, the entirety of which is incorporated herein by reference.

In some embodiments, the compositions of embodiments herein may also be administered in combination with other methods that mechanically, physically or chemically enhance the penetration of the active into the lesion. Such methods may include tape-stripping, destructive/ablative modalities such as, e.g., liquid nitrogen cryotherapy, electrodesiccation, lasers of various wavelengths (ablative and non-ablative), radio-frequency ablation, dermabrasion, and partial or complete surgical removal by curettage or surgical excision, use of an ablative or chemical peeling agent, or otherwise disturbing the surface of, or decreasing the thickness or size or overall volume of, or increasing the surface area of the lesion. In some embodiments, the compositions of embodiments herein may be administered in combination with other active ingredients, such as, for example, adjuvants, inhibitors, or other compatible drugs or compounds where such combination is seen to be desirable or advantageous in achieving the desired effects of the methods described herein. Any other known treatment may be used in combination with the formulation to treat the skin diseases disclosed herein. For example, the composition may be administered in combination with an active pharmaceutical agent that is used to treat the skin conditions described herein. In some embodiments, the compositions of embodiments herein may be administered before, concomitant with, or after the administration of another compound to treat the lesion. In some embodiments, the composition further comprises a topically active pharmaceutical agent used to treat the skin conditions described herein. As an example, a method of treating seborrheic keratosis may comprise administering ingenol mebutate to the subject and then administering the compositions of embodiments herein. As another example, a method of treating warts may comprise administering salicylic acid to the lesion of a person in need thereof in the morning and administering a composition of embodiments herein to the lesion of a person in need thereof in the evening. As another example, a method of treating warts, seborrheic keratosis, condyloma acuminate, mollusca, or acrochordons may comprise administering a topical retinoid to the lesion of a person in need thereof for a number of days and administering a composition of embodiments herein to the lesion of a person in need thereof after a number of days of pretreatment with the topical agent. Other possible examples will be readily apparent to one knowledgeable in the art. The other active or procedure may be administered or performed either before, after or concurrently with the compositions of embodiments herein.

Embodiments herein are also directed to a method of treating a skin condition comprising administering a composition of embodiments herein to a subject in need thereof. In some embodiments, the composition may be administered once daily, twice daily, weekly, biweekly, three times a week, every other day, monthly, every two months, every three months or as directed by the packaging or the physician to achieve the desired clinical result. The skin condition may be of infectious etiology. The skin condition may be a virally induced or non-virally induced cutaneous growth or proliferation. The skin condition may be a benign neoplasm, premalignancy or malignancy. The skin condition may be an inflammatory condition. The skin condition may be a hyperproliferative condition. The skin condition may be ageing including intrinsic and extrinsic changes (e.g., photoaging (ultraviolet light induced changes)), pigmentary changes, fine lines and rhytides. In some embodiments, the skin condition may be selected from Human Papilloma Virus induced lesions e.g., warts, common warts, recurrent warts, recalcitrant warts, treatment naïve warts, palmoplantar warts, flat warts, epidermodysplasia verruciformis related warts, anogenital warts, condyloma accuminatum, cervical dysplasias or neoplasias, e.g., cervical intraepithelial neoplasia (CIN); Herpesvirus related lesions including those induced by HHV-1 (HSV-1), HHV-2 (HSV-2), HHV-3 (varicella-zoster virus) e.g., chicken pox, Herpes zoster, shingles; Poxvirus induced lesions e.g., molluscum contagiosum, orf, callus, cutaneous horns, corns, acrochordons, fibroepithelial polyps, prurigo nodularis, actinic keratoses, squamous cell carcinoma, squamous cell carcinoma in situ, keratoacanthoma, basal cell carcinoma, cutaneous lymphomas and benign lymphocytic infiltrates & hyperplasias of the skin, clear cell acanthoma, large cell acanthoma, epidermolytic acanthoma, porokeratosis, hyperkeratosis, keratosis pilaris, lichenoid keratosis, acanthosis, acanthosis nigricans, confluent and reticulated papillomatosis, nevi, including e.g., dermal nevi, epidermal nevi, compound nevi, ILVEN (inflammatory linear verrucous epidermal nevi), nevus sebaceous, nevus comedonicus, and the like; acne, e.g., comedonal acne, inflammatory acne, papular acne, pustular acne, cystic acne; cysts, e.g., epidermoid cysts, milia, trichilemmal cysts, follicular cysts, proliferating cysts, dermoid cysts, pilonidal cysts, apocrine cysts, eccrine cysts, sebaceous cysts, mucous cysts, myxoid cysts, ganglion cysts, synovial cysts, vellus hair cysts, steatocystoma, hidrocystoma; adnexal neoplasms e.g., trichofolliculoma, fibrofolliculoma, perifollicular fibroma, trichodiscoma, nevus sebaceous, chondroid syringoma, trichoepithelioma, trichoblastoma, desmoplastic trichoepithelioma, pilomatricoma, pilomatrical carcinoma, tricholemmoma, trichelemmal carcinoma, tumor of the follicular infundibulum, tricoadenoma, proliferating pilar tumor, sebaceous hyperplasia, sebaceous adenoma, sebaceous epithelioma, sebaceous carcinoma, syringoma, poroma, hidradenoma, apocrine hidradenoma, spiradenoma, cylindroma, eccrine nevus (eccrine hamartoma), papillary adenoma, papillary adenocarcinoma; benign melanocytic proliferations or neoplasms e.g., ephilides, café-au-lait macules, Becker's melanosis, lentigines, solar lentigines, lentigo simplex, mucosal melanocytic lesions, Mongolian spots, Nevus of Ota, blue nevus, common acquired melanocytic nevi (nevocellular nevus, "moles"), congenital nevi, nevus spilus, recurrent nevi; vascular and perivascular neoplasms and reactive hyperplasias e.g., hemangiomas, cherry angiomas, hobnail hemangiomas (targeted hemosiderotic hemangiomas), tufted angiomas, hemangioendotheliomas, angiolymphoid hyperplasia with eosinophilia (ALHE), Glomus tumors (glomangiomas), hemangiopericytomas; cutaneous neural and neuroendocrine neoplasms e.g., neuromas, Schwannomas, neurofibromas, nerve sheath tumor, nerve sheath myxoma, neurothekeoma, granular cell tumor; fibrotic and fibrohistiocytic proliferations e.g., acrochordons, fibroepithelial polyps, fibromas, fibrous papules, angiofibromas, pearly penile papules, periungual fibromas, dermatofibromas, fibrokeratomas, sclerotic or pleomorphic fibromas, connective tissue nevi; cutaneous scars, hyperplasias, keloids, rosacea, cutaneous fungal, dermatophyte & mold infections, onychomycosis, hyperpigmentation, psoriasis, malignant melanoma, seborrheic keratosis, seborrheic keratosis variants including e.g., dermatosis papulosis nigra, inverted follicular keratosis/keratoma warty dyskeratosis/warty dyskeratoma, acrokeratosis verruciformis, stucco keratosis; or a combination thereof.

In some embodiments, the method of treating a skin condition further comprises the step of cleansing the treatment site before administration of the composition. In some embodiments, cleansing the treatment site comprises defatting the treatment site before the administration of the composition. In some embodiments cleansing the treatment site comprises applying at least 70% 2-propanol to the skin to be treated before administration of the composition. Defatting the treatment site may comprise applying the alcohol onto the skin, such as by rubbing, massaging, placing, scrubbing, abrading, wiping, swabbing, or otherwise contacting the skin with the alcohol.

In some embodiments, the method of treating a skin condition further comprises the step of debriding the treatment site of the subject. In some embodiments, debriding may include mechanically, chemically, or physically abrading, ablating, thinning, curetting, destroying, removing, excising, or otherwise disturb the surface of the skin or lesion to be treated, including decreasing the thickness of, and/or decreasing the volume of the lesion. In some embodiments, the step of debriding is before, after, and/or concurrent with administration of the compositions of embodiments herein to the treatment site.

In some embodiments, the alcohol may be selected from a primary alcohol, a secondary alcohol, a tertiary alcohol, or a combination thereof. The alcohol may be selected from methanol, ethanol, butanol, 1-propanol, pentanol, hexanol, octanol, nonanol, decanol, 2-butanol, 2-propanol, 2-pentanol, 2-hexanol, benzyl alcohol, an isomer thereof, or a combination thereof. In some embodiments, defatting the skin may comprise applying another known defatting agent to the skin such as ethyl acetate, butyl acetate, or the like onto the skin, such as by rubbing, massaging, placing, scrubbing, abrading, wiping, swabbing, or otherwise contacting the skin with the agent. In some embodiments, cleansing the skin comprises applying an antiseptic solution to the skin or skin lesion to be treated. In some embodiments, the antiseptic is povidone, iodine, chlorhexidine, a detergent, soap or the like.

Some embodiments are directed to a method of treating warts comprising administering a composition of embodiments herein to a subject in need thereof. In some embodiments, the composition comprises an alcohol and up to about 50% hydrogen peroxide. In some embodiments, warts may be treated using any of the methods of treatment described herein. Some embodiments are directed to a method of improving the appearance of warts comprising administering a composition of embodiments herein to a subject in need thereof. Some embodiments are directed to a method of improving the appearance of warts comprising administering a composition of embodiments herein to a subject in need thereof. Some embodiments are directed to a method of alleviating, e.g., shrinking, reducing in size, and/or reducing in height, a wart comprising administering a composition of embodiments herein to a subject in need thereof. In some embodiments, the warts are treatment naïve. In some embodiments, a treatment naïve wart may be treated using any of the methods of treatment described herein. Some embodiments are directed to a method of improving the appearance of treatment naïve warts comprising administering a composition of embodiments herein to a subject in need thereof. Some embodiments are directed to a method of improving the appearance of treatment naïve warts comprising administering a composition of embodiments herein to a subject in need thereof. Some embodiments are directed to a method of alleviating, e.g., shrinking, reducing in size, and/or reducing in height, a treatment naïve wart comprising administering a composition of embodiments herein to a subject in need thereof. In some embodiments, the warts are recalcitrant warts. Recalcitrant warts may include warts that are resistant to or have failed or have partially responded to other therapies, warts that are difficult to treat, or warts that are in anatomically difficult locations. In some embodiments, recalcitrant warts may include plantar warts, periungal warts, subungal warts or the like. In some embodiments, recalcitrant warts may be located on any body surface. In some embodiments, recalcitrant warts may be treated using any of the methods of treatment described herein. Some embodiments are directed to a method of improving the appearance of recalcitrant warts comprising administering a composition of embodiments herein to a subject in need thereof. Some embodiments are directed to a method of improving the appearance of recalcitrant warts comprising administering a composition of embodiments herein to a subject in need thereof. Some embodiments are directed to a method of alleviating, e.g., shrinking, reducing in size, and/or reducing in height, a recalcitrant wart comprising administering a composition of embodiments herein to a subject in need thereof. In some embodiments, the composition comprises about 25% hydrogen peroxide and 5% 2-propanol. In some embodiments, the composition comprises about 32.5% hydrogen peroxide and 5% 2-propanol. In some embodiments, the composition comprises about 40% hydrogen peroxide and 5% 2-propanol. In some embodiments, the composition comprises about 45% hydrogen peroxide and 5% 2-propanol. In some embodiments, the composition comprises up to about 50% hydrogen peroxide and 2-propanol.

Some embodiments are directed to a method of treating seborrheic keratosis comprising administering a composition of embodiments herein to a subject in need thereof. In some embodiments, the composition comprises an alcohol and up to about 50% hydrogen peroxide. In some embodiments, the composition comprises about 45% hydrogen peroxide and 5% 2-propanol. In some embodiments, the composition comprises about 40% hydrogen peroxide and 5% 2-propanol. In some embodiments, the composition comprises about 35% hydrogen peroxide and about 5% 2-propanol. In some embodiments, the composition comprises about 32.5% hydrogen peroxide and about 5% 2-propanol. In some embodiments, the composition comprises about 25% hydrogen peroxide and about 5% 2-propanol.

Some embodiments are directed to a method of treating acrochordons comprising administering a composition of embodiments herein to a subject in need thereof. In some embodiments, the composition comprises an alcohol and up to about 50% hydrogen peroxide. In some embodiments, the composition comprises about 45% hydrogen peroxide and 5% 2-propanol. In some embodiments, the composition comprises about 40% hydrogen peroxide and 5% 2-propanol. In some embodiments, the composition comprises about 35% hydrogen peroxide and about 5% 2-propanol. In some embodiments, the composition comprises about 32.5% hydrogen peroxide and about 5% 2-propanol. In some embodiments, the composition comprises about 25% hydrogen peroxide and about 5% 2-propanol.

Some embodiments herein are directed to a method of treating a skin condition comprising (i) topically administering a first dose of a composition comprising up to about 50% hydrogen peroxide and an alcohol; and (ii) topically administering one or more follow-up doses of the composition. In some embodiments, the application of the first dose and one or more follow-up doses comprises one application session. In some embodiments, the follow-up dose is administered immediately after administration of the first dose. In some embodiments, the follow-up dose is administered at least about 0.5 minutes after the first dose. In some embodiments, the follow-up dose is administered at least about 1 minute, at least about 1.5 minutes, at least about 2 minutes, at least about 5 minutes, at least about 10 minutes, at least about 15 minutes, at least about 20 minutes, at least about 25 minutes, at least about 30 minutes, or at least about 1 hour after the first dose. In some embodiments, there may be one follow-up dose, two follow-up doses, three follow-up doses, four follow-up doses, five follow-up doses, six follow-up doses, seven follow-up doses, eight follow-up doses, nine follow-up doses or ten follow-up doses in each application session. Each subsequent follow-up dose may be administered immediately after administration of the previous dose, at least about 1 minute, at least about 1.5 minutes, at least about 2 minutes, at least about 5 minutes, at least about 10 minutes, at least about 15 minutes, at least about 20 minutes, at least about 25 minutes, at least about 30 minutes or at least one hour after the previous dose.

In some embodiments, the topical composition may be administered in an effective dose. In some embodiments, an effective dose may be from about 0.0025 milliliters to about 3 milliliters of the compositions of embodiments herein, including about 0.0025 milliliters, about 0.01 milliliters, about 0.025 milliliters, about 0.05 milliliters, about 0.075 milliliters, about 0.1 milliliters, about 0.15 milliliters, about 0.5 milliliters, about 1 milliliters, about 1.5 milliliters, about 2 millimeters, about 2.5 milliliters, about 3 milliliters, a combination thereof, or any amount that has a clinical effect on the lesion. In some embodiments, the effective dose is proportional to size of the lesion. In some embodiments, the effective dose of the composition is less than about 0.1 milliliters per lesion. In some embodiments, an effective dose may be about 3 milliliters of the compositions of embodiments herein. In some embodiments, an effective dose may be from about 2 milliliters to about 3 milliliters of the compositions of embodiments herein. In some embodiments, an effective dose may be from about 2 milliliters to about 5 milliliters of the compositions of embodiments herein.

In some embodiments, topical administration of the first dose and the follow-up doses comprises massaging the composition into the skin for at least about 5 seconds, at least about 10 seconds, at least about 15 seconds, at least about 20 seconds, at least about 25 seconds, at least about 30 seconds, at least about 35 seconds, at least about 40 seconds, at least about 45 seconds, at least about 50 seconds, at least about 55 seconds, at least about 1 minute, at least about 2 minutes, at least about 3 minutes, at least about 4 minutes, or at least about 5 minutes, at least about 10 minutes, at least about 15 minutes, at least about 20 minutes at least about 25 minutes, or at least about 30 minutes during each dose. In some embodiments, the composition is a solution. In some embodiments, the composition is a gel. In some embodiments, massaging includes rubbing-in, manipulating, kneading, pressing, or otherwise "working" the composition into the skin. In some embodiments, the composition is applied and massaged into the skin with an applicator. In some embodiments, the composition is applied and massaged into the skin at least 1 time, at least 2 times, at least 3 times, at least 4 times, at least 5 times, at least 6 times, at least 7 times, at least 8 times, at least 9 times, or at least 10 times in each application session. In some embodiments, the application session, in which the composition is administered, may be repeated once daily, twice daily, weekly, biweekly, three times a week, every other day, monthly, every two months, every three months, every six months or as directed by the packaging or the physician to achieve the desired clinical result.

In some embodiments, the composition is administered by a health care provider. In some embodiments, the composition is administered in a health care setting. In some embodiments, the composition is self-administered by the subject in need thereof. In some embodiments, the composition is administered by a caregiver of the subject. As used herein, health care provider may include doctor, nurse, physician's assistant, nurse practitioner, medical assistant, or any professional working in a doctor's office, hospital or clinic. A health care setting, as used herein, refers to a doctor's office, hospital, ambulatory care setting, or clinic. A caregiver of the subject may include parents, nurse, friend, family member, medical professional, or anybody assisting in administering the composition to the subject in need thereof.

In some embodiments, the method further comprises topically administering a second composition comprising hydrogen peroxide and alcohol as described in embodiments above to the subject following an initial treatment by a health care provider. In some embodiments, the second composition is a take home composition. In some embodiments, the second composition is available over the counter. In some embodiments, the second composition is available by prescription. In some embodiments, the second composition may comprise a lower concentration of hydrogen peroxide than the initial treatment administered to the subject. In some embodiments, the second composition may comprise the same concentration of hydrogen peroxide as the initial treatment administered to the subject. In some embodiments, the second composition comprises up to about 50% hydrogen peroxide and an alcohol. In some embodiments, the second composition comprises about 45% hydrogen peroxide and 5% alcohol. In some embodiments, the second composition comprises about 40% hydrogen peroxide and 5% alcohol. In some embodiments, the second composition comprises about 35% hydrogen peroxide and 5% alcohol. In some embodiments, the second composition comprises about 32.5% hydrogen peroxide and 5% alcohol. In some embodiments, the second composition comprises about 25% hydrogen peroxide and 5% alcohol. In some embodiments, the alcohol is 2-propanol. In some embodiments, the second composition may be self-administered by the subject. In some embodiments, the second composition may be administered at least about 1 day, at least about 2 days, at least about 3 days, at least about 1 week, at least about 2 weeks, at least about 3 weeks, at least about 4 weeks, at least about 5 weeks, at least about 6 weeks, at least about 7 weeks or at an interval required to maintain the clinical effect or until the lesion is cleared, after the initial treatment by the healthcare professional. In some embodiments, the second composition may be administered once daily, twice daily, weekly, biweekly, every other day, monthly, every two months, every three months, every six months, or as directed by the packaging or the physician to achieve the clinically desired result.

Some embodiments herein are directed to a method of treating a skin condition in a subject comprising topically administering a take home composition comprising hydrogen peroxide and alcohol as described above to the subject. In some embodiments, the take home composition is available over the counter. In some embodiments, the take home composition is available by prescription. In some embodiments, the take home composition comprises about 50% hydrogen peroxide and an alcohol. In some embodiments, the take home composition comprises about 45% hydrogen peroxide and 5% alcohol. In some embodiments, the take home composition comprises about 40% hydrogen peroxide and 5% alcohol. In some embodiments, the take home composition comprises about 35% hydrogen peroxide and 5% alcohol. In some embodiments, the take home composition comprises about 32.5% hydrogen peroxide and 5% alcohol. In some embodiments, the take home composition comprises about 25% hydrogen peroxide and 5% alcohol. In some embodiments, the alcohol is 2-propanol. Such take home compositions may be administered following a visit to a healthcare professional. In some embodiments, the take home composition may be administered following an initial treatment by a healthcare professional. In some embodiments, the take home composition may comprise a lower concentration of hydrogen peroxide than the initial treatment administered to the subject. In some embodiments, the take home composition may comprise the same concentration of hydrogen peroxide as the initial treatment administered to the subject. The take home composition may be self-administered by the subject. In some embodiments, the take home composition may be administered at least about 1 day, at least about 2 days, at least about 3 days, at least about 1 week, at least about 2 weeks, at least about 3 weeks, at least about 4 weeks after the initial treatment by the healthcare professional. In some embodiments, the take home composition may be administered once daily, twice daily, weekly, biweekly, every other day, monthly, every two months, every three months, every six months, or as directed by the packaging or the physician to achieve the clinically desired result.

Embodiments herein also encompass devices for administering the hydrogen peroxide compositions of embodiments herein (see, for example, FIGS. 12-16 and associated description). In some embodiments, a composition comprising hydrogen peroxide and alcohol as described in embodiments herein may be administered using any topical applicator known in the art. In some embodiments, a composition comprising hydrogen peroxide and alcohol as described in embodiments herein may be administered using a sponge, a swab, a foam tipped stick, a cotton ball, a brush, a woven or non-woven fabric, roller, gauze, a pen, a glove, or the like. In some embodiments, the applicator may dispense compositions of embodiments herein via a tip that is flocked, absorbent, and/or firm enough to apply pressure to the lesion. In some embodiments the applicator is a sintered polymeric-tip applicator. In some embodiments, the applicator is resistant to, compatible with, or inert to high concentration peroxide solutions. In some embodiments, the applicator is capable of dispensing the solution at a controlled rate in order to help confine the active to the lesion of interest and spare surrounding normal skin. In some embodiments, the solution may be administered using a device having the hydrogen peroxide solution in a compartment that dispenses the solution onto or through an applicator tip when needed. In some embodiments, the applicator may comprise a material designed to abrade the skin lesion or treatment site before, after, or at the time of administration of the composition. In some embodiments, the applicator is a doe footed applicator. In some embodiments, the applicator is a flocked, doe footed applicator. In some embodiments, the flocked, doe footed applicator is comprised of HDPE (high density polyethylene), nylon, and an adhesive. In some embodiments, the solution is applied once daily, twice daily, weekly, biweekly, three times a week, every other day, monthly, every two months, every three months or as directed by the packaging or the physician or provider to achieve the desired clinical result.

In some embodiments, a method of treating a skin condition comprises administering the composition of embodiments herein. In some embodiments, administering the composition of embodiments herein comprises contacting a treatment site with a tip of an applicator, wherein the applicator comprises a frangible ampoule having the composition disposed therein, an applicator body having the frangible ampoule arranged therein, an applicator hub in fluid communication with the applicator body, the tip arranged at a proximal end of the applicator hub, and a filter arranged between the frangible ampoule and the tip. In some embodiments, administering the topical composition comprises controlling a flow rate of the topical composition out of the tip by varying a squeezing force applied to the exterior surface of the applicator body. In some embodiments, administering the topical composition comprises contacting the tip with a targeted lesion of the skin condition whereby the topical composition dispenses through the tip onto the targeted lesion. In some embodiments, administering the topical composition further comprises applying pressure to a pressure area arranged on an outer surface of the applicator body causing the frangible ampoule to rupture. In some embodiments, administering the topical composition comprises causing the frangible ampoule to rupture and release the topical composition through the tip; and contacting the tip to a targeted lesion of the skin condition.

Some embodiments herein are directed to a kit for the treatment of a skin condition comprising a container comprising a compartment having hydrogen peroxide, a compartment having 2-propanol and instructions for use. Some embodiments are directed to a kit for the treatment of a skin condition comprising a container comprising hydrogen peroxide and 2-propanol and instructions for use. In some embodiments, the kit further comprises an applicator. In some embodiments, the kit may include two or more applicators. For example, in some embodiments, a kit may contain many applicators where there is more than one lesion to treat (for example, in an over the counter kit or a kit for multiple administrations by the physician) or if the kit further includes a take home formulation of the composition for multiple applications. In some embodiments, the kit may comprise an applicator with a frangible glass ampoule having a solution of hydrogen peroxide and an alcohol. In some embodiments, the kit may comprise an applicator with a frangible glass ampoule having a solution of hydrogen peroxide, wherein the applicator also comprises a compartment having an alcohol, such as, without limitation, 2-propanol, in the applicator body. In some embodiments, the applicator may further include a compartment having a gelling agent. In some embodiments, the kit may comprise two or more containers of the topical hydrogen peroxide formulation. In some embodiments, the two or more containers of the topical hydrogen peroxide formulation may comprise hydrogen peroxide formulations of the same hydrogen peroxide concentration. In some embodiments, the two or more containers of the topical hydrogen peroxide formulation may comprise hydrogen peroxide formulations of different hydrogen peroxide concentrations. For example, in some embodiments, the kit may comprise one 40% hydrogen peroxide and 5% 2-propanol container for administration by the physician in the office, and other containers of different concentrations (e.g., weaker concentrations) of hydrogen peroxide for the patient to take home for subsequent applications to the target site. In some embodiments, a kit may include two or more single-use containers of the topical hydrogen peroxide formulation with multiple applicators. In some embodiments, a kit may include a container having multiple dose containers of the topical hydrogen peroxide formulation with multiple applicators. The skin condition may be a virally induced or non-virally induced cutaneous growth or proliferation. The skin condition may be a benign neoplasm, premalignancy or malignancy. The skin condition may be an inflammatory condition. The skin condition may be a hyperproliferative condition. The skin condition may be ageing including intrinsic and extrinsic changes (e.g., photoaging (ultraviolet light induced changes)), pigmentary changes, fine lines and rhytides. In some embodiments, the skin condition may be selected from Human Papilloma Virus induced lesions e.g., warts, common warts, palmoplantar warts, flat warts, recurrent warts, recalcitrant warts, treatment naïve warts, epidermodysplasia verruciformis related warts, anogenital warts, condyloma accuminatum, cervical dysplasias or neoplasias, e.g., cervical intraepithelial neoplasia (CIN); Herpesvirus related lesions including those induced by HHV-1 (HSV-1), HHV-2 (HSV-2), HHV-3 (varicella-zoster virus) e.g., chicken pox, Herpes zoster, shingles; Poxvirus induced lesions e.g., molluscum contagiosum, orf, callus, cutaneous horns, corns, acrochordons, fibroepithelial polyps, prurigo nodularis, actinic keratoses, squamous cell carcinoma, squamous cell carcinoma in situ, keratoacanthoma, basal cell carcinoma, cutaneous lymphomas and benign lymphocytic infiltrates & hyperplasias of the skin, clear cell acanthoma, large cell acanthoma, epidermolytic acanthoma, porokeratosis, hyperkeratosis, keratosis pilaris, lichenoid keratosis, acanthosis, acanthosis nigricans, confluent and reticulated papillomatosis, nevi, including e.g., dermal nevi, epidermal nevi, compound nevi, ILVEN (inflammatory linear verrucous epidermal nevi), nevus sebaceous, nevus comedonicus, and the like; acne, e.g., comedonal acne, inflammatory acne, papular acne, pustular acne, cystic acne; cysts, e.g., epidermoid cysts, milia, trichilemmal cysts, follicular cysts, proliferating cysts, dermoid cysts, pilonidal cysts, apocrine cysts, eccrine cysts, sebaceous cysts, mucous cysts, myxoid cysts, ganglion cysts, synovial cysts, vellus hair cysts, steatocystoma, hidrocystoma; adnexal neoplasms e.g., trichofolliculoma, fibrofolliculoma, perifollicular fibroma, trichodiscoma, nevus sebaceous, chondroid syringoma, trichoepithelioma, trichoblastoma, desmoplastic trichoepithelioma, pilomatricoma, pilomatrical carcinoma, tricholemmoma, trichelemmal carcinoma, tumor of the follicular infundibulum, tricoadenoma, proliferating pilar tumor, sebaceous hyperplasia, sebaceous adenoma, sebaceous epithelioma, sebaceous carcinoma, syringoma, poroma, hidradenoma, apocrine hidradenoma, spiradenoma, cylindroma, eccrine nevus (eccrine hamartoma), papillary adenoma, papillary adenocarcinoma; benign melanocytic proliferations or neoplasms e.g., ephilides, café-au-lait macules, Becker's melanosis, lentigines, solar lentigines, lentigo simplex, mucosal melanocytic lesions, Mongolian spots, Nevus of Ota, blue nevus, common acquired melanocytic nevi (nevocellular nevus, "moles"), congenital nevi, nevus spilus, recurrent nevi; vascular and perivascular neoplasms and reactive hyperplasias e.g., hemangiomas, cherry angiomas, hobnail hemangiomas (targeted hemosiderotic hemangiomas), tufted angiomas, hemangioendotheliomas, angiolymphoid hyperplasia with eosinophilia (ALHE), Glomus tumors (glomangiomas), hemangiopericytomas; cutaneous neural and neuroendocrine neoplasms e.g., neuromas, Schwannomas, neurofibromas, nerve sheath tumor, nerve sheath myxoma, neurothekeoma, granular cell tumor; fibrotic and fibrohistiocytic proliferations e.g., acrochordons, fibroepithelial polyps, fibromas, fibrous papules, angiofibromas, pearly penile papules, periungual fibromas, dermatofibromas, fibrokeratomas, sclerotic or pleomorphic fibromas, connective tissue nevi; cutaneous scars, hyperplasias, keloids, rosacea, cutaneous fungal, dermatophyte & mold infections, onychomycosis, hyperpigmentation, rhytides, psoriasis, malignant melanoma, seborrheic keratosis, seborrheic keratosis variants including e.g., dermatosis papulosis nigra, inverted follicular keratosis/keratoma warty dyskeratosis/warty dyskeratoma, acrokeratosis verruciformis, stucco keratosis; or a combination thereof. In some embodiments, the applicator may be selected from a sponge, a swab, a foam tipped stick, a cotton ball, a brush, a woven or non-woven fabric, roller, gauze, a pen, or the like. In some embodiments, the applicator is flocked, absorbent, and/or firm enough to apply pressure to the lesion. In some embodiments the applicator is a sintered polymeric-tip applicator. In some embodiments, the applicator is resistant to, compatible with, or inert to high concentration peroxide solutions. In some embodiments, the applicator is capable of dispensing the solution at a controlled rate in order to help confine the active to the lesion of interest and spare surrounding normal skin. In some embodiments, the solution may be administered using a device having the hydrogen peroxide solution in a compartment that dispenses the solution onto or through an applicator tip when needed. In some embodiments, the applicator may comprise a material designed to abrade the skin lesion or treatment site before or at the time of administration of the composition. In some embodiments, the applicator is a doe footed applicator. In some embodiments, the applicator is a flocked, doe footed applicator. In some embodiments, the flocked, doe footed applicator is comprised of HDPE (high density polyethylene), LDPE (low density polyethylene), Nylon, an adhesive, or any combination thereof. In some embodiments, the container may be selected from a vial, an ampule, a jar, a bottle, a medication tube, a syringe, or any other container for storing liquids. In some embodiments, the compartment may be selected from a vial, a tube, an ampoule, a jar, a bottle, a medication tube, a syringe, or any other container for storing liquids. In some embodiments the container may be glass, borosilicate glass, Type I borosilicate glass, tinted or otherwise light protected glass, amber tinted glass, amber Type I borosilicate glass, HDPE, Teflon®, silicone, ABS (acrylonitrilebutadiene stylene), or other compatible polymer or material. In some embodiments, the kit may include a glass vial or bottle having a solution of hydrogen peroxide and an alcohol disposed therein. In some embodiments the glass vial or bottle may include an amber glass vial or bottle. In some embodiments, the kit may comprise a vial or bottle at least partially formed from HDPE having a solution of hydrogen peroxide and an alcohol disposed therein. In some embodiments, the container may be formed from a material that has a low reactivity with peroxide. In some embodiments, the compartment may include a material that has a low reactivity with peroxide. In some embodiments, the hydrogen peroxide is a stabilized hydrogen peroxide. In some embodiments, the alcohol, such as, without limitation, 2-propanol, is in an amount of less than about 25%. In some embodiments, the kit may be for use by a health care provider. In some embodiments, the kit may be for use by the subject in need thereof. In some embodiments, the kit may be available only with a prescription. In some embodiments, the kit may be available over the counter for use by the subject in need thereof.

Figure 12:
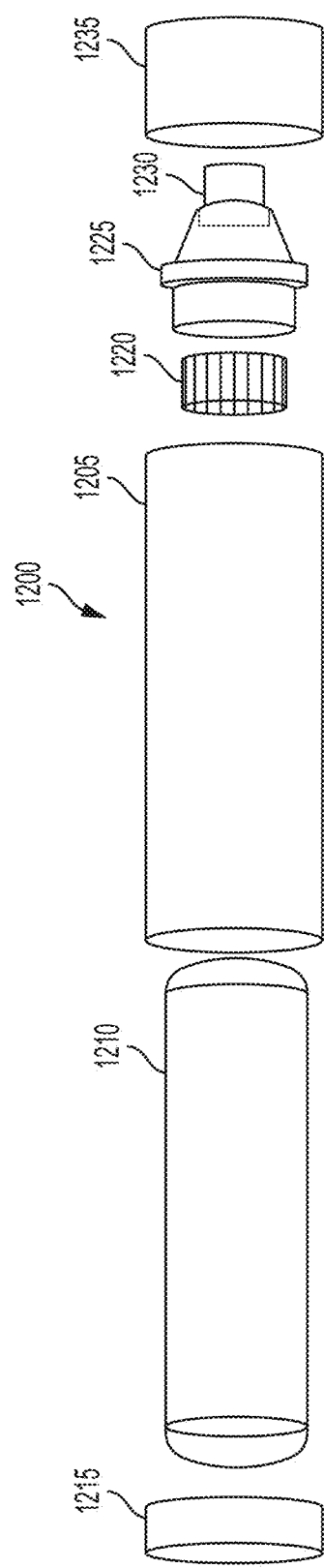
FIG. 12 depicts an illustrative applicator according to a first embodiment.

FIG. 12 depicts an illustrative applicator configured according to a first embodiment. As shown in FIG. 12, the applicator 1200 may include an applicator body 1205. In some embodiments, the applicator tube 1205 may be enclosed at a distal end thereof by an end cap 1215. In some embodiments, the applicator body 1205 and/or the end cap 1215 may be formed from various flexible materials, including, without limitation, flexible polymer materials. Non-limiting examples of flexible polymer materials may include polypropylene (PP), high-density polyethylene (HDPE) or low-density polyethylene (LDPE), polyvinyl chloride (PVC), polyethylene (PE), derivatives thereof, and any combination thereof. In some embodiments, the applicator body 1205 may have a generally longitudinal shape. In some embodiments, the applicator body 1205 may have a generally cylindrical shape. The applicator body 1205 may have various lengths according to some embodiments, including about 80 millimeters, about 90 millimeters, about 98 millimeters, about 99 millimeters, about 100 millimeters, about 110 millimeters, about 120 millimeters, about 130 millimeters, about 140 millimeters, about 150 millimeters, about 80 millimeters to about 100 millimeters, about 80 millimeters to about 150 millimeters, about 90 millimeters to about 100 millimeters, about 100 millimeters to about 120 millimeters, about 100 millimeters to about 150 millimeters, and any values or ranges between any of these values (including endpoints). The applicator body 1205 may have various outer dimensions according to some embodiments, including about 5 millimeters, about 7 millimeters, about 9 millimeters, about 10 millimeters, about 12 millimeters, about 15 millimeters, about 18 millimeters, about 20 millimeters, about 5 millimeters to about 7 millimeters, about 5 millimeters to about 10 millimeters, about 7 millimeters to about 10 millimeters, about 9 millimeters to about 15 millimeters, about 10 millimeters to about 15 millimeters, about 5 millimeters to about 20 millimeters, about 10 millimeters to about 20 millimeters, and any values or ranges between any of these values (including endpoints).

In some embodiments, an ampoule 1210 configured to store compositions of embodiments herein may be arranged within a cavity formed within the applicator body 1205. In some embodiments, the ampoule 1210 may be frangible, for example, configured to shatter, fragment, rupture, fracture, or otherwise break apart responsive to the application of sufficient pressure thereto. For instance, sufficient pressure may be applied manually, such as by applying a force by a human hand (for example, by squeezing or pressing) on the applicator body 1205 in a direction toward the ampoule 1210 in an area of the applicator body where the ampoule is located. In this manner, the force applied to the applicator body 1205 may be transferred to the ampoule 1210 and the ampoule may break apart responsive to the application of a sufficient force thereto. In some embodiments, the ampoule 1210 may be formed from various frangible materials, including glass, plastic, a polymer material, borosilicate glass, Type I borosilicate glass, tinted glass, and any combination thereof. In some embodiments, the ampoule 1210 may include one or more weakened regions to facilitate breakage of the ampoule 1210. In some embodiments, the compositions of embodiments herein may be caustic and/or may react with the materials of the applicator 1200 or the environment. In some embodiments, the compositions of embodiments herein may be degraded or otherwise effected by contaminants and/or contact with the environment. Accordingly, storage of compositions of embodiments herein using one or more ampoules 1210 may protect the applicator 1200 materials and/or the compositions of embodiments herein from being degraded until they are released from the ampoule. Through the use of the ampoules 1210, the applicator 1200 may, among other things, allow for the safe and stable storage of compositions of embodiments herein and other components until delivery is required.

The compositions of embodiments herein stored within the ampoule 1210 may be released within the applicator body 1205 responsive to the fracturing of the ampoule 1210. The ampoule 1210 may be configured to hold various volumes of the compositions of embodiments herein, including, about 0.1 milliliters, about 0.2 milliliters, about 0.5 milliliters, about 1 milliliters, about 1.5 milliliters, about 2 milliliters, about 2.4 milliliters, about 3 milliliters, about 3.2 milliliters, about 4 milliliters, about 5 milliliters, about 10 milliliters, about 20 milliliters, about 30 milliliters, about 50 milliliters, about 100 milliliters, about 500 milliliters, about 0.1 milliliters to about 3 milliliters, about 0.1 milliliters to about 4 milliliters, about 0.1 milliliters to about 5 milliliters, about 0.1 milliliters to about 10 milliliters, about 0.1 milliliters to about 100 milliliters, about 0.1 milliliters to about 500 milliliters, about 1 milliliters to about 3 milliliters, about 1 milliliters to about 4 milliliters, about 1 milliliters to about 5 milliliters, about 1 milliliters to about 100 milliliters, about 1 milliliters to about 500 milliliters, about 2 milliliters to about 3 milliliters, about 2 milliliters to about 4 milliliters, about 2 milliliters to about 5 milliliters, about 2 milliliters to about 10 milliliters, about 3 milliliters to about 4 milliliters, about 3 milliliters to about 5 milliliters, about 3 milliliters to about 10 milliliters, about 3 milliliters to about 100 milliliters, about 4 milliliters to about 5 milliliters, about 4 milliliters to about 10 milliliters, about 4 milliliters to about 100 milliliters, about 5 milliliters to about 10 milliliters, about 5 milliliters to about 100 milliliters, about 100 milliliters to about 500 milliliters, and any values or ranges between any of these values (including endpoints). In some embodiments, the ampoule 1210 may be configured to hold an effective dose of the compositions of embodiments herein. In some embodiments, the ampoule 1210 may be configured to hold an effective dose of the compositions of embodiments herein sufficient to treat a single target lesion or skin area. In some embodiments, the ampoule 1210 may be configured to hold an effective dose of the compositions of embodiments herein sufficient to treat multiple target lesions or skin areas. In some embodiments, an effective dose may be from about 0.0025 milliliters to about 3 milliliters of the compositions of embodiments herein, including about 0.0025 milliliters, about 0.01 milliliters, about 0.025 milliliters, about 0.05 milliliters, about 0.075 milliliters, about 0.1 milliliters, about 0.15 milliliters, about 0.5 milliliters, about 1 milliliters, about 1.5 milliliters, about 2 millimeters, about 2.5 milliliters, about 3 milliliters, a combination thereof, or any amount that has a clinical effect on the lesion. In some embodiments, the effective dose is proportional to size of the lesion. In some embodiments, the effective dose of the composition is less than about 0.1 milliliters per lesion. In some embodiments, an effective dose may be about 3 milliliters of the compositions of embodiments herein. In some embodiments, an effective dose may be from about 2 milliliters to about 3 milliliters of the compositions of embodiments herein. In some embodiments, an effective dose may be from about 2 milliliters to about 5 milliliters of the compositions of embodiments herein.

Although only one ampoule 1210 is depicted in FIG. 12, embodiments are not so limited, as the applicator 1200 may include a plurality of ampoules. For instance, an applicator 1200 may include multiple ampoules 1210 for multiple doses of the compositions of embodiments herein. In another instance, an applicator 1200 may include a plurality of ampoules 1210 housing different compositions. In some embodiments, the applicator 1200 may include a compartment (not shown) housing a first composition (e.g., a gelling agent, hydrogen peroxide) and one or more ampoules 1210 housing one or more second compositions (e.g., 2-propanol, compositions of embodiments herein). For example, one or more walls may partition the applicator body into one or more compartment portions. In some embodiments, a compartment or a portion thereof (e.g., a wall portion forming the compartment within the applicator body 1205) may be fractured by the application of sufficient force to the compartment. In some embodiments, one or more first compositions may be disposed within the applicator body 1205 such that one or more second compositions disposed within the one or more ampoules 1210 and/or one or more compartments may contact the one or more second compositions responsive to the release of the one or more second compositions. A non-limiting example of a first composition may include an alcohol (e.g., 2-propanol) or a gelling agent and a non-limiting example of a second composition may include a caustic formulation, such as a hydrogen peroxide solution. In some embodiments, the various compositions (e.g., the one or more first compositions and the one or more second compositions) may be mixed together before or concurrently with the application thereof.

In some embodiments, an applicator hub 1225 may be in fluid communication with the applicator body 1205 at a proximal end of the applicator 1200. The applicator hub 1225 may be configured to receive the compositions of embodiments herein that flow from the applicator body 1205 responsive to the release of the compositions of embodiments herein from the ampoule 1210. In some embodiments, at least a portion of the applicator hub 1225 may be arranged within the applicator body 1205. In some embodiments, the applicator hub 1225 may be fixedly attached to the applicator body 1205, such as through the use of adhesives, a friction fit, a press-fit, a threaded fit, or the like. In some embodiments, an outer portion of the applicator hub 1225 may be fixedly attached to an inner portion of the proximal end of the applicator body 1205. In some embodiments, the applicator hub 1225 may form a hermetic seal with the applicator body 1205 through a friction fit, adhesives, a threaded fit, or the like. In some embodiments, the applicator hub 1225 may be formed from a polymer material, including, without limitation, PE, PP, HDPE, and LDPE. In some embodiments, a protective cap 1235 may be configured to enclose the applicator hub 1225 at a proximal end of the applicator 1200.

In some embodiments, a filter 1220 may be arranged within the applicator 1200 between the ampoule 1210 and the proximal end of the applicator 1200. In some embodiments, the filter 1220 may be arranged within a distal portion of the applicator hub 1225 that faces the ampoule 1210. The filter 1220 may be configured to filter out pieces of the broken ampoule 1210 while allowing the compositions of embodiments herein to flow therethrough. The filter 1220 may be formed from various materials, including any material capable of filtering out the shards of the ampoule from the compositions of embodiments herein. Non-limiting examples of filter 1220 materials may include various polymer materials, PE, PP, HDPE, LDPE, polystyrene (PS), carbon, a foam material, ceramic, sand, diatomaceous earth (DE), paper fibers, and any combination thereof. In some embodiments, the filter 1220 material may be selected to provide a particular flow rate of the compositions of embodiments herein through the filter.

In some embodiments, the applicator 1200 may include a tip 1230 arranged at a proximal portion thereof. In some embodiments, the tip 1230 may be fixedly arranged within a central bore of the applicator hub 1225. The tip 1230 may be configured to facilitate the application of the compositions of embodiments herein onto the skin of a patient. In some embodiments, the tip 1230 may be formed from an absorbent or substantially absorbent material. In some embodiments, the tip 1230 may be configured as a sintered polymeric tip. In some embodiments, the tip 1230 may be configured as a doe footed tip. In some embodiments, the tip 1230 may be configured as a flocked tip, for example, that may include and/or may be formed from a flocked material, including, without limitation flock formed from filaments of various materials. In some embodiments, the flocked tip may be formed by affixing a flocked material to the tip 1230. In some embodiments, the tip 1230 may be formed from various materials that are non-reactive or otherwise chemically compatible with the compositions of embodiments herein. In some embodiments, the tip 1230 may be formed from various biocompatible materials. In some embodiments, the tip 1230 may be formed from various materials, including, without limitation, cellulose, nylon, rayon, polyester, Teflon®, fibers thereof, flocked materials thereof, and any combination thereof.

In some embodiments, the tip 1230 may be fixedly arranged within the applicator 1200, such as in the applicator hub 1225, such as through adhesives, a friction fit, a threaded fit, a snap or lock fit, a press-fit, or the like. In some embodiments, the applicator 1200 may be configured to allow replacement of the tip 1230 during or after each use. In some embodiments, the ampoule 1210 may be replaced within the applicator 1200. For instance, an operator may remove the end cap 1215, remove the shards of a fractured ampoule 1210, and insert a new ampoule with the same and/or different compositions of embodiments herein. In this manner, the applicator 1200 may be used multiple times and/or for the treatment of multiple skin conditions (i.e., separate lesions, warts, or other skin formations) of the same patient. In some embodiments, the applicator 1200 may be a single use applicator. In some embodiments, the single use applicator is intended to be discarded after a single use.

In some embodiments, the compositions of embodiments herein may be released from the ampoule 1210 and flow through the applicator body 1205 (including any chambers thereof), the filter 1220, the applicator hub 1225, and out of the applicator through the tip 1230. In some embodiments, the applicator body 1205 and/or the tip 1230 may be configured to allow an operator to control the flow of the caustic formulation out of the applicator 1200. In a non-limiting example, after the compositions of embodiments herein have been released from the ampoule 1210, an operator may initiate flow of the compositions of embodiments herein out of the applicator 1200 by squeezing on the applicator body 1205, thereby generating sufficient pressure therein to force the compositions of embodiments herein to flow out through the tip 1230. In some embodiments, pressing the tip 1230 on the skin of a patient may produce capillary action sufficient to cause the compositions of embodiments herein that have been released from the ampoule 1210 and are in contact with the tip to flow through the tip and out of the applicator 1200. In some embodiments, an operator may control the rate of the flow by varying a level of force used to squeeze the sides of the applicator body 1205 and/or press the tip 1230 against the skin of the patient. In some embodiments, the applicator 1200 may include an actuator (not shown) configured to cause the compositions of embodiments herein to be dispensed from the applicator.

In some embodiments, at least one portion of the applicator may include a hydrophobic material, such as the filter 1220 and/or the tip 1230. In some embodiments the hydrophobic material is composed of polyester or co-polyester polymers, acrylic, modified acrylic (e.g., modacrylic), polypropylene, polyethylene or combinations or mixtures thereof. In some embodiments, for example, the filter may comprise a blend of polypropylene and polyester or co-polyester polymers. Non-limiting examples of hydrophobic materials may also include materials including, coated with, and/or modified by silanes, alkylsilanes, fluoroalkylsilanes, silicone, combinations thereof, and derivatives thereof. In some embodiments, materials used to form the applicator and portions thereof according to some embodiments described herein may be imparted with hydrophobic properties by coating or otherwise incorporating a hydrophobic material therein. In some embodiments, the hydrophobic portions of the applicator may operate to impede, reduce, prevent, and/or substantially prevent the compositions of embodiments herein that have been released from the ampoule from flowing through portions of the applicator and/or out of the tip of the applicator.

In some embodiments, the applicator 1200 may be configured such that the compositions of embodiments herein released from the ampoule 1210 may not be passively dispensed from the applicator 1200 without an operator applying pressure to the applicator, such as by squeezing or otherwise applying a force to the applicator body 1205. In some embodiments, the requirement for operator action (i.e., applying pressure to the applicator 1200) may be facilitated by the use of hydrophobic materials according to some embodiments. In some embodiments, the applicator 1200 may be configured such that a void may be formed within the applicator body 1205 behind a volume of the compositions of embodiments herein released from the ampoule 1210, for instance, when the applicator is orientated in a vertical, substantially vertical, or partially vertical position. In some embodiments, the void may operate as a vacuum to impede, reduce, restrict, prevent, and/or substantially prevent the flow of the compositions of embodiments herein released from the ampoule 1210 out of the applicator 1200. In this manner, the hydrophobic portion of the applicator 1200 and/or a void formed within the applicator body 1205 may operate to prevent the leakage of the compositions of embodiments herein from the applicator after the compositions of embodiments herein have been released from the frangible ampoule 1210, including when the applicator is in a position conducive to dispensing compositions of embodiments herein, such as a vertical or substantially vertical position.

The applicator 1200 may be configured to store, dispense, and apply any of the compositions of embodiments herein as part of a method of treatment for any of the conditions disclosed herein. For example, the applicator 1200 may be configured to store, dispense, and apply a topical composition comprising 2-propanol and up to about 50% hydrogen peroxide. In some embodiments, the topical composition may be any composition described in embodiments herein.

FIGS. 13A-13C depict a first exploded side view, a second exploded side view, and a cross-sectional view, respectively, of an illustrative applicator according to a second embodiment. As shown in FIGS. 13A-13C, an applicator 1300 may include an applicator body 1305 having an ampoule 1310 arranged within an interior cavity thereof. A proximal end of the applicator body 1305 may be enclosed by a protective cap 1325, for example, when the applicator 1300 is not in use. A distal end of the applicator body 1305 may be enclosed by an end cap 1315 fixedly attached thereto, such as through adhesives, a friction fit, a snap or lock connection, or the like. A holed flocked tip 1330 (may be arranged within at least a portion of the applicator body 1305 at a proximal end thereof. In some embodiments, the holed flocked tip 1330 may be formed from or substantially from applicator hub 1225 and tip 1230 as depicted in FIG. 12. In some embodiments, the holed flocked tip 1330 may be fixedly attached to the applicator body 1330, such as through adhesives, a friction fit, a threaded fit, a snap or lock fit, or the like. In some embodiments, a filter 1335 may be arranged within the holed flocked tip 1330.

In some embodiments, a grip 1320 may be arranged on an exterior portion of the applicator body 1305 at a proximal end thereof. In some embodiments, the grip 1320 may be configured to improve the ability of the hand of an operator to hold and control the applicator 1300. In some embodiments, the grip 1320 may be formed from various polymer materials, including, without limitation, a foam material, a rubber material, a plastic material, a thermoplastic material, or other material known to those having ordinary skill in the art, or any combination thereof. In some embodiments, the grip 1320 may be configured to facilitate enhanced hand positioning, increased operator comfort, decreased hand fatigue, or the like, when using the applicator 1300. In some embodiments, at least a portion of the grip 1320 may include a contoured, curved, concave, or other non-flat surface configured to facilitate precise control of the applicator 1300 by an operator. In some embodiments, the grip 1320 may include at least one anti-roll feature configured to reduce or prevent the rolling or turning of the applicator 1300 in the hand of an operator during use thereof. In some embodiments, the grip 1320 may include at least one anti-roll feature configured to reduce or prevent the rolling or turning of the applicator 1300 when placed on a surface, for example, a counter, a table, an instrument stand, or the like. In some embodiments, the grip 1320 may be over-molded onto the exterior surface of the applicator body 1305. In some embodiments, the grip 1320 may be configured as a separate element that may be slid on to, or otherwise adjoined to or affixed to, the applicator 1300.

In some embodiments, a pressure area 1345 may be arranged on the applicator body 1305. In some embodiments, the pressure area 1345 may include a marked area configured to indicate to an operator an optimum area on the applicator tube 1305 to apply pressure to fracture the ampoule 1310. In some embodiments, the pressure area 1345 may be configured to receive the fingers and/or thumb of a user to facilitate the grip of and/or the squeezing of the applicator tube 1305 to rupture the ampoule 1310. In some embodiments, the pressure area 1345 may include a marked area formed from one or more raised formations. In some embodiments, the pressure area 1345 may be formed from materials that are molded onto an outside surface of the applicator body 1305. In some embodiments, the pressure area 1345 may include a printed and/or raised feature arranged on a label affixed to an outer surface of the applicator body 1305. In some embodiments, the pressure area 1345 may be configured to concentrate pressure applied by an operator to rupture the ampoule 1310. In some embodiments, the pressure area 1345 may be configured to indicate a position directly or substantially directly above one or more force concentration elements (not shown) located within the applicator body 1305 that are configured to concentrate pressure applied by an operator to rupture the ampoule 1310. In some embodiments, the force concentration elements may include one or more struts formed from various materials, such as a plastic material. In some embodiments, the force concentration elements are not present in the applicator 1300. In some embodiments, finger pressure is sufficient to rupture the ampoule 1310. In some embodiments, the pressure area 1345 may be formed from a more flexible material than the other portions of the applicator tube 1305 to facilitate the transfer of pressure from the hand of an operator squeezing on the applicator tube 1305 to the ampoule 1310. In an embodiment in which the applicator 1300 includes a plurality of ampoules 1310 and/or one or more compartments (not shown), the applicator may include a plurality of pressure areas 1345 configured to indicate an optimum area to apply pressure to fracture each compartment and/or ampoule.

In some embodiments, the ampoule 1310 may be fixedly arranged within the applicator body 1305. For example, in some embodiments, the ampoule may be fixedly arranged within the applicator body 1305 such that the ampoule does not does not move or substantially does not move longitudinally within the applicator body 1305 or does not move proximally beyond a certain position within the applicator body. In some embodiments, the size and/or shape of the ampoule 1310 may be configured to correspond with the size and/or shape of the applicator body 1305 (for instance, an inner dimension of the applicator body) such that the applicator body holds the ampoule in place therein through a friction fit. In some embodiments, the applicator body 1305 may include a varying inner dimension such that the ampoule 1310 may only fit within a certain portion of the applicator body. In some embodiments, the inner surface of the applicator body 1305 may include bumps, ridges, projections, or other structures configured to hold the ampoule 1310 in place and/or to prevent the ampoule from moving longitudinally within the applicator body. In some embodiments, a support structure 1340 may be arranged within the applicator body to hold the ampoule 1310 in place and/or to prevent the ampoule from moving longitudinally within the applicator body 1305. In some embodiments, the support structure 1340 may include one or more struts or projections (e.g., ridges, bumps, or the like) arranged within and/or formed from portions of the applicator body 1305. In some embodiments, the support structure 1340 may be configured to position the ampoule for breakage by an operator. For example, the support structure 1340 may be configured to maintain the within an area corresponding with the pressure area 1345.

In some embodiments, the applicator 1300 may include one or more debriding elements (not shown) arranged on an exterior portion of the applicator, such as the applicator body 1305, the end cap 1315, and/or the protective cap 1325. The one or more debriding elements may be configured to mechanically or physically abrade, ablate, thin, curette, destruct, remove, excise, or otherwise debride an area of skin of a patient, such as an area of skin having a lesion, wart, seborrheic keratosis, or other skin formation. In some embodiments, the one or more debriding elements may be configured to disturb the surface of, decrease the size of, decrease the thickness of, and/or decrease the volume of a lesion or other skin formation. In some embodiments, the one or more debriding elements may include an abrasive element, a sharp, a tip, a curette, or any other element and/or formation capable of debriding or otherwise effecting a lesion or other skin formation. In such embodiments, an operator may use the one or more debriding elements to debride or otherwise effect a lesion or other skin formation before, after, and/or during application of the compositions of embodiments herein via the applicator 1300.

Figure 14A:
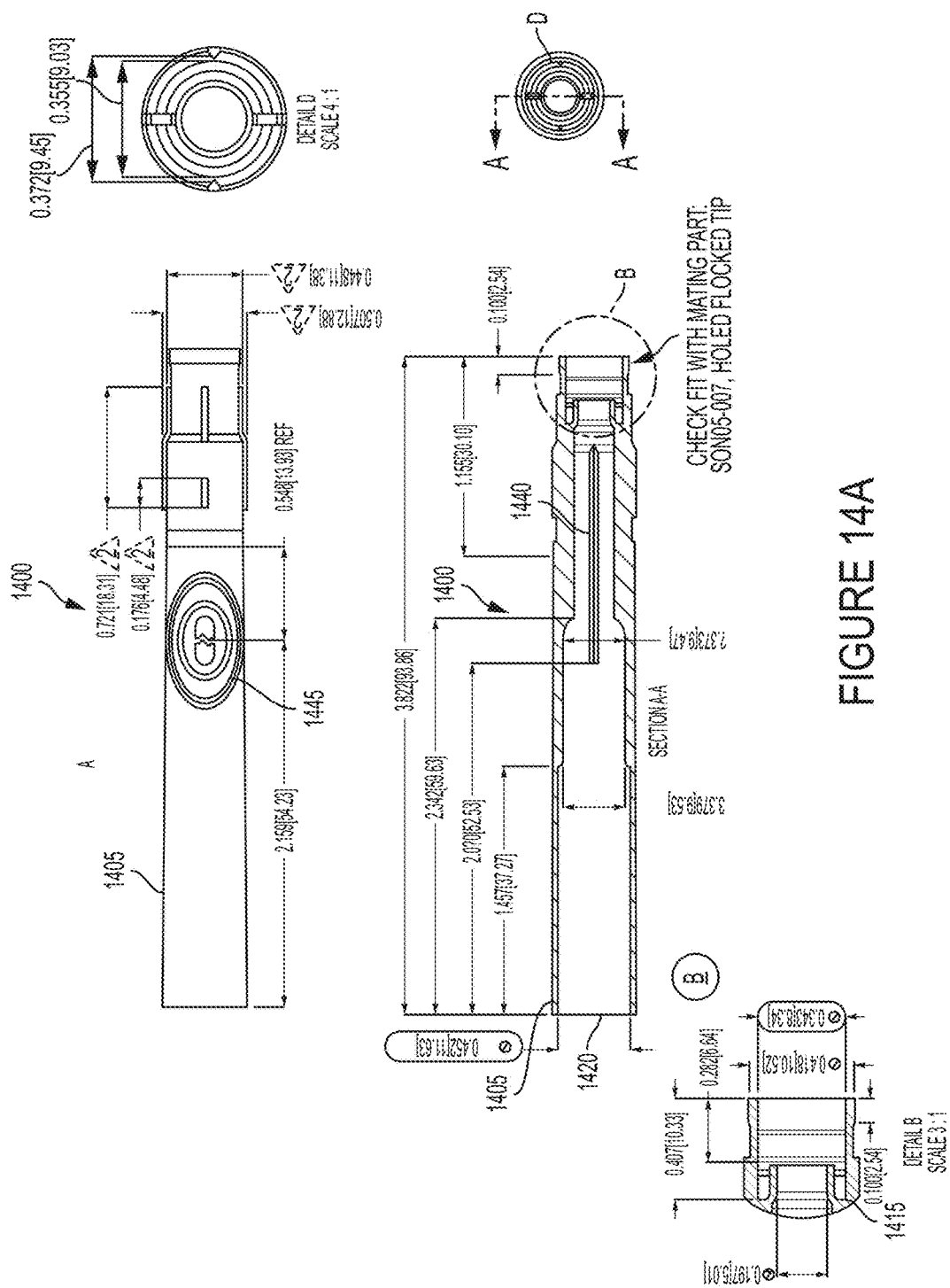

FIGS. 14A and 14B depict multiple views of the applicator body according to some embodiments. As shown in the side view A of FIG. 14A, the applicator body 1400 may include a housing 1405 having a pressure area 1445 arranged thereon. As depicted in internal view B of FIG. 14A, the applicator body 1400 may include a support structure 1440 arranged therein. An end cap 1415 may be configured to be coupled, including removably coupled, to a distal end 1420 of the applicator body 1400. FIG. 14B depicts a side view A and a top-down view B of an applicator body having a grip 1425.

Figure 15:
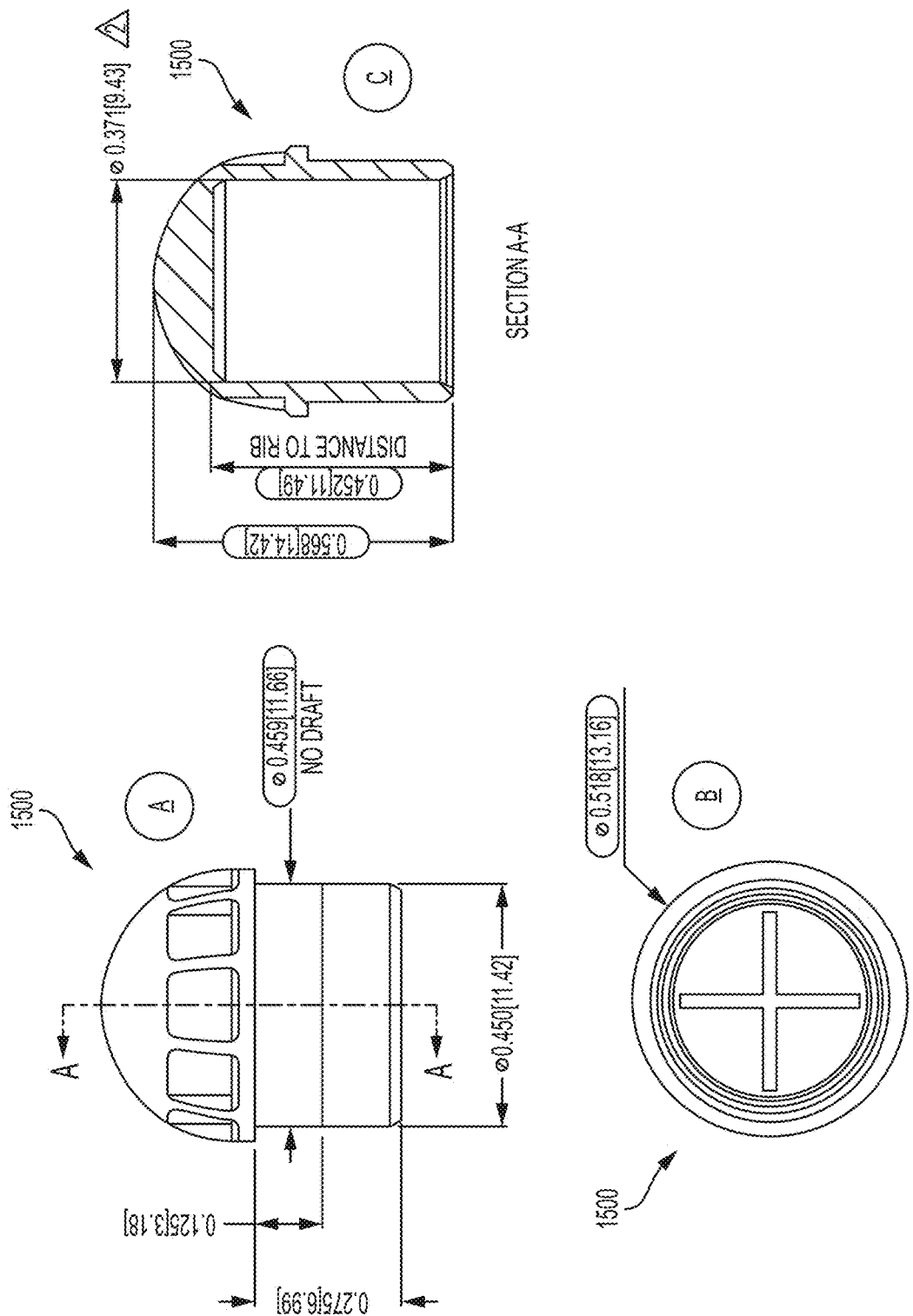
FIG. 15 depicts an illustrative end cap of an applicator according to some embodiments.
Figure 16:
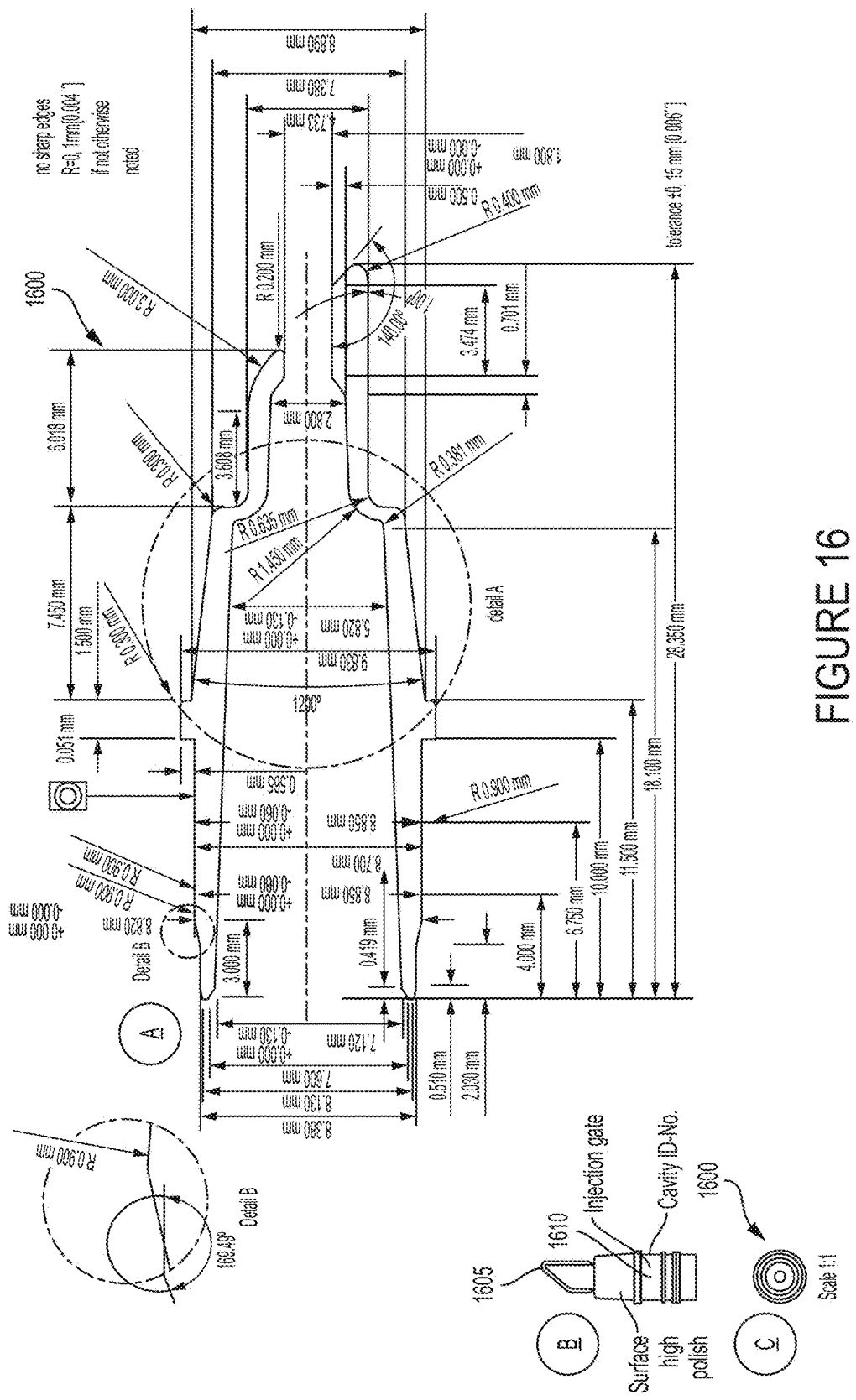
FIG. 16 depicts an illustrative holed flocked tip (or "applicator hub") according to some embodiments.

FIG. 15 depicts an illustrative end cap of an applicator according to some embodiments. In particular, FIG. 15 depicts a side view A, a top-down view B, and an internal side view C of an end cap 1500. FIG. 16 depicts a holed flocked tip (or "applicator hub") according to some embodiments. More specifically, FIG. 16 depicts an internal side view A, a side view B, and a top-down view C of a holed flocked tip 1600. As shown in side view B of FIG. 16, the holed flocked tip 1600 may include a flocked portion 1605 and an injection gate portion 1610.

Figure 17A:
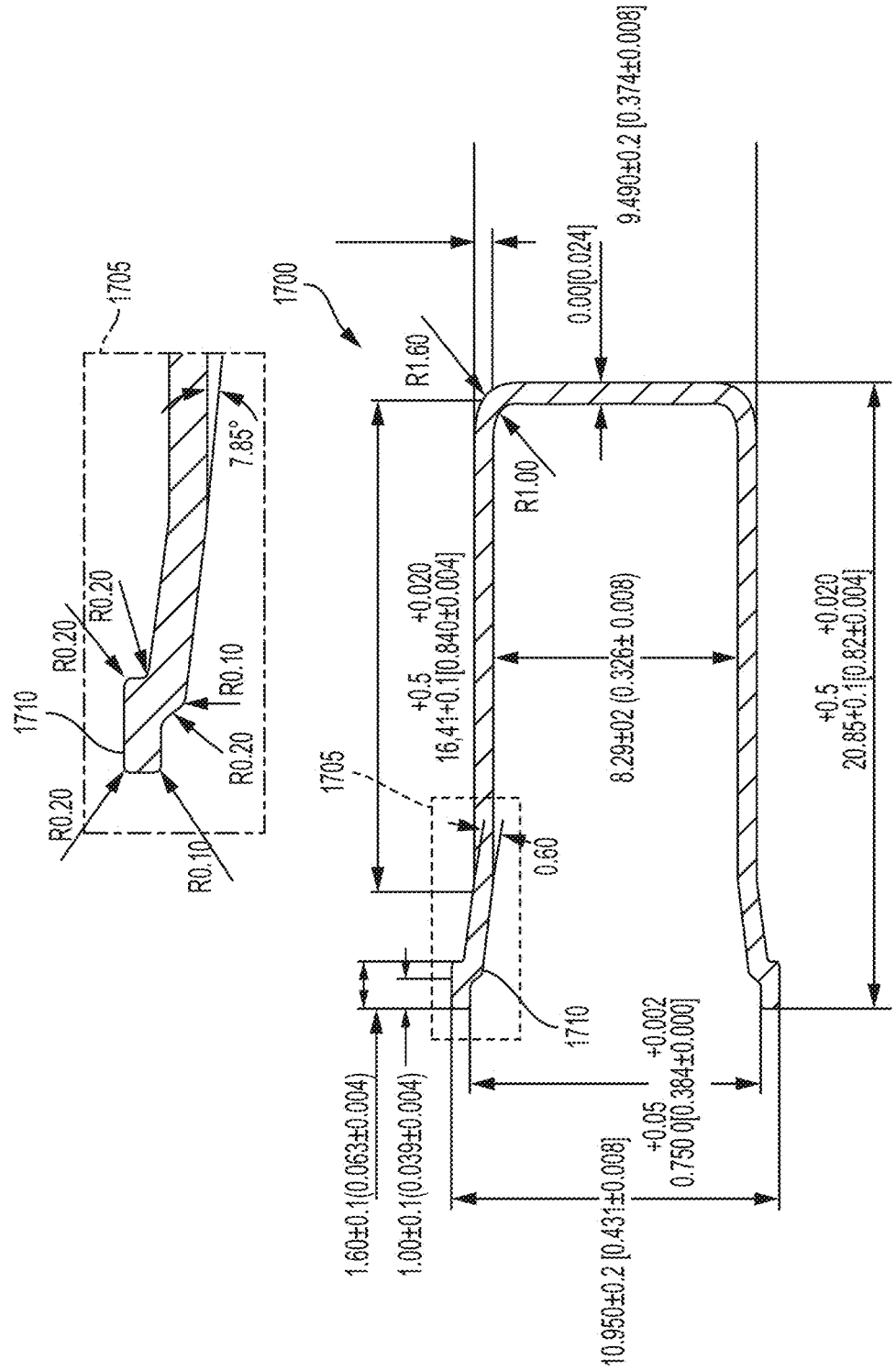
FIGS. 17A and 17B depict an illustrative protective cap according to a first embodiment.
Figure 17B:
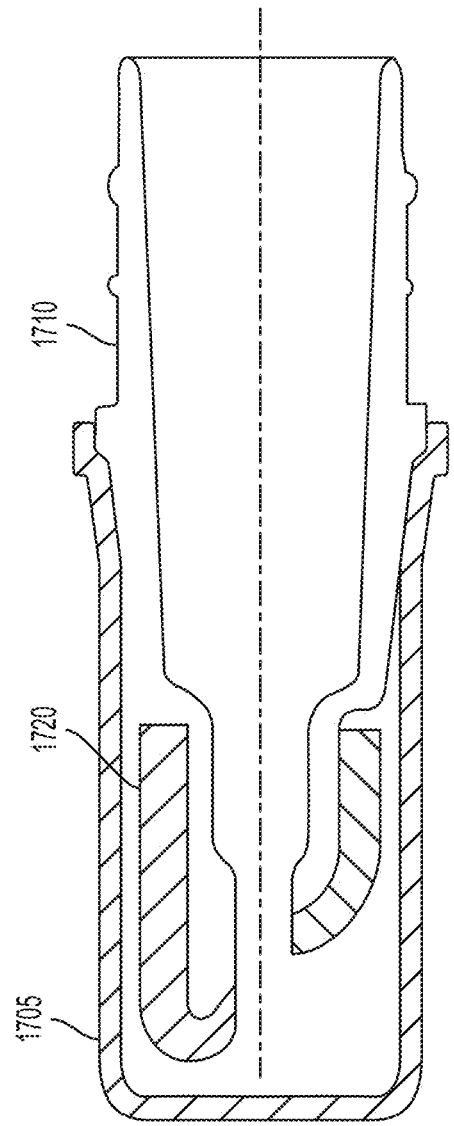
Figure 18A:
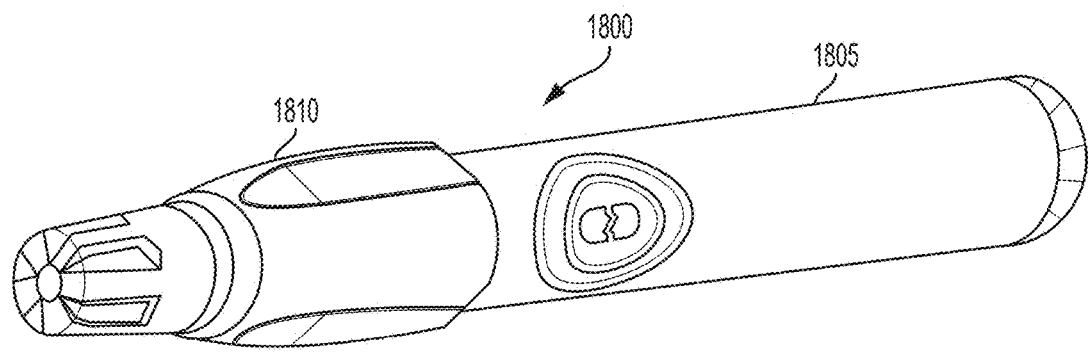
FIGS. 18A and 18B depict an illustrative protective cap according to a second embodiment.
Figure 18B:
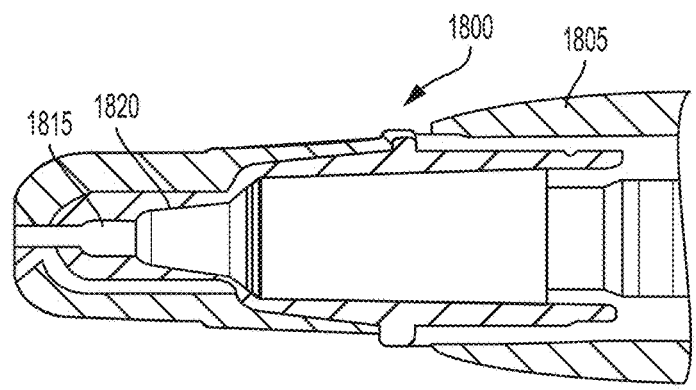

FIG. 17A depicts an internal side view of a protective cap 1700 according to some embodiments, including detail 1705 for the distal portion 1710 of the protective cap. FIG. 17B depicts the protective cap 1700 arranged on a portion of the applicator body 1710 and enclosing a tip 1720 of the applicator according to some embodiments. FIGS. 18A and 18B depict a side view and an internal view, respectively, of an applicator 1800 according to some embodiments. As shown in FIG. 18A, the applicator 1800 may include an applicator body 1805 enclosed by a protective cap 1810. FIG. 18B depicts an internal view of a protective cap 1810 having a spine 1815 extending from an internal surface thereof. When the protective cap 1810 is coupled to the applicator body 1805, the spine 1815 may engage or interface with the holed flocked tip 1820. In some embodiments, the spine 1815 may plug, block, or otherwise close one or more holes in the holed flocked tip 1820, preventing, for instance, fluid from exiting the holed flocked tip. While embodiments set forth herein are described in terms of "comprising", all of the foregoing embodiments also include compositions and methods that consist of only the ingredients or steps recited or consist essentially of the ingredients and steps recited, and optionally additional ingredients or steps that do not materially affect the basic and novel properties of the composition or method.

This disclosure and embodiments illustrating the method and materials used may be further understood by reference to the following non-limiting examples.

Example 1

A seborrheic keratosis (SK) lesion on a 76 year old female with Fitzpatrick skin type 1 was treated with a solution comprised of 40% stabilized hydrogen peroxide and 5% 2-propanol. After cleansing the skin with 70% 2-propanol, the hydrogen peroxide solution was applied topically to the seborrheic keratosis lesion using a flocked doe-foot shaped applicator. Using firm pressure and an application technique that was appropriate for the target lesion size, the solution was applied for approximately 20-30 seconds. After approximately 1-2 minutes, the application process was repeated. This sequence was repeated until 4 applications had been performed. There was no pain or discomfort during the procedure. Follow-up one week later revealed the SK lesion to be resolving. Follow-up 3 weeks after treatment revealed the lesion to be resolving, but not completely cleared. A second treatment session identical to the first was performed 3 weeks after the first treatment. Follow-up 5 weeks and 8 weeks after the second treatment revealed the lesion was completely resolved with no evidence of recurrence of the lesion and no adverse cosmetic sequlae (e.g., scarring or pigmentary change (hyperpigmentation or hypopigmentation)). The subject was extremely pleased with the results.

Example 2

A seborrheic keratosis (SK) lesion on a 65 year old female with Fitzpatrick skin type 4 was treated with a solution comprised of 32.5% stabilized hydrogen peroxide and 5% 2-propanol. After cleansing of the skin with 70% 2-propanol, the solution was applied topically to the seborrheic keratosis lesion using a flocked doe-foot shaped applicator. Using firm pressure and an application technique that was appropriate for the target lesion size, the solution was applied for approximately 20-30 seconds. After approximately 1-2 minutes, the application process was repeated. This sequence was repeated until 4 applications had been performed. There was no pain or discomfort during the procedure. Follow-up 3 weeks after treatment revealed the lesion to completely resolved with no evidence of scarring or pigmentary change (hyperpigmentation or hypopigmentation). The subject was extremely pleased with the results. Follow-up 11 weeks after the treatment revealed no recurrence of the lesion and no adverse cosmetic sequlae.

Example 3

A seborrheic keratosis (SK) lesion on a 73 year old male with Fitzpatrick skin type 3 was treated with a solution comprised of 25% stabilized hydrogen peroxide and 5% 2-propanol. After cleansing of the skin with 70% 2-propanol, the solution was applied topically to the seborrheic keratosis lesion using a flocked doe-foot shaped applicator. Using firm pressure and an application technique that was appropriate for the target lesion size, the solution was applied for approximately 20-30 seconds. After approximately 1-2 minutes, the application process was repeated. This sequence was repeated until 4 applications had been performed. There was no pain or discomfort during the procedure. Follow-up 3 weeks after treatment revealed the lesion to be improved, but not completely resolved. A second treatment session identical to the first was performed 3 weeks after the first treatment. Follow-up 1 week after the second treatment session revealed the SK lesion to be completely resolved with no evidence of scarring or pigmentary change (hyperpigmentation or hypopigmentation). Follow-up 8 weeks after the second treatment (11 weeks after the first treatment) revealed no recurrence of the lesion and no adverse cosmetic sequelae. The subject was extremely pleased with the results.

Example 4

A common wart (verruca) on the cheek of a 56 year old white male (Fitzpatrick Type 2 skin) was treated with a solution comprising 40% hydrogen peroxide (FMC/PeroxiChem "Super D"), and 5% 2-propanol (Spectrum Chemical USP Grade). After cleansing of the skin with 70% 2-propanol, the solution was applied topically to the seborrheic keratosis lesion using a flocked doe-foot shaped applicator. Using firm pressure and an application technique that was appropriate for the target lesion size, the solution was applied for approximately 20-30 seconds. After approximately 1-2 minutes, the application process was repeated. This sequence was repeated until 4 applications had been performed. There was no pain or discomfort during the procedure. Over the next several days the lesion evidenced superficial crusting and mild erythema (redness). Follow-up 2 weeks after the treatment revealed the verruca to be completely resolved with no erythema and no evidence of scarring or pigmentary change (hyperpigmentation or hypopigmentation). Follow-up 8 weeks after the treatment revealed no recurrence of the lesion and no adverse cosmetic sequelae. The subject was extremely pleased with the results.

Example 5

Figure 8:
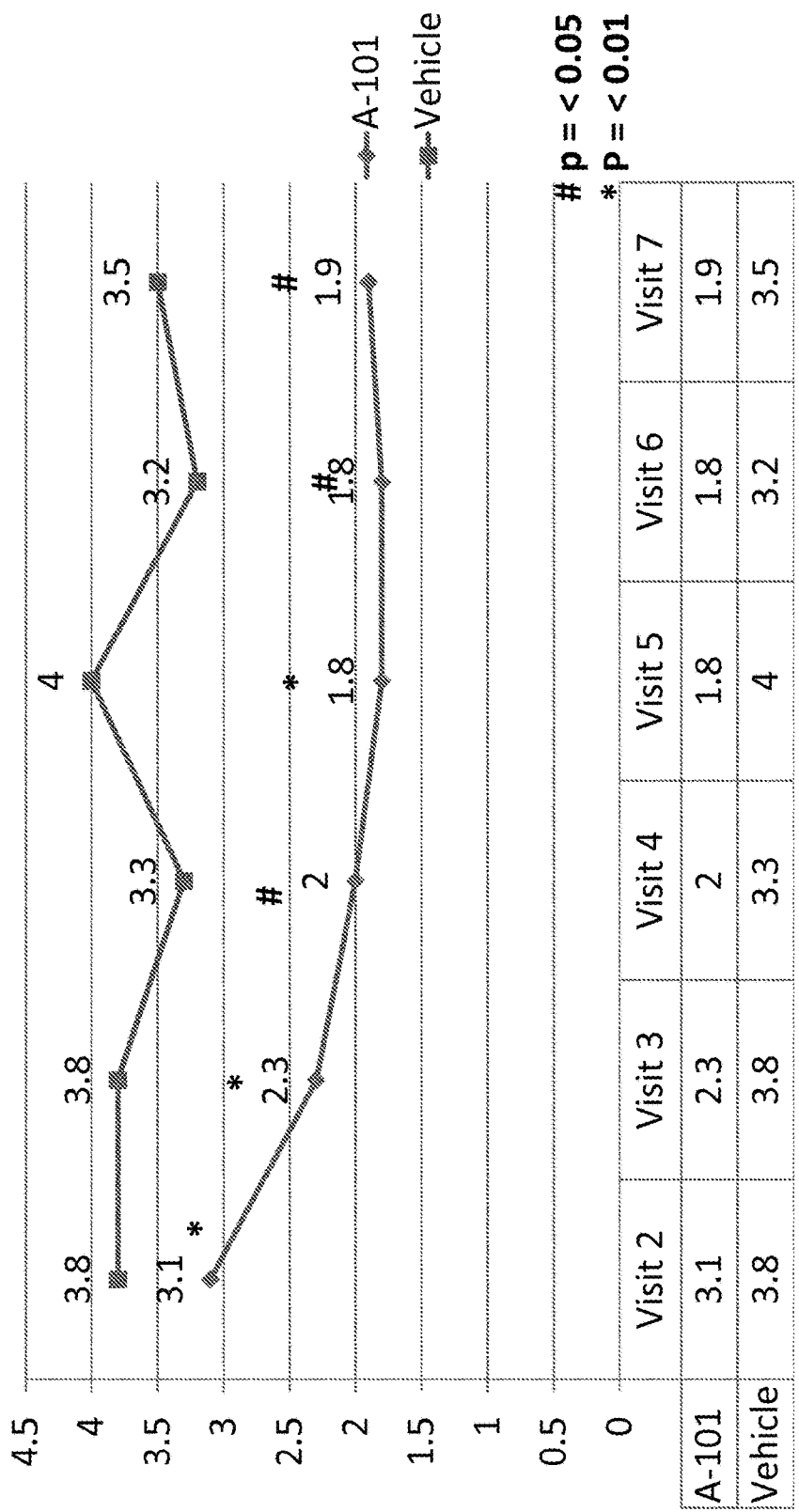
FIG. 8 illustrates the mean Wart Improvement Assessment score by visit.
Figure 9:
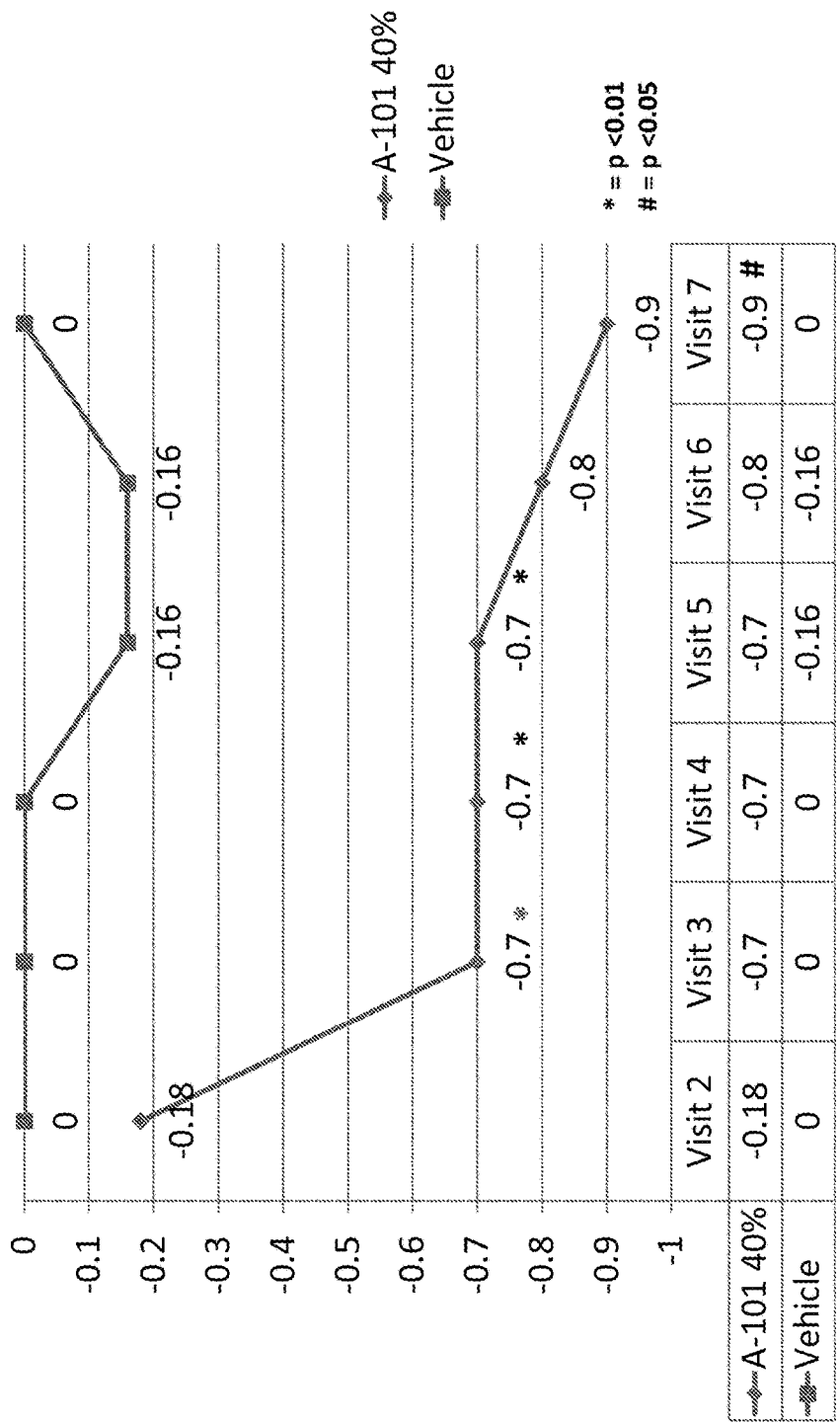
FIG. 9 illustrates the mean change in baseline in the Wart Severity Assessment score by visit.

A randomized, double-blind, vehicle-controlled, parallel group study was conducted with 22 subjects, to evaluate the effectiveness of a 40% topical solution of hydrogen peroxide and 5% 2-propanol when applied once weekly (with a maximum of 4 applications) to treatment-naïve common warts on the extremities (not periungual or subungual) compared with a matching topical solution vehicle. The treatment protocol included (1) cleansing the target wart by rubbing with a swab/wipe wetted with 70% 2-propanol; (2) wetting the supplied applicator with a quantity of study medication sufficient to wet the target wart with a thin film; (3) applying the study medication to the target wart for approximately 10 seconds using firm pressure and a circular motion; (4) absorbing excess study medication with a clean absorbent wipe (or equivalent) to minimize exposure to normal surrounding skin; (5) repeating the application procedure 3 times after a waiting period of about 20 seconds after each application. After completing the third study medication application to the target wart, the target wart was not disturbed until all visible reaction, if any, had stopped. After approximately 10 minutes, any remaining study medication was absorbed and the target wart was dried without wiping or rubbing. 17 subjects completed all four weekly treatments. All subjects tolerated the procedure well, no adverse events were reported, and local skin reactions were reported as none or mild. While no wart lesions were completely resolved at the conclusion of this pilot study (4 weekly doses)—it was expected that some of the wart lesions would show improvement, but that complete cure of the lesions might take more than four treatments (e.g., up to 10 or up to 30 treatments or more)—which is common with topical wart treatments—(e.g., over-the-counter daily salicylic acid treatments) or would require more frequent application than weekly (e.g., twice weekly or daily)—a statistically significant improvement in the lesions was demonstrated and the proof-of concept was validated. Subjects showed a statistically significant improvement in wart severity as measured by the mean Wart Improvement Assessment score by visit (FIG. 8) and by the mean change in baseline in the Wart Severity Assessment score by visit (FIG. 9). FIG. 7 describes the Wart Improvement Assessment score and Wart Severity Assessment score.

Example 6

In vitro Drug Release and in vitro Skin Permeation studies were performed. Thirteen formulations of 40% w/w hydrogen peroxide were prepared using a stock solution of 50% FMC/PeroxyChem "Super D" stabilized hydrogen peroxide as the peroxide source, with different levels of 1 and 2-propanol for assessment—as indicated in Table 1.

TABLE 1

| | Formulation and composition of excipients (% w/w) | | | | | | | | | | | | |
|---|---|---|---|---|---|---|---|---|---|---|---|---|---|
| Excipient | P1-20 | P1-15 | P1-10 | P1-5 | P1-2.5 | P1-1 | P2-20 | P2-15 | P2-10 | P-2-5 | P2-2.5 | P2-1 | Control |
| H2O2 (50% w/w) | 80.00 | 80.00 | 80.00 | 80.00 | 80.00 | 80.00 | 80.00 | 80.00 | 80.00 | 80.00 | 80.00 | 80.00 | 80.00 |
| 1-propanol | 20.00 | 15.00 | 10.00 | 5.00 | 2.50 | 1.00 | — | — | — | — | — | — | — |
| 2-propanol | — | — | — | — | — | — | 20.00 | 15.00 | 10.00 | 5.00 | 2.50 | 1.00 | — |
| Triethanolamine | | | | | | | To pH 3.5 | | | | | | |
| Deionized water | — | q.s. 100% | | | | | — | | | q.s. 100% | | | |

Figure 2:
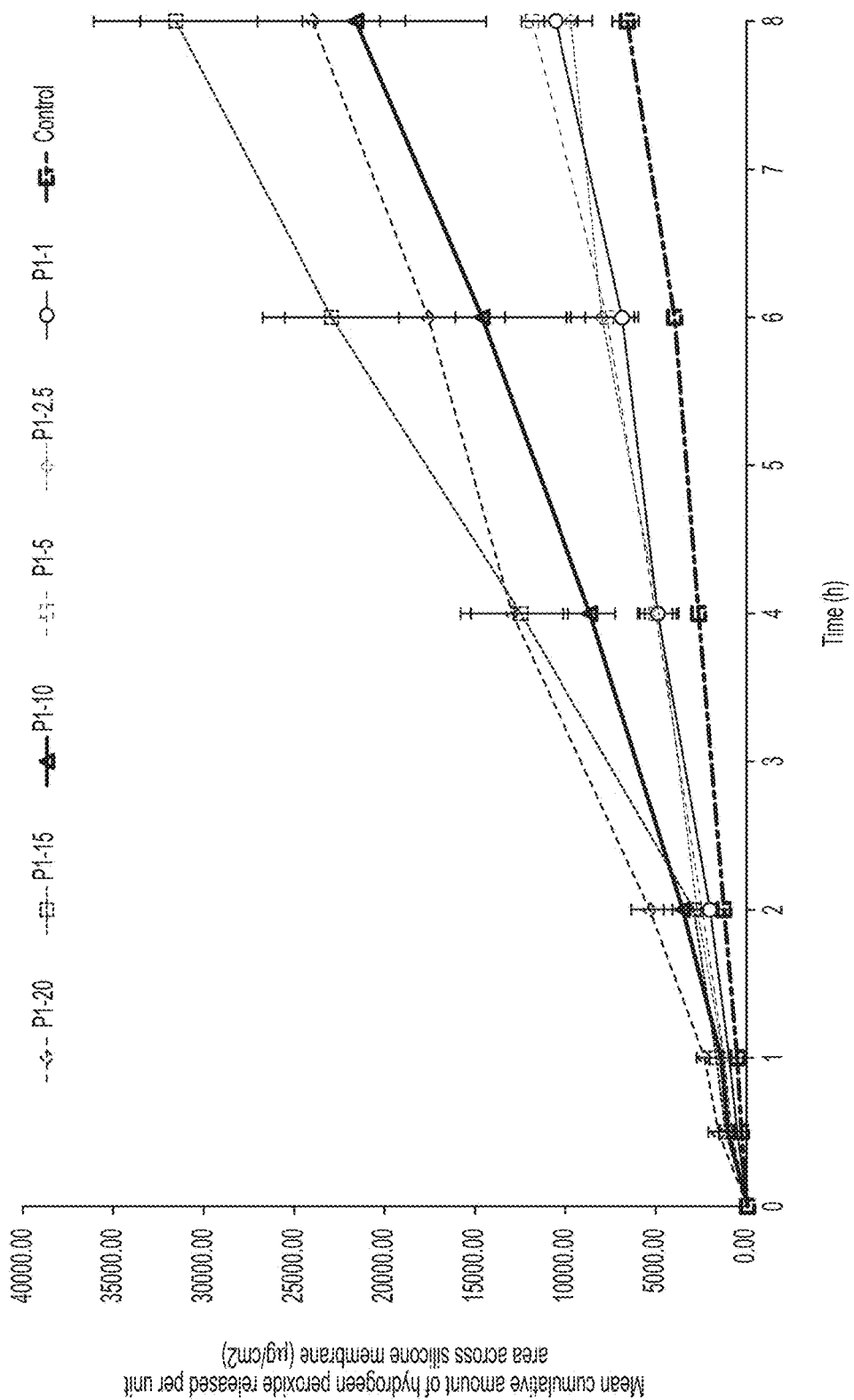
FIG. 2 illustrates the mean cumulative amount of hydrogen peroxide released per unit area across silicone membrane ($\mu g/cm^2$) following application of 40% w/w hydrogen peroxide formulations containing 1-propanol. Each time point represents the mean±SD (n=5-6).
Figure 3:
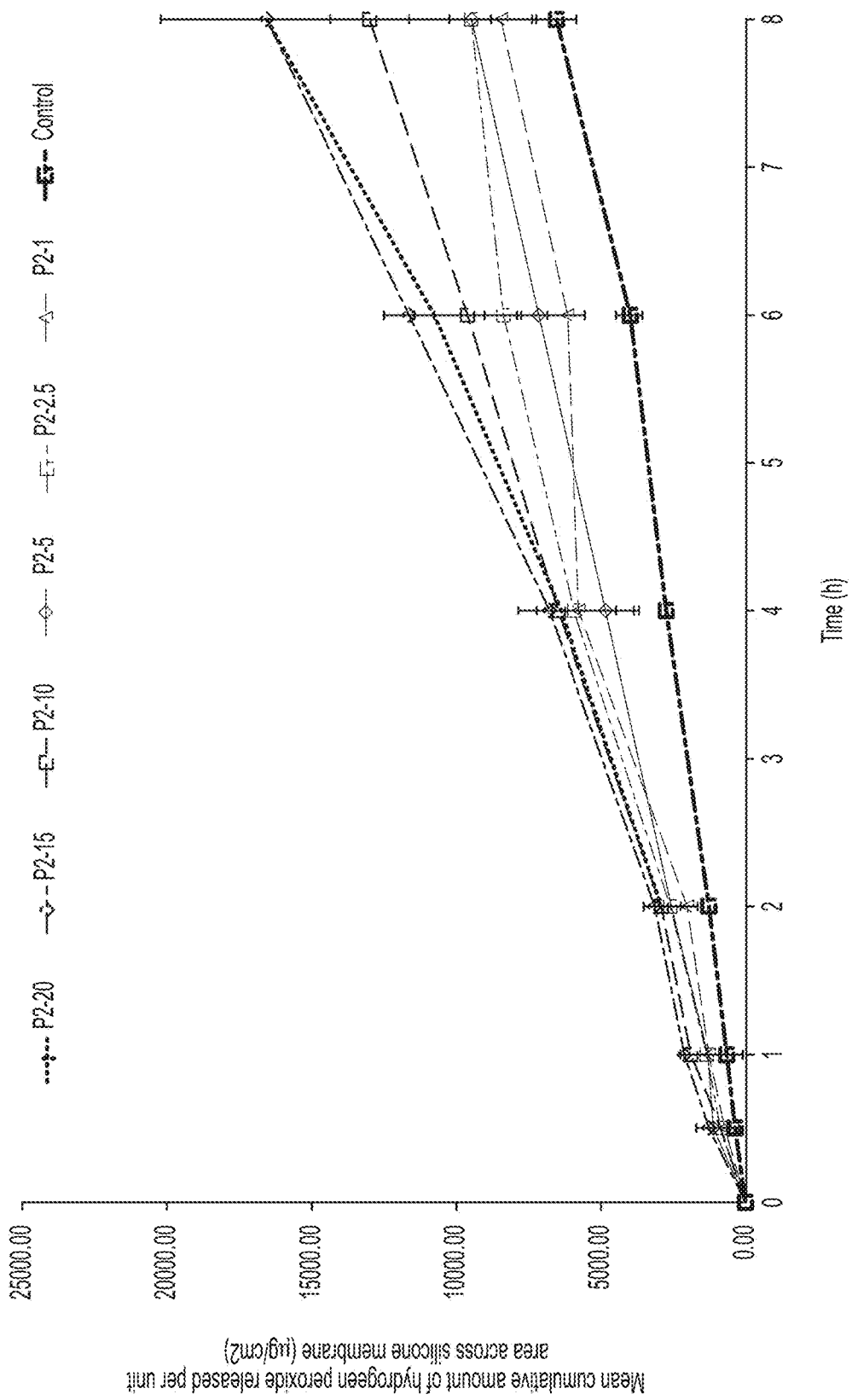
FIG. 3 illustrates the mean cumulative amount of hydrogen peroxide released per unit area across silicone membrane ($m/cm^2$) following application of 40% w/w hydrogen peroxide formulations containing 2-propanol. Each time point represents the mean±SD (n=5-6).

An in vitro drug release study (based on SUPAC guidelines) with the 13 formulations was performed. The receiver fluid was PBS, the synthetic membrane was silicone (selected after preliminary suitability studies), and sampling volume was 1 mL with 1 mL replenished. The measurement time points were at 0 min, 0.5 hr, 1 hr, 2 hr, 4 hr, 6 hr, and 8 hr. FIG. 1 illustrates the mean cumulative amount of hydrogen peroxide released per unit area following application of all formulations. FIGS. 2 and 3 compare the release of hydrogen peroxide between formulations containing 1- and 2-propanol, respectively, demonstrating that, in general, increasing either 1-propanol or 2-propanol content in the formulations produces an increase in the amount of hydrogen peroxide released across the silicone membrane.

Figure 4:
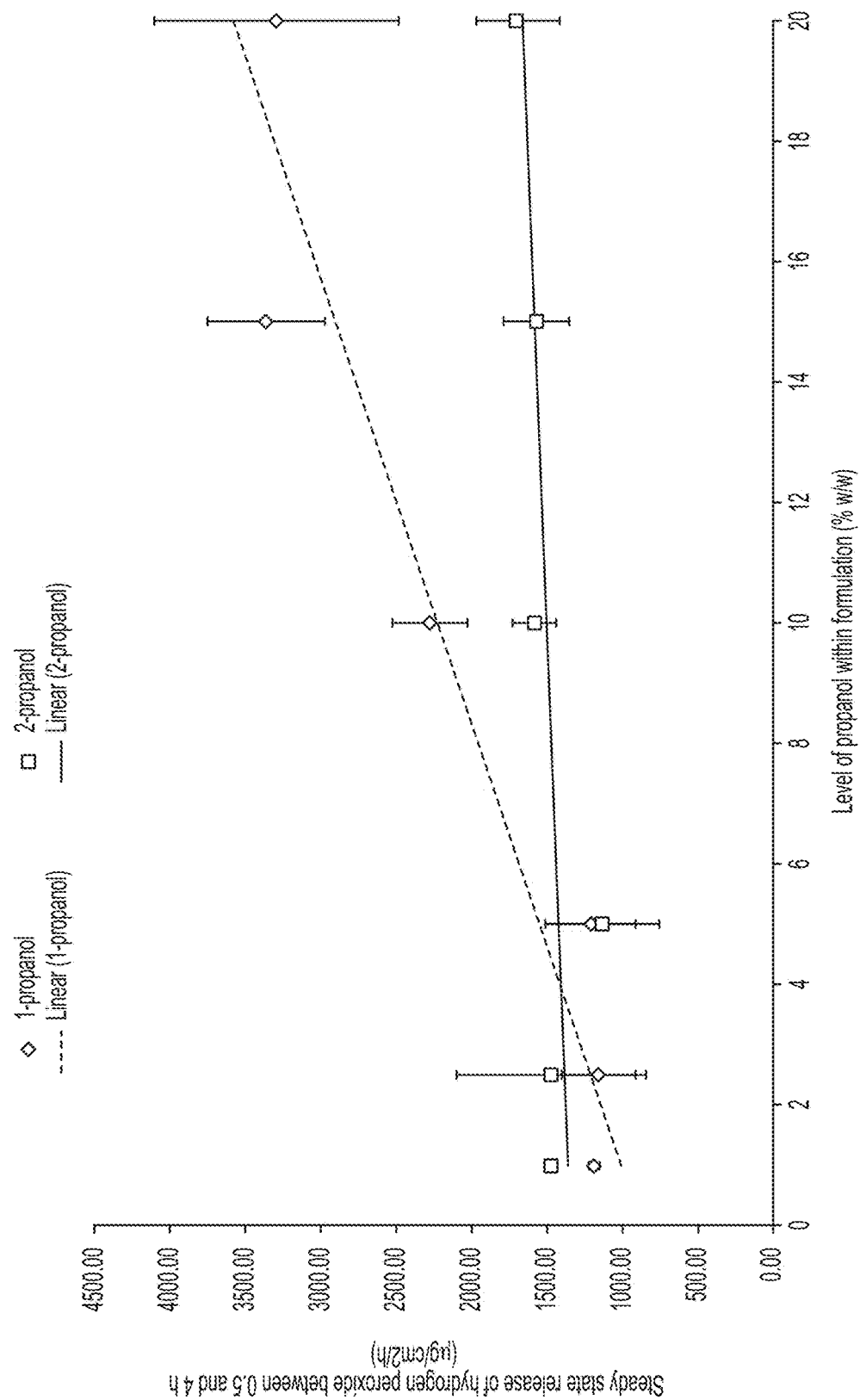
FIG. 4 illustrates the steady state release of hydrogen peroxide, calculated between 0.5 and 4 h ($\mu g/cm^2/h$) following application of hydrogen peroxide formulations at varying levels of propanol. Each data point represents the mean±SD, n=5-6.
Figure 5:
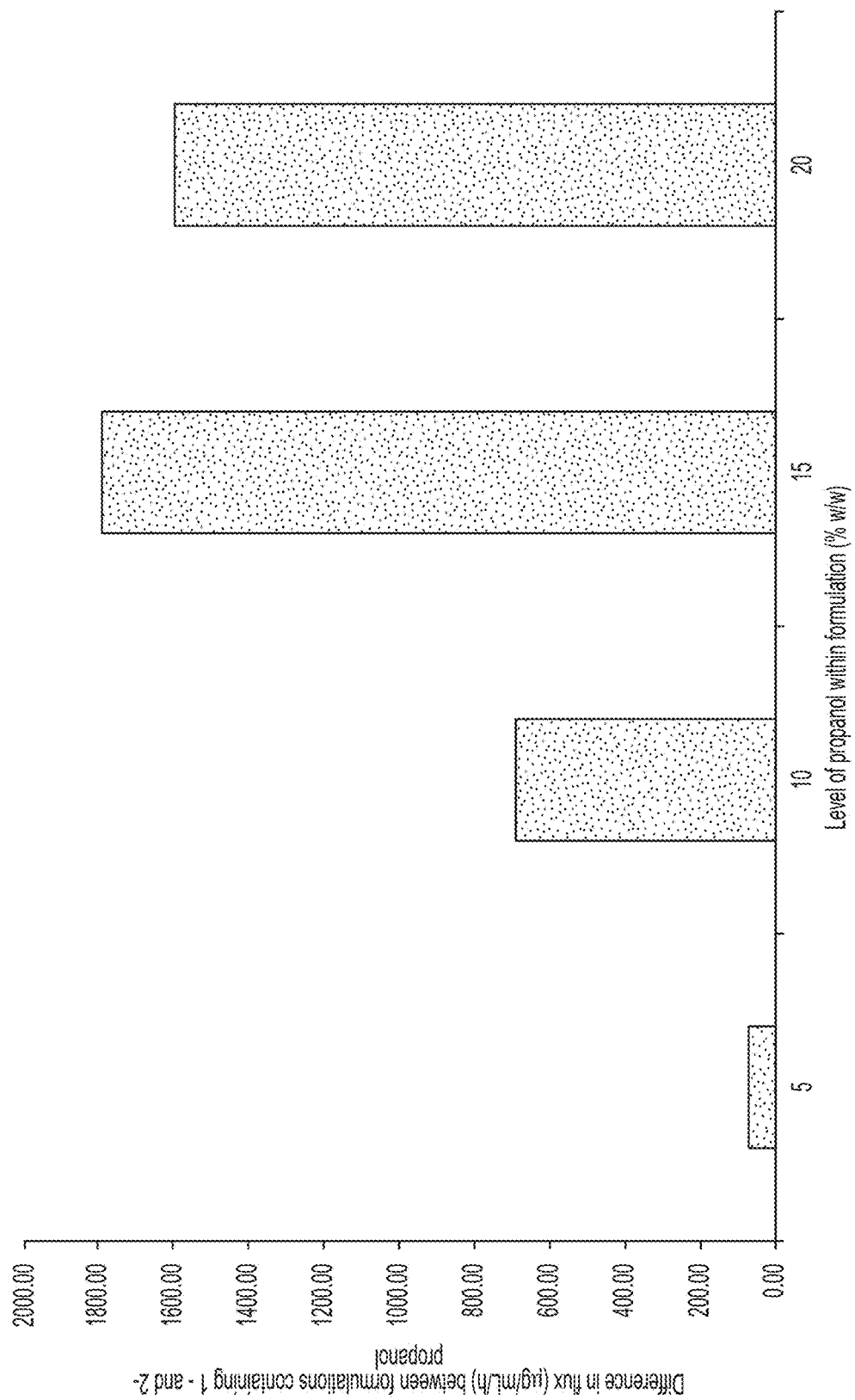
FIG. 5 illustrates the difference in the steady state release of hydrogen peroxide (Flux [1-propanol]-Flux [2-propanol]) for 5, 10, 15 and 20% w/w (1-propanol and 2-propanol).

While in general, a higher amount of hydrogen peroxide is released following application of formulations containing 1-propanol compared to 2-propanol on a w/w basis, this trend is most apparent in the 1-propanol formulations and in formulations of higher concentrations of the alcohols— beginning at approximately above 5% alcohol concentration—and observed to a much greater degree as the alcohol concentration increases to 10%, 15% and 20%. This effect is illustrated by FIG. 4, which shows the steady state release of hydrogen peroxide between 0.5 h and 4 h for the different concentrations of 1-propanol and 2-propanol and FIG. 5, which shows the difference in steady state release of hydrogen peroxide between formulations containing 1-propanol and 2-propanol at levels of 5-20% w/w. For formulations containing 1-propanol, there is an increase in the steady state release of hydrogen peroxide (over 0.5 to 4 h) on increasing 1-propanol content, however for formulations containing 2-propanol, the steady state release of hydrogen peroxide appears to remain essentially constant across the tested concentrations of 2-propanol.

Surprisingly, and importantly, this effect of the rate of release (0.5-4 h) of hydrogen peroxide from 1-propanol formulations being greater than corresponding 2-propanol formulations is reversed at lower concentrations of the alcohols, e.g., below approximately 5% alcohol, with the rate of hydrogen peroxide release from the 2-propanol formulations at lower alcohol concentrations (e.g., <5%) being greater than the rate of hydrogen peroxide release from the 1-propanol containing formulations. Therefore, in the lower range of alcohol concentrations to be incorporated in a preferred embodiment of the formulation, which is most desirable, as minimizing the concentration of the alcohol to be added may minimize the potential impurities introduced into the peroxide formulation, it is unexpectedly discovered that 2-propanol may be preferred over 1-propanol. Without wishing to be bound by theory, it appears that the rate of release of hydrogen peroxide at lower concentrations of 2-propanol will greater than for the 1-propanol.

Example 7

Figure 10:
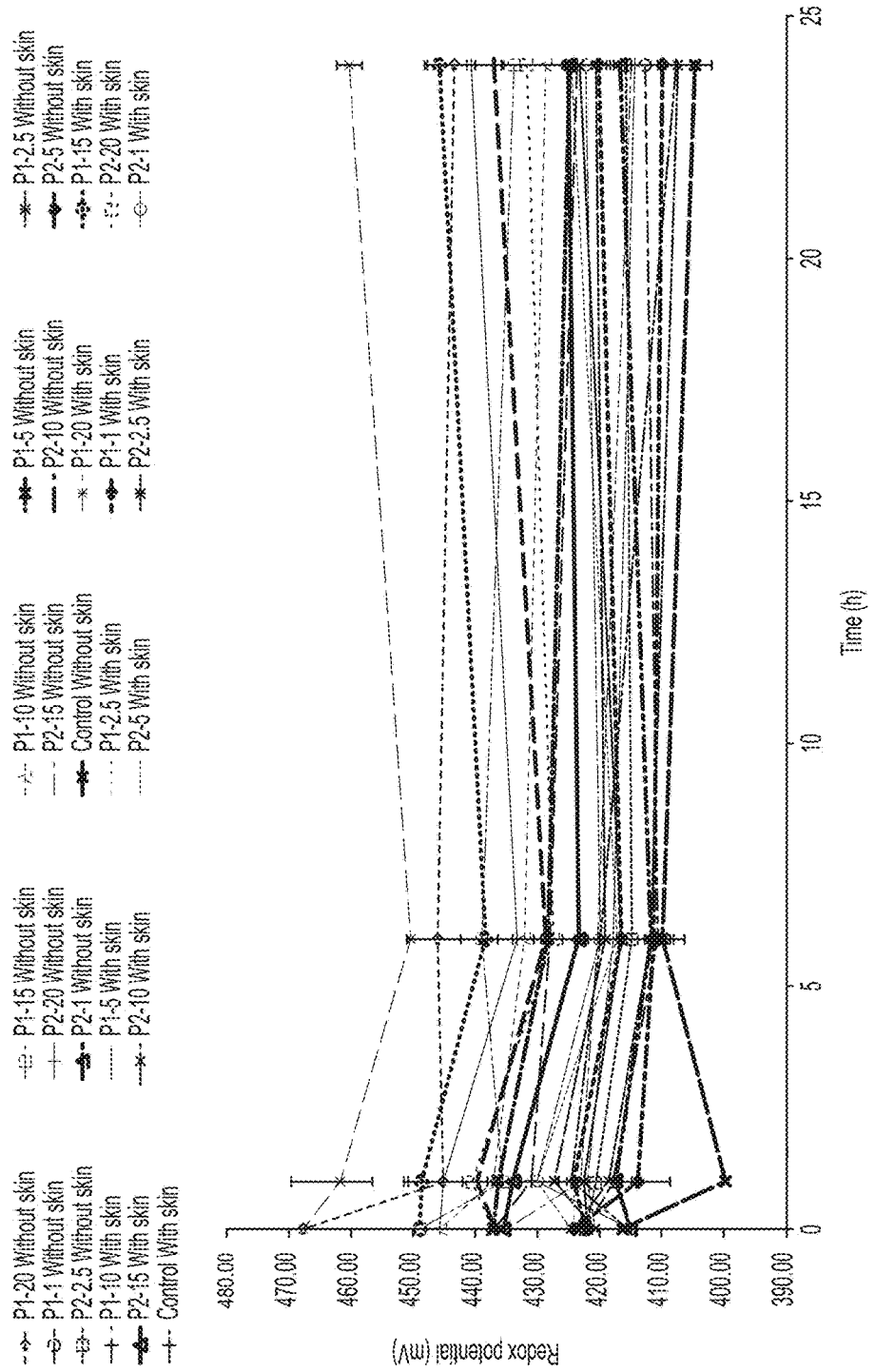
FIG. 10 illustrates the redox potential (mV) of all 40% w/w hydrogen peroxide formulations containing 1- and 2-propanol, with and without skin at t=0, 1, 6 and 24 h. Each time point represents the mean±range, n=3.

Oxidation assessment by redox potential measurement: Assessment of oxidation (by measuring redox potential) was performed on 13 prepared 40% w/w hydrogen peroxide formulations as summarized in Table 1 with and without skin at t=0, 1, 6 and 24 hr (n=3 repetitions was performed). The redox potential data of each of the 13 formulations summarized in Table 1 above is illustrated in FIG. 10.

Figure 11:
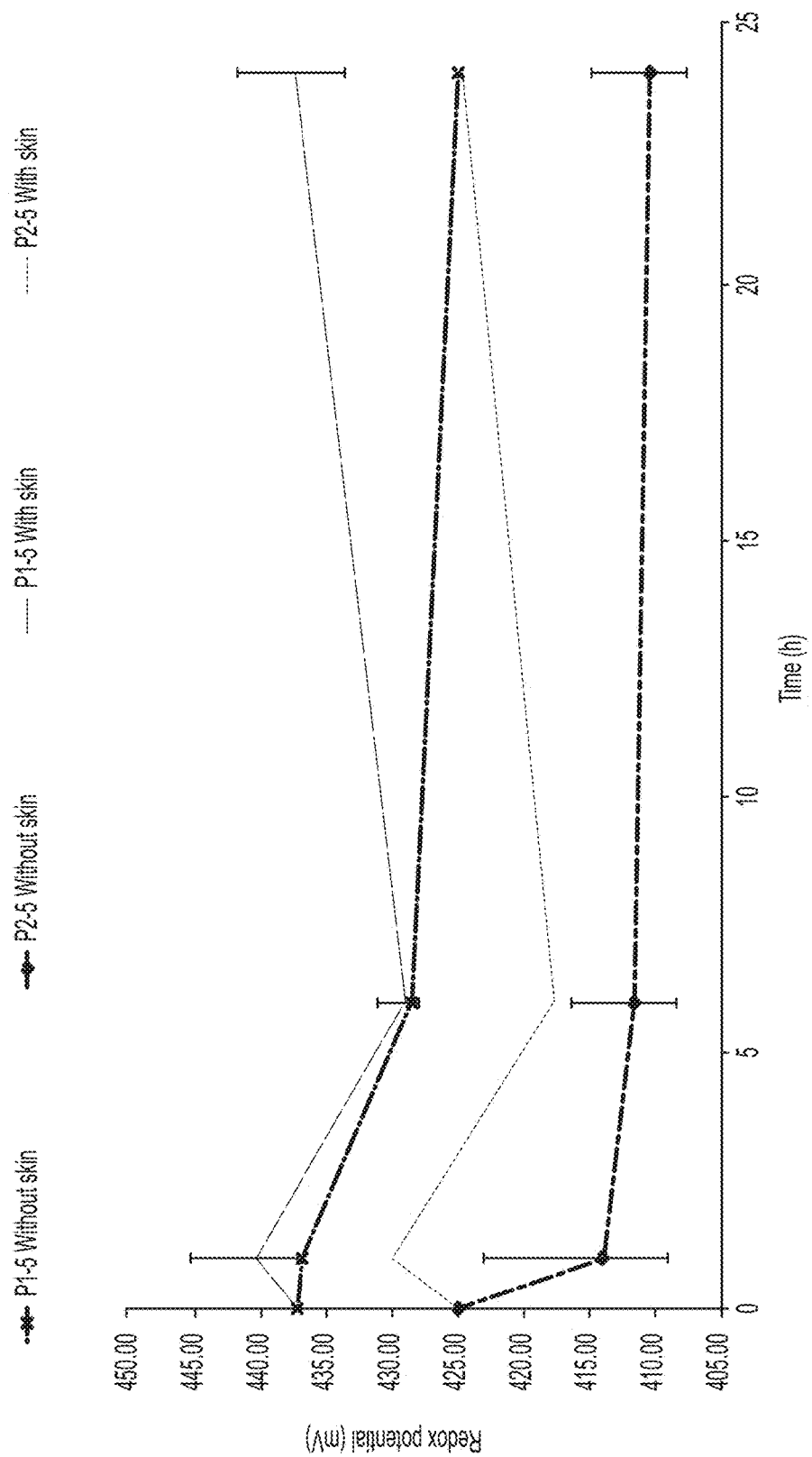
FIG. 11 illustrates the redox potential (mV) of 40% w/w hydrogen peroxide formulations containing 5% w/w 1- or 2-propanol, in with and without skin at t=0, 1, 6 and 24 h. Each time point represents the mean±range, n=3.

While for formulations containing less than 5% w/w propanol, the data were not statistically significant, for formulations containing 5% to 20% w/w propanol, a higher (more positive) redox potential was measured for formulations containing 1-propanol when compared to 2-propanol. That is, 1-propanol, when incorporated into hydrogen peroxide formulations in this concentration range (i.e. 40%), will have a greater propensity to be oxidized than 2-propanol when incorporated into these same hydrogen peroxide formulations. A similar trend is observed in the presence of skin, where the relative redox potential between the 1-propanol and 2-propanol containing formulations is maintained. The data for the study investigating the redox potential of 40% w/w hydrogen peroxide formulations containing 5% w/w 1- or 2-propanol, both with and without skin is illustrated in FIG. 11. Thus, while it may be theoretically expected that secondary alcohols, (e.g., 2-propanol) are inherently less stable in high concentrations of hydrogen peroxide than primary alcohols, this unexpected result, in fact, demonstrates that 2-propanol is less likely to be oxidized than 1-propanol in these embodiments, and it would be preferable to incorporate 2-propanol into these solutions.

Example 8

Surface tension analysis was performed on the 13 40% hydrogen peroxide formulations with varying 1-propanol or 2-propanol concentrations from Table 1 at 37° C. (in duplicate) using Kruss Tensiometer and the Wilhelmy Plate technique. Calibration of the system using deionised water showed results within 1.0 mN/m of the literature values at 37° C. (ca. 70 mN/m). Each sample had a 30 minute run time and the result was calculated from the mean of the last 10 readings.

Figure 6:
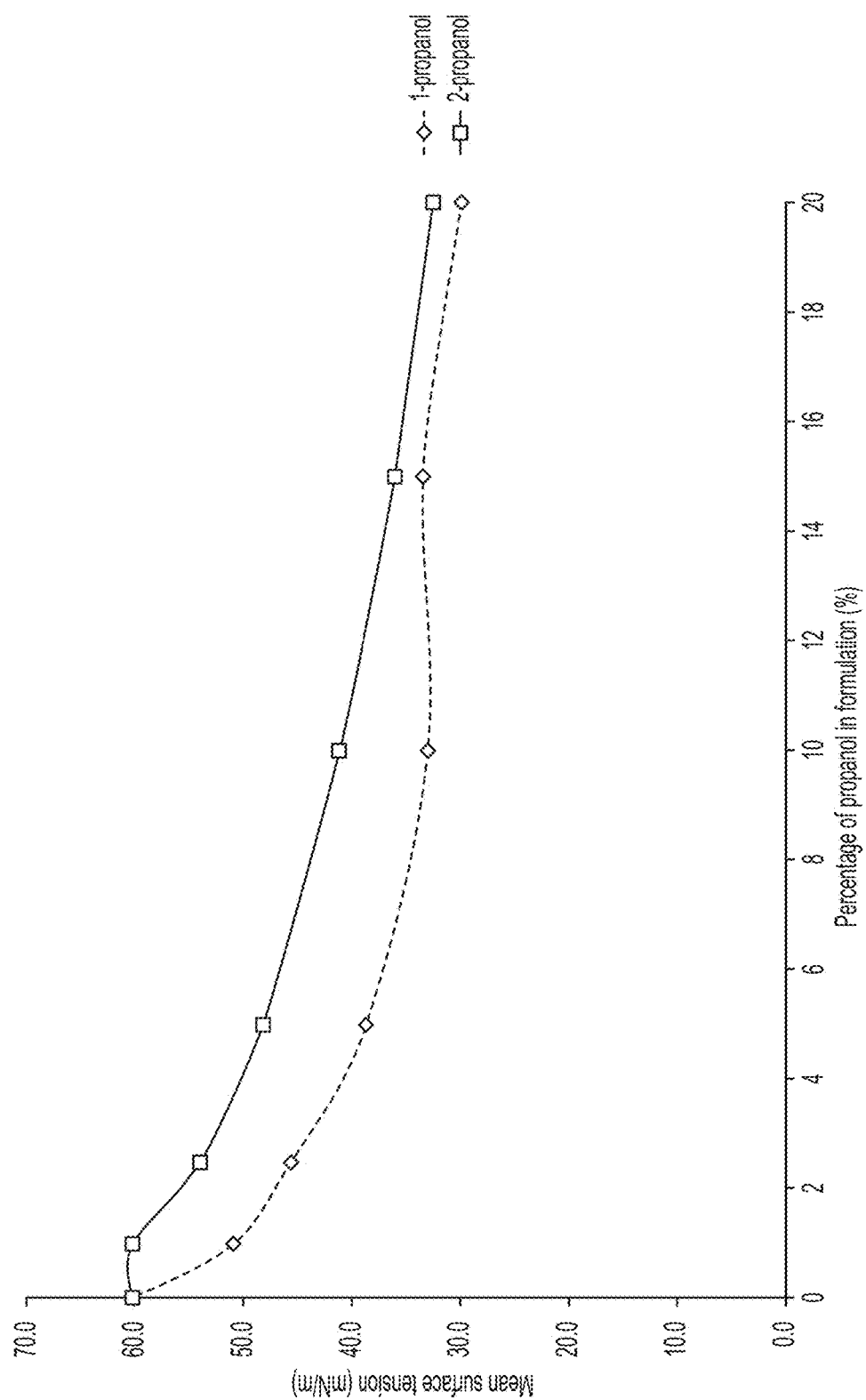
FIG. 6 illustrates the mean surface tension (mN/m) of the different hydrogen peroxide formulations assessed containing either 1- or 2-propanol.

Analysis of the samples was performed in duplicate at 37±0.5° C. using a confidence level of ±1.4%. Where the obtained duplicate results were outside this range, a third test was performed and the reported result was calculated using the 2 closest individual results. All data has been presented in Table 2 below and illustrated in FIG. 6.

TABLE 2

| | Surface Tension (mN/m) | | |
|---|---|---|---|
| Formulation | Results | Range (1st and last reading) | Rounded mean |
| P1-20 | 29.65 | 28.05-29.76 | 29.8 ± 0.4 |
|  | 29.86 | 28.03-29.88 |  |
| P1-15 | 33.44 | 29.61-33.76 | 33.3 ± 0.5 |
|  | 33.22 | 29.71-33.91 |  |
| P1-10 | 35.42 | 32.84-35.30 | 32.9 ± 0.5 |
|  | 33.03 | 32.79-32.96 | (Tests 2 and 3) |
|  | 32.80 | 32.64-32.84 |  |
| P1-5 | 38.90 | 39.99-38.62 | 38.7 ± 0.5 |
|  | 38.46 | 38.79-38.45 |  |
| P1-2.5 | 45.95 | 45.56-45.95 | 45.7 ± 0.6 |
|  | 45.34 | 46.16-45.33 |  |
| P1-1 | 51.58 | 52.37-51.46 | 51.0 ± 0.7 |
|  | 50.35 | 51.76-50.24 |  |
| P2-20 | 32.76 | 33.89-32.59 | 32.6 ± 0.5 |
|  | 32.35 | 34.03-32.20 |  |
| P2-15 | 34.28 | 36.99-34.10 | 35.9 ± 0.5 |
|  | 35.76 | 36.99-35.59 | (Tests 2 and 3) |
|  | 36.11 | 36.94-35.96 |  |
| P2-10 | 41.14 | 41.16-41.23 | 41.1 ± 0.6 |
|  | 41.13 | 40.77-41.26 |  |
| P2-5 | 47.73 | 48.36-47.75 | 48.3 ± 0.7 |
|  | 48.95 | 48.61-49.12 |  |
| P2-2.5 | 53.54 | 54.42-53.46 | 54.1 ± 0.8 |
|  | 54.66 | 54.88-54.66 |  |
| P2-1 | 59.85 | 62.01-59.59 | 60.2 ± 0.8 |
|  | 61.87 | 62.38-61.67 | (Tests 1 and 3) |
|  | 60.59 | 62.25-60.35 |  |
| Control | 58.92 | 61.30-58.66 | 60.3 ± 0.8 |
|  | 60.63 | 65.30-60.18 | (Tests 2 and 3) |
|  | 59.99 | 65.33-59.49 |  |

The data demonstrate that, in general, incorporating either 1-propanol or 2-propanol decreases the surface tension of the tested hydrogen peroxide formulations, and that this surface-tension decreasing effect is roughly proportional to the concentration of the added 1-propanol or 2-propanol. Theoretically, from a surface-tension point of view, either might be thought to be useful to incorporate into the embodiments disclosed herein.

However, the effect of the surface-tension reduction of 1-propanol on the peroxide formulations is more potent than that of 2-propanol such that in the preferred embodiments formulations containing 1-propanol will have a much lower surface tension than the corresponding 2-propanol formulations, and will be much more likely to spread out of the area of application and off the lesion, on to surrounding non-lesional skin thereby lowering the effectiveness of the therapeutic and serving as a substrate for ADH in the skin—resulting in increased irritation, erythema, and adverse cutaneous effects irritating the surrounding skin. 40% hydrogen peroxide was employed in this illustrative study and examples, but by varying the concentration of the alcohol (e.g., 2-propanol) component in other hydrogen peroxide compositions of the embodiments described herein (e.g., in concentrations of hydrogen peroxide of 25%, 32.5%, 40%, 42.5%), an optimal concentration of the alcohol that will produce the optimal surface tension reduction, achieve the desired clinical effect, and minimize the risk of local adverse cutaneous effects may be readily determined.

Example 9

Solutions were prepared using stabilized hydrogen peroxide (Peroxal CG 50® Arkema, Inc.) and 2-propanol 99% (Spectrum Chemical, USP Grade) to make a composition comprising 40% stabilized hydrogen peroxide and 5% 2-propanol and a composition comprising 25% stabilized hydrogen peroxide and 5% 2-propanol. The solutions were placed on stability in Type I amber borosilicate glass screw-top vials and maintained at 25° C./60% relative humidity (RH); 40° C./75% RH; and 5° C. (refrigerated). The 25% stabilized $H_2O_2$/5% IPA solutions remained stable ("in specification" according to ICH Harmonised Tripartite Guideline: Stability Testing of New Drug Substances and Products Q1A(R2)", current Step 4 version, dated 6 Feb. 2003) under the 40° C. conditions at 6 months, and under both the 25° C. conditions and 5° C. conditions at 24 months. The 40% stabilized $H_2O_2$/5% IPA solutions remained stable ("in specification" according to ICH Harmonised Tripartite Guideline: Stability Testing of New Drug Substances and Products Q1A(R2)", current Step 4 version, dated 6 Feb. 2003) under the 40° C. conditions at 6 months, under both the 25° C. conditions and 5° C. conditions at 24 months.

Example 10

Solutions were prepared using stabilized hydrogen peroxide (Peroxal CG 50® Arkema, Inc.) and 2-propanol 99% (Spectrum Chemical, USP Grade) to make a composition comprising 40% stabilized hydrogen peroxide and 15% 2-propanol and a composition comprising 25% stabilized hydrogen peroxide and 15% 2-propanol. The solutions were placed on stability in Type I amber borosilicate glass screw-top vials and maintained at 25° C./60% relative humidity (RH); 40° C./75% RH; and 5° C. (refrigerated). The 25% stabilized $H_2O_2$/15% IPA solutions remained stable ("in specification" according to ICH Harmonised Tripartite Guideline: Stability Testing of New Drug Substances and Products Q1A(R2)", current Step 4 version, dated 6 Feb. 2003) under the 40° C. conditions at 6 months, and under both the 5° C. and 25° C. conditions at 24 months. The 40% stabilized $H_2O_2$/15% IPA solutions remained stable ("in specification" according to ICH Harmonised Tripartite Guideline: Stability Testing of New Drug Substances and Products Q1A(R2)", current Step 4 version, dated 6 Feb. 2003) under the 40° C. conditions at 6 months, and under both the 5° C. and 25° C. conditions at 24 months.

Example 11

Solutions were prepared using stabilized hydrogen peroxide (FMC/PeroxyChem "Super D 50%" (FMC/PeroxyChem) and 2-propanol 99% (Spectrum Chemical, USP Grade) to make a composition comprising 45% stabilized hydrogen peroxide and 5% 2-propanol. The solutions were placed on stability in Type 1 amber borosilicate glass vials in stability chambers and maintained at 25° C./60% relative humidity (RH), 40° C./75% RH, and 5° C. (refrigerated). The 45% stabilized $H_2O_2$/5% IPA solutions remained stable ("in specification" according to ICH Harmonised Tripartite Guideline: Stability Testing of New Drug Substances and Products Q1A(R2)", current Step 4 version, dated 6 Feb. 2003) under the under the 40° C. conditions at 6 months, and under both the 5° C. and 25° C. conditions at 12 months.

Example 12

Solutions were prepared using stabilized hydrogen peroxide (FMC/PeroxyChem "Super D 50%" (FMC/PeroxyChem) and 2-propanol 99% (Spectrum Chemical, USP Grade) to make a composition comprising 40% stabilized hydrogen peroxide and 5% 2-propanol. The solutions were aliquoted into heat-sealed crushable glass ampules. The solutions/ampules were placed on stability in chambers and maintained at 25° C./60% relative humidity (RH); 40° C./75% RH; and 5° C. (refrigerated) conditions. The 40% stabilized $H_2O_2$/5% IPA solutions remain stable ("in specification" according to ICH Harmonised Tripartite Guideline: Stability Testing of New Drug Substances and Products Q1A(R2)", current Step 4 version, dated 6 Feb. 2003) under both the 5° C. and 25° C. conditions at 12 months thus far.

Example 13

Solutions were prepared using stabilized hydrogen peroxide (FMC/PeroxyChem "Super D 50%" (FMC/PeroxyChem, Inc.) and 2-propanol 99% (Spectrum Chemical, USP Grade) to make a composition comprising 40% stabilized hydrogen peroxide and 5% 2-propanol. The solutions were prepared and aliquoted into amber, Type I borosilicate glass screw-top vials. Solutions were placed on stability in chambers and maintained at 25° C./60% relative humidity (RH) and 5° C. (refrigerated) conditions. The 40% stabilized $H_2O_2$/5% IPA solutions remain stable ("in specification" according to ICH Harmonised Tripartite Guideline: Stability Testing of New Drug Substances and Products Q1A(R2)", current Step 4 version, dated 6 Feb. 2003) under both the 25° C. conditions and 5° C. conditions at 12 months thus far.

Example 14

The following formulations were prepared using stabilized hydrogen peroxide (Peroxal CG 50® Arkema, Inc.), 2-propanol 99% (Spectrum Chemical, USP Grade) comprising about 44% to about 46% (w/w) stabilized hydrogen peroxide, 0% or 5% 2-propanol (as indicated in TABLE 3) and a gelling agent comprising either Carbopol ETD 2020, Carbopol 974P, or Carbopol Ultrez 10, in a concentration as indicated in TABLE 3. Disodium EDTA was also incorporated into all formulations as a chelating agent, and pH was adjusted to between about pH 3.5-about pH 4.0. In order to maximize the level of hydrogen peroxide in the gel formulations, the pH adjustment step (using 1% and 10% triethylamine) was performed after the formulations were prepared and therefore the composition (% weight-for-weight) in Table 3 is represented as the actual concentration of the formulations placed on stability.

TABLE 3

Gel Formulations

| Hydrogen Peroxide | Gelling Agent | 2-propanol |
|---|---|---|
| 45.91% | 0.48% w/w Carbopol ETD 2020 | 0% |

TABLE 3-continued

Gel Formulations

| Hydrogen Peroxide | Gelling Agent | 2-propanol |
|---|---|---|
| 46.11% | 0.48% w/w Carbopol 974 P | 0% |
| 45.23% | 0.47% w/w Carbopol Ultrez 10 | 0% |
| 44.29% | 0.49% w/w Carbopol 974 P | 5% |

The formulations were placed on stability in chambers and maintained at 25° C./60% relative humidity (RH); 40° C./75% RH; and 5° C. (refrigerated). The stabilized hydrogen peroxide gel formulations above were assessed for stability and based on evaluation of hydrogen peroxide recovery, pH, and Brookfield viscosity indicated that after t=6 weeks the Carbopol ETD, Carbopol 974 P, and Carbopol Ultrez 10 2020 maintained their hydrogen peroxide concentrations and their chemical & physical stability. Stability of this length of time is sufficient stability for a two-part gel formulation (or three or more part formulation with additional excipients such as IPA) mixed at or immediately before the time of application where, e.g., the hydrogen peroxide and the gelling agent are kept in separate compartments (e.g., separated by a frangible, in separate vials, separate syringes) and combined or mixed when needed.

Example 15

A randomized, double-blind, vehicle-controlled, within-subject comparison study of the safety, tolerability and effectiveness of hydrogen peroxide/2-propanol solutions in subjects with seborrheic keratosis was conducted. The main objective of this study was to evaluate the effectiveness of three different hydrogen peroxide/5% 2-propanol solutions (25% $H_2O_2$, 32.5% $H_2O_2$, and 40% $H_2O_2$) when applied to seborrheic keratosis (SK) target lesions on the back compared with a matching Vehicle. Secondary objectives included evaluating the safety and tolerability of the active solutions when applied topically in subjects with SK. Thirty-two subjects completed the study and were included in efficacy analyses. Subjects all had stable, clinically typical SKs, with at appropriate SK target lesions on the back.

Subjects were randomized to study medication (a unique study medication for each target lesion) and the study medications were applied to the assigned target lesions, each target lesion treated with a different study medication at Day 1. At follow-up 3 weeks after initial medication application, any target lesion that was not completely resolved received a retreatment study medication application. Subjects were followed up to evaluate treatment effects for a total of 78 days after the second study medication application.

A statistically significant difference in the efficacy of the active versus vehicle was first seen with the 40% solution beginning at Day 29, seven days after the second treatment. The length of the longest axis, the length of the perpendicular axis, and the height of the target lesion all showed statistically significant improvement compared with vehicle. All concentrations of the formulation were generally well tolerated, with only a mild "stinging" at the time of solution application and with mild dose-related transient local skin reactions (e.g., edema, erythema) at the time of application of the solution. There were no long-term pigmentary changes observed.

Example 16

A randomized, double-blind, vehicle-controlled, parallel group study was conducted using formulations of (i) 40% w/w hydrogen peroxide and 5% 2-propanol, (ii) 32.5% w/w hydrogen peroxide and 5% 2-propanol, and (iii) a vehicle solution for the treatment of seborrheic keratosis lesions on the trunk and extremities of patients. The main objective of this study was to evaluate the dose-response relationship of 2 concentrations of the hydrogen peroxide composition and its matching vehicle when applied to SK target lesions on the trunk/extremities. A further objective was to evaluate the safety and efficacy of 2 concentrations of the hydrogen peroxide composition and its matching vehicle when applied topically up to 2 times to SK target lesions on the trunk/extremities. The investigators identified four eligible SK target lesions on each subject. Each target lesion was treated a maximum of two times. For each subject, the four target lesions were all on the trunk/extremities. The skin of the patient was first cleansed with 70% 2-propanol, and a thin film of the hydrogen peroxide formulation was applied topically to the seborrheic keratosis lesion(s) on the trunk/extremities using a flocked doe-foot shaped applicator. Using firm pressure and an application technique that was appropriate for the target lesion size (e.g., dab and roll the applicator on smaller lesions; rub using a circular motion on larger lesions), the solution was applied for approximately 20-30 seconds. The investigator took care to minimize exposure to the surrounding normal skin. During the application process, excess study medication was removed from the surrounding skin using a clean absorbent wipe. The investigator ensured the target lesion was wet with study medication at the end of the 20-30 seconds and allowed the target lesion to remain undisturbed for approximately 1-2 minutes. This sequence was repeated up to 4 times with a break of 1-2 minutes in between applications. Follow-up was performed at numerous time points including 1 and 3 weeks after treatment. If needed, a second treatment session identical to the first was performed 3 weeks after the first treatment. Lesions were evaluated to assess their clinical response 12 weeks after the final treatment. One hundred sixty-nine subjects completed the study. The primary endpoint, the mean of per-subject percentages of target lesions judged to be clear on the PLA (Physician's Lesion Assessment) scale at the last visit was 45.1% for the 40% w/w hydrogen peroxide and 5% 2-propanol, and 26.8% for the 32.5% w/w hydrogen peroxide and 5% 2-propanol, compared with 4.8% for vehicle. A significantly greater improvement with both formulations compared with vehicle was seen starting at the first evaluation, with a dose response apparent at each visit. Local skin reactions were predominantly mild. The results of this study confirmed that the topical application of both the 40% $H_2O_2$ and 32.5% $H_2O_2$ solutions to SK lesions using the prescribed method, and formulations has the potential to safely and effectively resolve SK lesions without the need for analgesia and/or anesthesia, and with a minimal risk of hypopigmentation, hyperpigmentation, or scarring.

Example 17

A randomized, double-blind, vehicle-controlled, parallel group study was conducted using formulations of (i) 40% w/w hydrogen peroxide and 5% 2-propanol, (ii) 32.5% w/w hydrogen peroxide and 5% 2-propanol, and (iii) a solution vehicle for the treatment of seborrheic keratosis lesions on the face of patients. The main objective of this study was to evaluate the dose-response relationship of two concentrations of the hydrogen peroxide composition and its matching vehicle when applied to SK target lesions on the face. A further objective was to evaluate the safety and efficacy of two concentrations of the hydrogen peroxide composition and its matching vehicle when applied topically up to two times to SK target lesions on the face. The investigator identified one eligible SK target lesions on each subject's face. The target lesion was treated a maximum of two times. An oil based protectant (such as 100% white petrolatum) was optionally applied along the orbital rim and at the medial and lateral canthi; gently stretch the periorbital skin between the thumb and forefinger at the time of petrolatum application to distend any periorbital rhytides (e.g., "crow's feet") and ensure full coverage of the skin at the base of the rhytides to decrease the likelihood of tracking of the study medication towards the eye. The subject was additionally instructed to hold an absorbent pad in the appropriate area of the eye to absorb any excess study medication that might track away from the target lesion and to keep both eyes closed during the entire study medication application procedure. The skin of the patient was first cleansed with 70% 2-propanol, and a thin film of the hydrogen peroxide formulation was applied topically to the seborrheic keratosis lesion(s) on the patient's face using a flocked doe-foot shaped applicator. Using firm pressure and an application technique that was appropriate for the target lesion size (e.g., dab and roll the applicator on smaller lesions; rub using a circular motion on larger lesions), the solution was applied for approximately 20-30 seconds. The investigator took care to minimize exposure to the surrounding normal skin. During the application process, excess study medication was removed from the surrounding skin using a clean absorbent wipe. The investigator ensured the target lesion was wet with study medication at the end of the 20-30 seconds and allowed the target lesion to remain undisturbed for approximately 60 seconds. This sequence was repeated up to 4 times with a break of 1-2 minutes in between applications. Follow-up was at several time points including 3 weeks after treatment. If needed, a second treatment session identical to the first was performed 3 weeks after the first treatment. Lesions were evaluated to assess their clinical response 12 weeks after the final treatment. One hundred sixteen subjects completed the study. The primary endpoint was a pairwise comparison between the vehicle and each active medication group based on mean change from baseline in PLA (Physician's Lesion Assessment) score at each post-baseline visit using ANCOVA. A significantly greater improvement with both formulations compared with vehicle was seen starting at the first evaluation, with a dose response apparent at each visit. Local skin reactions were predominantly mild. The results of this study confirmed that the topical application of both the 40% $H_2O_2$ and 32.5% $H_2O_2$ solutions to SK lesions on the face using the prescribed method and formulations has the potential to safely and effectively resolve SK lesions without the need for analgesia and/or anesthesia, and with a minimal risk of hypopigmentation, hyperpigmentation, or scarring.

Example 18

A 60 year old white male with Fitzpatrick Type III skin had applications of a topical solution comprising 40% H2O2 and 5% IPA to a clinically typical appearing ovoid seborrheic keratosis in the right temporal area measuring 18.7× 24.0 mm in size. Prior to commencing the application of the solution, petroleum jelly was applied with a cotton-tipped applicator to the area surrounding the keratotic lesion in order to prevent the solution from tracking along static and dynamic rhytides and better confine the solution to the lesion.

The solution was applied as described: The target lesion was thoroughly cleansed by firmly rubbing with a cotton-tipped applicator wetted with 70% isopropyl alcohol (IPA). Care was taken to keep the IPA and the H2O2 solution vial away from the face of the subject. After cleansing the lesion, the applicator, a nylon flocked doe-foot shaped applicator was wetted with a quantity of peroxide/IPA solution study medication sufficient to wet the target lesion with a thin film. Using medium-to-firm pressure and an application technique that was appropriate for the target lesion size, the solution was applied using a circular motion in an amount sufficient to cover the entire surface of the lesion (seborrheic keratosis) for approximately 30 seconds. Care was taken to minimize exposure to the surrounding normal skin. During the application process excess study medication was removed from the surrounding skin using a clean absorbent wipe to dab away any excess. The target lesion was then allowed to remain undisturbed for approximately 1-2 minutes. The solution remained confined to the area of application on the skin lesion. After the approximately 1-2 minutes, the application process was repeated until the peroxide/IPA solution had been applied to the target lesion a total of 4 times.

The procedure was well tolerated and without complications. The maximal discomfort was described as a "stinging" that peaked at "about 1" (mild) on a 5-point scale (0-4). At the conclusion of the application session, the area demonstrated a "superficial whitening" reaction that extended over only the area of application of the solution, with minimal accompanying erythema. No solution ran-off the lesion and there was no whitening or any adverse effect outside the area of application. Upon questioning approximately 20 minutes following the last application, the discomfort was noted to have already completely resolved (was rated at "0/4). Evaluation about 75 minutes after the last application revealed almost complete resolution of the "superficial whitening" reaction.

Over the next several days, superficial crusting developed over the treated area and over the next several weeks the lesion sloughed off without complication. Follow-up 38 days after the initial application revealed the treatment area to be completely healed with near complete resolution of the original treated lesion, but for a small area at the inferior edge of the prior application site. The area was again treated at that time using the method outlined above, with the same procedure, same response, and no complications. Superficial crusting again developed over the treated area, which resolved within "about a week" according to the subject. A follow-up 31 days after the second application revealed complete resolution of the lesion with outstanding cosmesis. The subject was extremely pleased with the results. A long-term follow-up 193 days after the first application (155 days after the second application) revealed no recurrence of the original SK lesion and that the outstanding cosmesis was maintained.

Example 19

A vehicle-controlled, within subject study of the bioavailability of a hydrogen peroxide and 2-propanol topical solution administered under maximal use conditions in subjects with clinically typical seborrheic keratosis on the back will be undertaken. The main objective of this study will be to assess the relative bioavailability of a solution of 40% hydrogen peroxide/5% 2-propanol when administered topically under conditions of maximum use in subjects with seborrheic keratosis (SK) on the trunk, face, and extremities.

A further objective will be to evaluate the safety of the 40% hydrogen peroxide/5% 2-propanol solution when administered topically under conditions of maximum use in subjects with seborrheic keratosis on the trunk, face, and extremities. It is expected that each subject will have 10 SK target lesions on the trunk, face, and extremities for treatment and evaluation. At least one target lesion on each subject will be on the face. During this study, the investigator will identify 10 eligible SK lesions on each subject's trunk, face, and extremities. Each SK target lesion will be treated once (first) with a solution vehicle to obtain non-treated pharmacokinetic blood samples, and then, one week later, with the active formulation.

Blood samples for pharmacokinetic (PK) analysis of hydrogen peroxide will be collected at time points ranging from 0 hour (just prior to the study medication application) to at least about 6 hours after the study medication application is completed. PK samples will be collected at the same time of day to eliminate complications associated with any potential diurnal variation in endogenous hydrogen peroxide plasma levels. The investigator will measure clinical parameters of the lesions including the lesion dimensions (i.e., length and width) for each target lesion at Visit 1. A statistical analysis will be performed and relative bioavailability will be calculated for the active solution compared to vehicle solution. The statistical analysis may include an analysis of variance (ANOVA) for the PK parameters of Cmax, AUC0-t, and AUC0-∞. Data for Cmax and AUC0-t will be subject to natural log transformation prior to analysis.

It is anticipated that the main objective of this study will be achieved- to assess the relative bioavailability of a solution of 40% hydrogen peroxide/5% 2-propanol when administered topically under conditions of maximum use in subjects with seborrheic keratosis (SK) on the trunk, face, and extremities. It is anticipated that no measurable blood level of hydrogen peroxide will be detected under these maximal use conditions. It is anticipated that the further objective—to evaluate the safety of the 40% hydrogen peroxide/5% 2-propanol solution when administered topically under conditions of maximum use in subjects with seborrheic keratosis on the trunk, face, and extremities will be achieved. It is anticipated that the test solution will be found to be safe for use when administered topically under these maximal use conditions.

Example 20

An applicator having a topical composition solution having 40% hydrogen peroxide and 5% isopropyl alcohol disposed within a frangible ampoule disposed in the applicator body of the applicator is obtained for treating a patient having seborrheic keratosis lesions on the face, trunk, and extremities. The lesion is cleansed by rubbing with a 70% isopropyl alcohol wipe, before treatment. The applicator is activated by depressing the exterior of the applicator body with thumb and forefinger to break the frangible ampule and release the solution. The applicator should be held away from the patient while activating the package. After the applicator is activated, the cap is removed, and the tip is wetted by gently squeezing the exterior of the applicator body until the package tip is wet with a quantity of solution sufficient to wet the lesion with a thin film.

Using appropriate pressure, the solution is applied to the lesion using a circular motion for 20 to 30 seconds. During the application, any excess solution should be removed from surrounding skin using a clean absorbent wipe.

The treated lesion is undisturbed for approximately 1 minute and then the application is repeated. This can be repeated up to 4 times until the lesion(s) is completely saturated with solution.

After completing treatment of each targeted lesion, the lesion(s) should not be disturbed until the solution has completely dried. The treated lesions may be dabbed, without wiping, with an absorbent wipe to ensure the treated lesion is dry before the patient is released.

If the lesion(s) has not completely cleared after approximately three weeks, further treatment(s) may be applied by following the initial procedure.

Example 21

An applicator will have an applicator body formed from HDPE, LDPE, or an HDPE/LDPE blend, with a borosilicate glass ampoule arranged therein. A single treatment dose of a formulation of 40% w/w hydrogen peroxide and 5% 2-propanol will be disposed within the ampoule. An operator will hold the applicator in their hand in a manner similar to holding a writing utensil to write. The operator will position an index finger on a first pressure area arranged on an external surface of the applicator body and the opposing thumb on a second pressure area arranged on a substantially opposite side of the applicator body. The operator will squeeze the applicator body using their index finger and opposing thumb with sufficient force to rupture the ampoule arranged within the applicator body between the first pressure area and the second pressure area. The operator will shift the position of their hand on the applicator down to a grip area on a proximal portion of the applicator body. The operator will cause the formulation to be released from a nylon flocked doe-foot shaped tip of the applicator in fluid communication with the applicator tube by squeezing on the grip area using their fingers.

A filter formed from LDPE that is coated with a silicone material configured to impart hydrophobic properties to the filter will be arranged within the applicator to filter the shards from the ruptured ampoule. The filter will prevent the flow of the formulation therethrough unless the operator applies pressure to the applicator body. The operator will control a rate of flow from the applicator onto a target application site (e.g., a skin lesion) by varying the pressure applied to the grip area. The operator will then treat the target lesion or lesions.

Although the present invention has been described in considerable detail with reference to certain preferred embodiments thereof, other versions are possible. Therefore the spirit and scope of the appended claims should not be limited to the description and the preferred versions contained within this specification.

What is claimed is:

1. A method of treating seborrheic keratosis in a human in need thereof, comprising topically administering to the human a composition comprising about 40% w/w of stabilized hydrogen peroxide, wherein the compound used to stabilize the hydrogen peroxide comprises stannate, sodium pyrophosphate, organophosphonate, nitrate, phosphoric acid, colloidal silicate, or a combination thereof.

2. The method of claim 1, wherein the composition is administered once to the human.

3. The method of claim 1, wherein the composition is administered twice to the human.

4. The method of claim 3, wherein the second administration of the composition to the human occurs about 3 weeks after the first administration of the composition to the human.

5. The method of claim 1, wherein the composition has a surface tension of about 42 mN·m−1 to about 55 mN·m−1 at 37° C.

6. The method of claim 1, wherein the composition is stable for at least two years at 5° C., at least one year at 30° C., at least 6 months at 40° C., or a combination thereof.

7. The method of claim 1, wherein the composition has a mean steady state release of hydrogen peroxide between 0.5 hours and 4 hours of between about 1000 μg/cm$^2$/hour and about 1750 μg/cm$^2$/hour.

8. The method of claim 1, wherein the composition has a mean redox potential of about 415 mV to about 430 mV.

9. The method of claim 1, wherein the composition has a pH of about 3.5 to about 4.

10. The method of claim 1, wherein the composition is a solution.

11. The method of claim 1, wherein the composition is a gel.

12. The method of claim 1, wherein administering the composition comprises contacting the seborrheic keratosis with an applicator selected from the group consisting of a sponge, a swab, a foam tipped stick, a cotton ball, a brush, a woven or non-woven fabric, roller, gauze, a glove, a pen-type applicator, a flocked, doe-foot applicator or a combination thereof.

13. The method of claim 1, wherein administering the composition comprises contacting the seborrheic keratosis with a tip of an applicator, wherein the applicator comprises:
a frangible ampoule having the composition disposed therein,
an applicator body having the frangible ampoule arranged therein;
an applicator hub in fluid communication with the applicator body;
the tip arranged at a proximal end of the applicator hub; and
a filter arranged between the frangible ampoule and the tip.

14. The method of claim 13, wherein administering the composition comprises controlling a flow rate of the topical composition out of the tip by varying a squeezing force applied to the exterior surface of the applicator body.

15. The method of claim 13, wherein administering the composition comprises contacting the tip with the seborrheic keratosis whereby the topical composition dispenses through the tip onto the targeted lesion.

16. The method of claim 13, wherein administering the composition further comprises applying pressure to a pressure area arranged on an outer surface of the applicator body causing the frangible ampoule to rupture.

17. The method of claim 13, wherein administering the composition comprises causing the frangible ampoule to rupture and release the topical composition through the tip; and contacting the tip to the seborrheic keratosis.

18. The method of claim 1, wherein the composition further comprises a surface tension modifying agent.

19. The method of claim 1, wherein the composition further comprises an alcohol.

20. The method of claim 1, wherein the composition further comprises a stabilizer.

21. The method of claim 1, wherein the composition further comprises a gelling agent.

22. The method of claim 1, wherein the composition further comprises an excipient.

23. The method of claim 1 further including debriding the seborrheic keratosis.

24. The method of claim 1, wherein no additional active agent is needed to treat the seborrheic keratosis.

25. The method of claim 1, wherein no additional therapeutic intervention is needed to treat the seborrheic keratosis.

* * * * *